(12) United States Patent
Reed

(10) Patent No.: US 8,703,905 B2
(45) Date of Patent: Apr. 22, 2014

(54) ENDOPLASMIC RETICULUM LOCALIZATION SIGNALS

(75) Inventor: Thomas Reed, Arlington, VA (US)

(73) Assignee: Intrexon Corporation, Blacksburg, VA (US)

( * ) Notice: Subject to any disclaimer, the term of this patent is extended or adjusted under 35 U.S.C. 154(b) by 82 days.

(21) Appl. No.: 13/369,649

(22) Filed: Feb. 9, 2012

(65) Prior Publication Data
US 2013/0253167 A1    Sep. 26, 2013

Related U.S. Application Data

(62) Division of application No. 12/757,785, filed on Apr. 9, 2010, now Pat. No. 8,211,998, which is a division of application No. 11/901,869, filed on Sep. 19, 2007, now Pat. No. 7,897,394.

(60) Provisional application No. 60/826,517, filed on Sep. 21, 2006.

(51) Int. Cl.
| C07K 14/00 | (2006.01) |
| C07H 21/02 | (2006.01) |
| C07H 21/04 | (2006.01) |
| C12N 1/20  | (2006.01) |
| C12P 21/06 | (2006.01) |

(52) U.S. Cl.
USPC ............... 530/300; 435/252.3; 435/254.1; 435/69.1; 435/320.1; 536/23.1; 536/23.4

(58) Field of Classification Search
None
See application file for complete search history.

(56) References Cited

U.S. PATENT DOCUMENTS

| 7,071,295 B2   | 7/2006  | Reed        |
| 7,897,394 B2   | 3/2011  | Reed        |
| 8,211,998 B2   | 7/2012  | Reed        |
| 2004/0185556 A1| 9/2004  | Reed        |
| 2008/0050808 A1| 2/2008  | Reed et al. |
| 2008/0250515 A1| 10/2008 | Reed        |
| 2011/0197291 A1| 8/2011  | Reed        |

FOREIGN PATENT DOCUMENTS

| WO | WO 2005/040336 A2 | 5/2005 |
| WO | WO 2005/116231 A1 | 12/2005 |

OTHER PUBLICATIONS

Andersson, H., et al., "Protein targeting to endoplasmic reticulum by dilysine signals involves direct retention in addition to retrieval," *J. Biol. Chem. 274*:15080-4, American Society for Biochemistry and Molecular Biology, United States (1999).
Cocquerel, L., et al., "The transmembrane domain of hepatitis C virus glycoprotein E1 is a signal for static retention in the endoplasmic reticulum," *J. Virol 73*:2641-9, American Society for Microbiology, United States (1999).
Fons, R., et al., "Substrate-specific function of the translocon-associated protein complex during translocation across the ER membrane," *J. Cell Biol. 160*:529-39, American Society for Biochemistry and Molecular Biology, United States (2003).
Gabathuler, R., et al., "The endoplasmic reticulum retention signal of the E3/19K protein of adenovirus type 2 consists of three separate amino acid segments at the carboxy terminus," *J. Cell Biol. 111* : 1803-10, American Society for Biochemistry and Molecular Biology, United States (1990).
Honsho, M., et al., "Retention of cytochrome b5 in the endoplasmic reticulum is transmembrane and luminal domain-dependent," *J. Biol. Chem. 273*:20860-6, American Society for Biochemistry and Molecular Biology, United States (1998).
Ma, Y., et al., "A 15-residue bifunctional element in D-AKAP1 is required for both endoplasmic reticulum and mitochondrial targeting," *J. Biol. Chem. 277*:27328-36, American Society for Biochemistry and Molecular Biology, United States (2002).
Mitoma, J., et al., "The carboxy-terminal 10 amino acid residues of cytochrome b5 are necessary for its targeting to the endoplasmic reticulum," *Embo. J. 11*:4197-203, Nature Publishing Group, United Kingdom (1992).
Mziaut, H., et al., "Targeting proteins to the lumen of endoplasmic reticulum using N-terminal domains of 11 beta-hydroxysteroid dehydrogenase and the 50-kDa esterase," *J. Biol. Chem. 274*:14122-9, American Society for Biochemistry and Molecular Biology, United States (1999).
Parker, A., et al., "Targeting of inositol 1,4,5-trisphosphate receptors to the endoplasmic reticulum by multiple signals within their transmembrane domains," *J. Biol. Chem. 279*:23797-805, American Society for Biochemistry and Molecular Biology, United States (2004).
Pottekat, A., et al., "Subcellular localization and targeting of N-acetylglucosaminyl phosphatidylinositol de-N-acetylase, the second enzyme in the glycosylphosphatidylinositol biosynthetic pathway," *J. Biol. Chem. 279*:15743-51, American Society for Biochemistry and Molecular Biology, United States (2004).
Ren, Z., et al., "Cell surface expression of GluR5 kainate receptors is regulated by an endoplasmic reticulum retention signal," *J. Biol. Chem. 278*:52700-9, American Society for Biochemistry and Molecular Biology, United States (2003).

(Continued)

*Primary Examiner* — Nashaat Nashed
(74) *Attorney, Agent, or Firm* — Sterne, Kessler, Goldstein & Fox, P.L.L.C.

(57) ABSTRACT

The invention relates to cellular localization signals. In particular, the invention relates to endoplasmic reticulum localization signals in monomeric or multimeric form. The localization signals are utilized as research tools or are linked to therapeutics. Disclosed are methods of making and using polypeptides and modified polypeptides as signals to localize therapeutics, experimental compounds, peptides, proteins and/or other macromolecules to the endoplasmic reticulum of eukaryotic cells. The polypeptides of the invention optionally include linkage to reporters, epitopes and/or other experimental or therapeutic molecules. The invention also encompasses polynucleotides encoding the localization signals and vectors comprising these polynucleotides.

14 Claims, 17 Drawing Sheets

(56) References Cited

OTHER PUBLICATIONS

Figure 2A:

Szczesna-Skorupa, E., et al., "The juxtamembrane sequence of cytochrome P-450 2C1 contains an endoplasmic reticulum retention signal," *J. Biol. Chem.* 276:45009-14, American Society for Biochemistry and Molecular Biology, United States (2001).

Vainauskas, S., et al.. "Endoplasmic reticulum localization of Gaa1 and PIG-T, subunits of the glycosylphosphatidylinositol transamidase complex," *J. Biol. Chem.* 280:16402-9, American Society for Biochemistry and Molecular Biology, United States (2005).

Watanabe, R., et al., "PIG-A and PIG-H, which participate in glycosylphosphatidylinositol anchor biosynthesis, form a protein complex in the endoplasmic reticulum," *J. Biol. Chem.* 271:26868-75, American Society for Biochemistry and Molecular Biology, United States (1996).

Zarei, M., et al., "An endoplasmic reticulum trafficking signal prevents surface expression of a voltage- and Ca2+-activated K+ channel splice variant," *Proc. Natl. Acad. Sci. USA 101*:10072-7, National Academy of Sciences, United States (2004).

Zarei, M., et al., "A novel MaxiK splice variant exhibits dominant-negative properties for surface expression," *J. Biol. Chem.* 276:16232-9, American Society for Biochemistry and Molecular Biology, United States (2001).

| MONOMER X | MONOMER X |

FIGURE 1A

| MONOMER X | MONOMER X | MONOMER X |

FIGURE 1B

| MONOMER X | MONOMER X | MONOMER X | MONOMER X | MONOMER X |

FIGURE 1C

| LOCALIZATION SIGNAL = (MONOMER X)$_n$ where n > 1 |

FIGURE 1D

| MONOMER X | MONOMER Y |

FIGURE 3A

| MONOMER X | MONOMER Z | MONOMER Z |

FIGURE 3B

| MONOMER X | MONOMER Y | MONOMER X | MONOMER Z | MONOMER A |

FIGURE 3C

| MONOMER A | MONOMER B | MONOMER C | MONOMER D |

FIGURE 3D

| MONOMER A | MONOMER A | MONOMER B | MONOMER C |

FIGURE 3E

| MONOMER B | SPACER | MONOMER A |

FIGURE 4A

| MONOMER X | SPACER | MONOMER Y | SPACER | MONOMER Y |

FIGURE 4B

| MONOMER X | SPACER | MONOMER Y | MONOMER Y | MONOMER X |

FIGURE 4C

| MONOMER A | SPACER | MONOMER B | SPACER | MONOMER B | SPACER | MONOMER C |

FIGURE 4D

| MONOMER A | SPACER | MONOMER B | SPACER | MONOMER B | SPACER |

FIGURE 4E

| LOCALIZATION SIGNAL | SPACER | EPITOPE |

FIGURE 5A

| EPITOPE | SPACER | LOCALIZATION SIGNAL |

FIGURE 5B

| LOCALIZATION SIGNAL | EPITOPE |

FIGURE 5C

| EPITOPE | LOCALIZATION SIGNAL |

FIGURE 5D

| EPITOPE | SPACER | LOCALIZATION SIGNAL | SPACER |

FIGURE 5E

| SPACER | EPITOPE | SPACER | LOCALIZATION SIGNAL |

FIGURE 5F

| LOCALIZATION SIGNAL | EPITOPE | SPACER |

FIGURE 5G

| SPACER | EPITOPE | LOCALIZATION SIGNAL |

FIGURE 5H

| POLYPEPTIDE | LOCALIZATION SIGNAL |

FIGURE 7A

| LOCALIZATION SIGNAL | POLYPEPTIDE |

FIGURE 7B

| POLYPEPTIDE | SPACER | LOCALIZATION SIGNAL |

FIGURE 7C

| LOCALIZATION SIGNAL | SPACER | POLYPEPTIDE |

FIGURE 7D

| SPACER | POLYPEPTIDE | SPACER | LOCALIZATION SIGNAL |

FIGURE 7E

| LOCALIZATION SIGNAL | SPACER | POLYPEPTIDE | SPACER |

FIGURE 7F

| LOCALIZATION SIGNAL | POLYPEPTIDE | SPACER |

FIGURE 7G

| SPACER | POLYPEPTIDE | LOCALIZATION SIGNAL |

FIGURE 7H

| PROMOTER | POLYPEPTIDE | OPTIONAL REPORTER | LOCALIZATION SIGNAL | STOP | POLY-A |

FIGURE 9A

| PROMOTER | OPTIONAL REPORTER | OPTIONAL EPITOPE | POLYPEPTIDE | LOCALIZATION SIGNAL | STOP | POLY-A |

FIGURE 9B

| PROMOTER | LOCALIZATION SIGNAL | OPTIONAL EPITOPE | POLYPEPTIDE | STOP | POLY-A |

FIGURE 9C

| PROMOTER | LOCALIZATION SIGNAL | POLYPEPTIDE | OPTIONAL EPITOPE | OPTIONAL REPORTER | STOP | POLY-A |

FIGURE 9D

| PROMOTER | POLYPEPTIDE | LOCALIZATION SIGNAL | STOP | POLY-A |

FIGURE 9E

| PROMOTER | LOCALIZATION SIGNAL | POLYPEPTIDE | STOP | POLY-A |

FIGURE 9F

| PROMOTER | LOCALIZATION SIGNAL | REPORTER | STOP | POLY-A |

FIGURE 9G

| PROMOTER | REPORTER | LOCALIZATION SIGNAL | STOP | POLY-A |

FIGURE 9H

ENDOPLASMIC RETICULUM LOCALIZATION SIGNALS

This application claims benefit of priority to provisional application 60/826,517, filed 21 Sep. 2006.

REFERENCE TO SEQUENCE LISTING SUBMITTED ELECTRONICALLY VIA EFS-WEB

This application includes a "Sequence_Listing.txt," 143,710 bytes, created on Nov. 12, 2013, and submitted electronically via EFS-Web, which is hereby incorporated by reference in its entirety.

FIELD OF INVENTION

The invention relates to subcellular localization signals. In particular, the invention relates to endoplasmic reticulum localization signals in monomeric or multimeric form. The multimers may be homomultimers or heteromultimers. The monomers and multimers are utilized as research tools or are linked to therapeutics.

This application has subject matter related to application Ser. Nos. 10/724,532 (U.S. Pat. No. 7,071,295), 10/682,764 (US2004/0185556, PCT/US2004/013517, WO2005/040336), 11/233,246, and US2004057201 IP (WO2005116231). Each of these patents and applications is hereby incorporated by reference.

BACKGROUND OF THE INVENTION

Drugs that act intracellularly generally enter cells by diffusion. Most drugs are small molecules because they have the ability to diffuse across plasma membranes or organelle membranes to reach their site of action. To increase the bioavailability of a drug, often small molecules must be modified and/or formulated for greater solubility and/or permeability, depending on route of administration. Even small diffusible drugs may not be efficacious at their site of action. For example, multidrug resistance (MDR) may be present, which results in active efflux of drugs that enter cells with MDR. MDR often occurs in cancer cells.

In contrast to small molecules, high molecular weight compounds and polymer drugs, such as polynucleotides, polypeptides, and other macromolecules have little to no ability to diffuse across membranes. High molecular weight material is generally internalized by endocytosis. The addition of affinity binding partners to high molecular weight material can direct the high molecular weight compound to specific cells, and thereby result in increased selective uptake. However, once endocytosed, the material still remains separated from the cellular cytoplasm by a biological membrane.

Endocytosed material is often delivered to the lysosome, where material sensitive to lysosomal enzymes is quickly degraded if steps are not taken to protect its breakdown or to facilitate escape from the lysosome. Delivery of high molecular weight compounds to their site of action at effective levels is a problem. It is therefore desirable to improve delivery to a desired subcellular compartment.

One of the first cellular trafficking signals identified was the endoplasmic reticulum (ER) retention signal, KDEL (SEQ ID NO: 75), which prevents secretion of proteins routed to the endoplasmic reticulum. When this signal is expressed toward the carboxy terminus in proteins that are normally secreted, these proteins are retained in the endoplasmic reticulum and not secreted (Munro and Pelham, Cell 1987, 48:899-907).

Endogenous and exogenous proteins have varying targeting domains within their primary sequence. Such proteins include those described in Andersson, et al. 1999 J Biol Chem 274:15080-4, Cocquerel, et al. 1999 J Virol 73:2641-9, Fons, et al. 2003 J Cell Biol 160:529-39, Gabathuler, et al. 1990 J Cell Biol 111:1803-10, Honsho, et al. 1998 J Biol Chem 273:20860-6, Ma, et al. 2002 J Biol Chem 277:27328-36, Mitoma, et al. 1992 Embo J 11:4197-203, Mziaut, et al. 1999 J Biol Chem 274:14122-9, Parker, et al. 2004 J Biol Chem 279:23797-805, Pottekat, et al. 2004 J Biol Chem 279:15743-51, Ren, et al. 2003 J Biol Chem 278:52700-9, Szczesna-Skorupa, et al. 2001 J Biol Chem 276:45009-14, Vainauskas, et al. 2005 J Biol Chem 280:16402-9, Watanabe, et al. 1996 J Biol Chem 271:26868-75, Zarei, et al. 2004 Proc Natl Acad Sci USA 101:10072-7, and Zarei, et al. 2001 J Biol Chem 276:16232-9.

An aspect of the invention is to provide novel monomeric and novel multimeric endoplasmic reticulum localization signals by modifying one or more proteins that naturally locate to the endoplasmic reticulum by truncation or by amino acid substitution. Truncations, amino acid substitutions, and other modifications of known ER-locating proteins are made to minimize endogenous biological activities other than localization. In general, the invention relates to cellular localization signals. More specifically, the invention relates to endoplasmic reticulum localization signals in monomeric or multimeric form. The multimers may be homomultimers or heteromultimers. Multimers are made to exploit cooperation and synergism among individual signals in order to create a chimeric localization signal with a strength and/or performance greater than the constituent individual parts. The monomers and multimers are utilized as research tools or are linked to therapeutics. Disclosed are methods of making and using polypeptides and modified polypeptides as signals to localize therapeutics, experimental compounds, peptides, proteins and/or other macromolecules to the endoplasmic reticulum and contiguous structures of eukaryotic cells. The polypeptides of the invention optionally include linkage to reporters, epitopes and/or other experimental or therapeutic molecules. The invention also encompasses polynucleotides encoding the localization signals and vectors comprising these polynucleotides.

DETAILED DESCRIPTION OF POLYPEPTIDE AND POLYNUCLEOTIDE SEQUENCES SEQ ID NOS:1-16 are example endoplasmic reticulum localization signals and polynucleotides encoding them.

Specifically, the polypeptide of SEQ ID NO:1 is encoded by SEQ ID NOS:2-6, wherein the codons of SEQ ID NOS:3-6 have been optimized for vector insertion. SEQ ID NO:4 and SEQ ID NO:6 include flanking restriction sites. SEQ ID NO:5 and SEQ ID NO:6 differ from SEQ ID NO:3 and SEQ ID NO:4, respectively, in that an internal EcoRI restriction has been removed. SEQ ID NO:1 is an embodiment of a multimeric ER localization signal of the structure A-S1-B-52-B-53-C, wherein A is SEQ ID NO:42, B is SEQ ID NO:72, and C is SEQ ID NO:75, and wherein 51 is a two amino acid spacer with the sequence EF, S2 is a four amino acid spacer with the sequence, PGAG (SEQ ID NO: 78), and S3 is a three amino acid spacer with the sequence, AAA. A multimeric localization signal of structure A-S1-B-52-B-53-C is also called herein a heteromultimer (see FIG. 4D).

Figure 11:
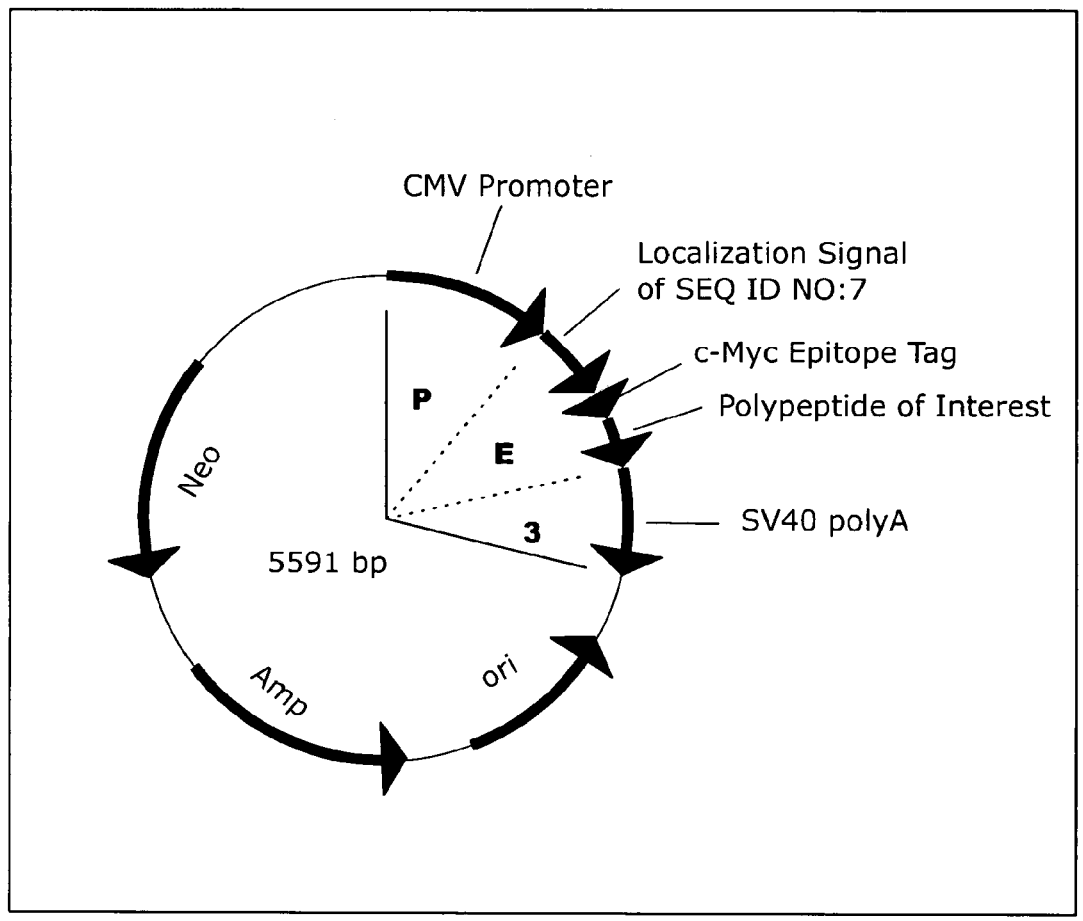
Figure 12:
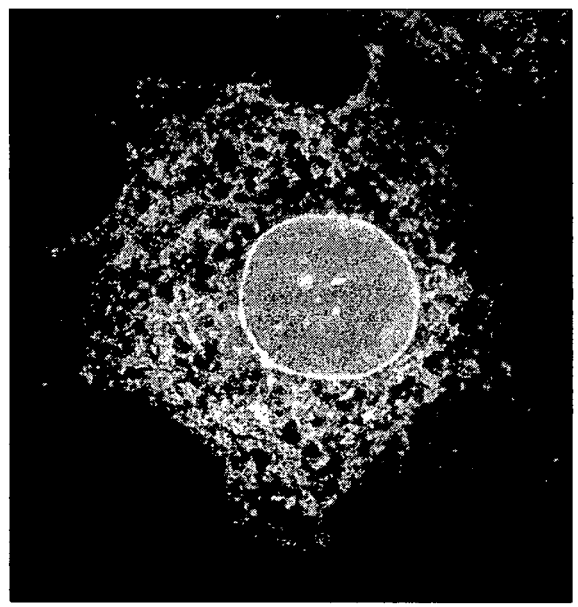

SEQ ID NO:7 is an embodiment of a multimer of the structure X-S1-Y-S2-Y-S3, wherein X is SEQ ID NO:60, Y is SEQ ID NO:72, 51 is a seven amino acid spacer with the sequence EFGGGGG (SEQ ID NO: 79), S2 is a four amino acid spacer with the sequence PGAG (SEQ ID NO: 78), and S3 is a five amino acid spacer with the sequence AAPAA (SEQ ID NO: 80). The polypeptide of SEQ ID NO:7 is encoded by SEQ ID NOS:8-12, wherein the codons of SEQ ID NOS:9-12 have been optimized for vector insertion. SEQ ID NO:10 and SEQ ID NO:12 include flanking restriction sites. SEQ ID NO:9 and SEQ ID NO:10 differ from SEQ ID NO:11 and SEQ ID NO:12, respectively, in that an internal EcoRI restriction has been removed. A multimer of structure X-S1-Y-S2-Y-S3 is also called herein a heteromultimer (see FIG. 4E). A vector map of a vector containing SEQ ID NO:7 is shown in FIG. 11 (labeled Localization Signal). SEQ ID NO:7 was expressed in Cos7 cells as shown in FIG. 12.

SEQ ID NO:13 is an embodiment of a multimer of the structure X-S1-Y-S2-Y, wherein X is SEQ ID NO:60, Y is SEQ ID NO:72, S1 is a seven amino acid spacer with the sequence EFGGGGG (SEQ ID NO: 79), and S2 is a four amino acid spacer with the sequence PGAG (SEQ ID NO: 78). The polypeptide of SEQ ID NO:13 is encoded by SEQ ID NO:14, SEQ ID NO:15 and by SEQ ID NO:16, wherein the codons of SEQ ID NO:15 and SEQ ID NO:16 have been optimized for vector insertion. SEQ ID NO:16 includes flanking restriction sites. A multimer of structure X-S1-Y-S2-Y is also called herein a heteromultimer (see FIG. 4B).

SEQ ID NOS:17-38 are full length sequences of proteins that localize to the endoplasmic reticulum. These sequences have the following public database accession numbers: NP_001007236, Q9Y2B2, CAA77776, AAQ19305, AAF81759, P00180, Q969N2, NP_071581, NP_003479, CAI20063, Q7M370, CAA23446, AAS89356, BAA19247, B34759, AAB97308, AAP35497, NP_999425, NP_999113, XP_343784.

SEQ ID NOS:39-69 represent examples of monomeric endoplasmic reticulum localization signals. SEQ ID NOS: 39-69 are subsequences of SEQ ID NOS:17-38, which represent examples of peptide sequences that confer endoplasmic reticulum routing and/or retention.

SEQ ID NOS:70-77 represent examples of monomeric endoplasmic reticulum retention signals.

DETAILED DESCRIPTION OF DRAWINGS

Figure 2B:
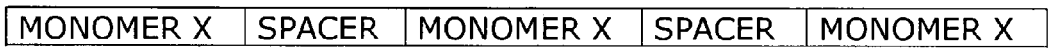
Figure 2C:
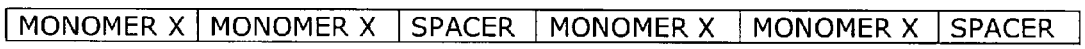
Figure 6A:
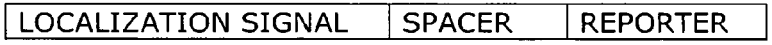
Figure 6B:
Figure 6C:
Figure 6D:
Figure 6E:
Figure 6F:
Figure 6G:
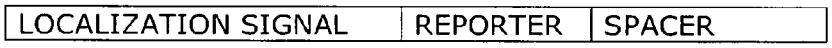
Figure 6H:
Figure 8A:
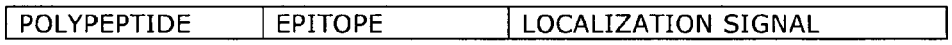
Figure 8B:
Figure 8C:
Figure 8D:
Figure 8E:
Figure 8F:
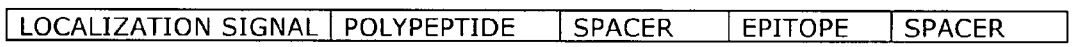
Figure 8G:
Figure 8H:

FIGS. 1A-1D show examples of homomultimeric localization signals without spacers.
FIGS. 2A-2C show examples of homomultimeric localization signals with spacers.
FIGS. 3A-3E show examples of heteromultimeric localization signals without spacers.
FIGS. 4A-4E show examples of heteromultimeric localization signals with spacers.
FIGS. 5A-5H show examples of localization signals linked to an epitope tag.
FIGS. 6A-6H show examples of localization signals linked to a reporter.
FIGS. 7A-7H show examples of localization signals linked to an experimental or therapeutic polypeptide.
FIGS. 8A-8H show examples of localization signals linked to an epitope tag, and an experimental or therapeutic polypeptide.
FIGS. 9A-9H show examples of gene constructs where localization signals are linked to an experimental or therapeutic polypeptide, with an optional epitope tag and/or reporter.
FIGS. 10A-10D show examples of vectors containing endoplasmic reticulum localization signal gene constructs.
FIG. 11 shows a diagram of the vector used to transform the Cos7 cells of FIG. 12. Abbreviations are as follows: Neo stands for neomycin resistance gene; Amp stands for ampicillin resistance gene; on stands for origin of replication; P stands for promoter domain; E stands for expression domain; 3 stands for 3' regulatory domain.

FIG. 12 shows activity of the endoplasmic reticulum localization signal of SEQ ID NO:7. Cos7 cells were transfected with DNA from the vector shown in FIG. 11. The green color identifies the location of antibodies which recognize the c-Myc epitope linked to chloramphenicol acetyltransferase fragment and the localization signal. The red color identifies the ER resident protein calreticulin. This image is a co-localization image, wherein yellow areas represent colocalization of red and green, and demonstrate the targeting of a polypeptide of interest (chloramphenicol acetyltransferase fragment) to the endoplasmic reticulum using the localization signal of SEQ ID NO:7.

Figures 13A, 13B, 13C:
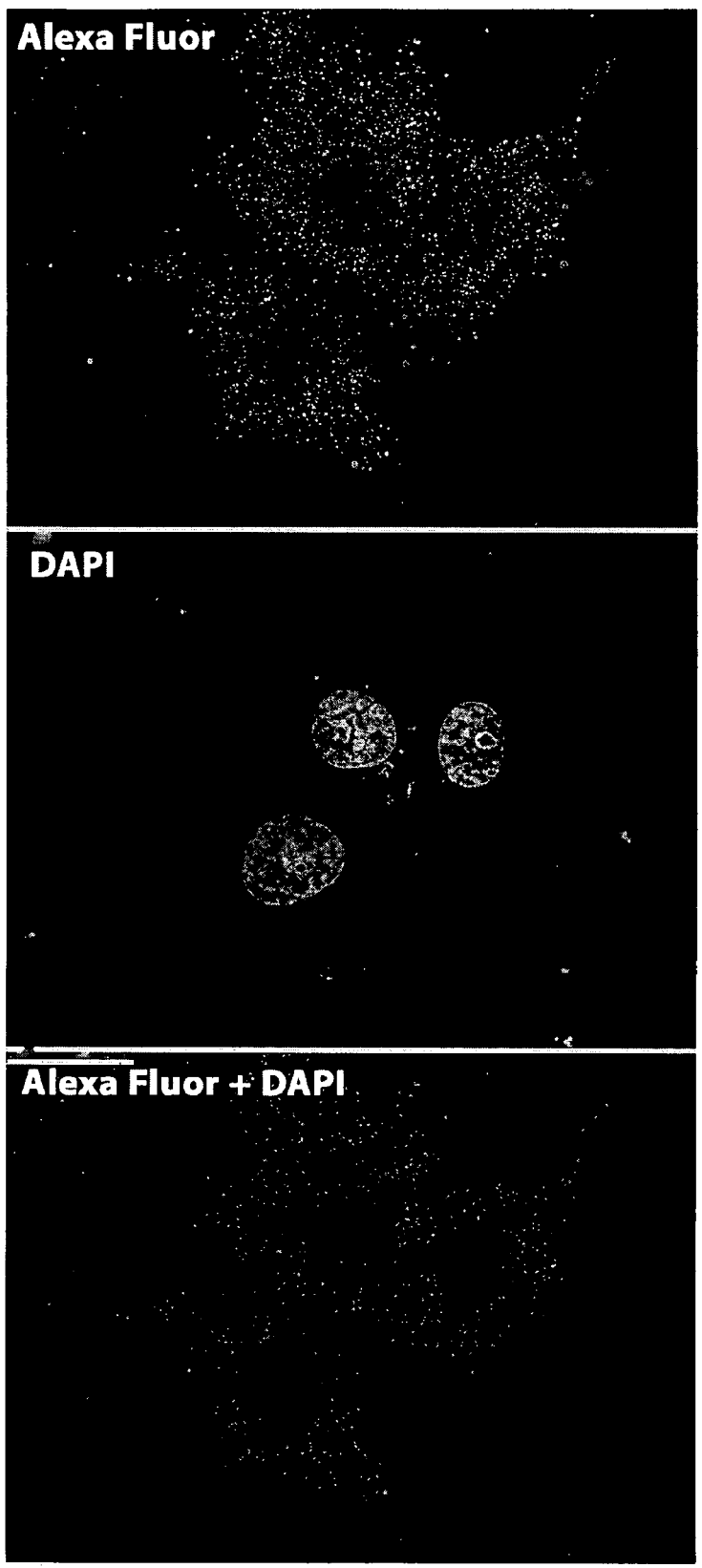
Figures 14A, 14B, 14C:
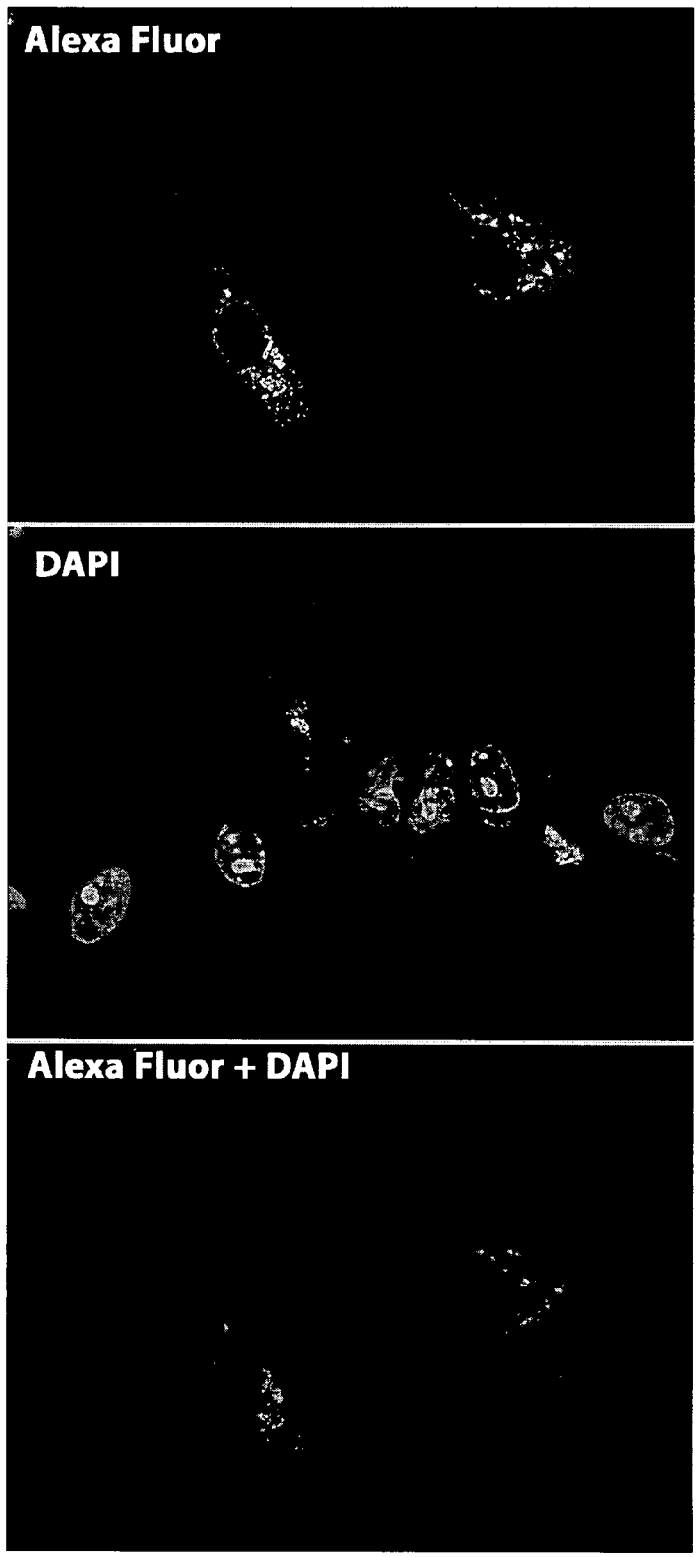

FIGS. 13 and 14 show activity of the endoplasmic reticulum localization signal of SEQ ID NO:1. COS7 African green monkey kidney cells were plated at 4,000 cells per square centimeter in a 24 well glass bottom plate (MatTek Cat. No. P24G-1.0-13-F) coated with poly-D-Lysine. The cells were grown in DMEM with 10% Fetal bovine serum at 37° C. for 24 hours. Plasmid DNA (0.4 ug) was introduced using CaPO4 (Invitrogen CaPO4 transfection kit), according to the manufacturer's protocol. After 24 hours, cells were washed twice with Ca2+/Mg2+-free PBS. The cells were fixed in ice-cold methanol (−20 C) for 5 minutes. Cells were then washed twice with PBS and incubated in a blocking solution of 8% bovine serum albumin (BSA) in PBS for 30 minutes. Primary antibody (mouse anti-FLAG M2 antibody from SigmaAldrich) was added at 2 µg/ml in a solution of PBS with 3% bovine serum albumin (BSA). After 2 h, the antibody was removed and the wells were rinsed 5×5 minutes with PBS. The last rinse was replaced with Goat anti-mouse secondary antibody conjugated to AlexaFluor 546 fluorescent dye. The antibody concentration was 200 ng/ml and was diluted in PBS with 3% BSA. After 45 minutes at room temperature and in the dark, the antibody was removed. Cells were rinsed three times in PBS, then incubated with 300 ng/mL DAPI containing PBS for 5 minutes. The cells were covered with Vectashield Mounting Medium (Vector Laboratories) before imaging.

The pictures in FIGS. 13 (vectorID-VVN8159) and 14 (vectorID-VVN8174) were generated using a Zeiss Axioobserver microscope fitted with an apotome structured light device and represent a magnification of 630× of a 500 nm slice through each group of cells. Pictures were taken with a set of red filters to visualize Alexa546 (excitation maximum 546 nm/emission maximum 608 nm) or blue filters (excitation maximum 365 nm/emission maximum 445 nm) to visualize the DAPI nuclear stain. The punctate and reticular patterns are indicative of ER staining, as is the exclusion of stain from the nucleus.

Figure 15:
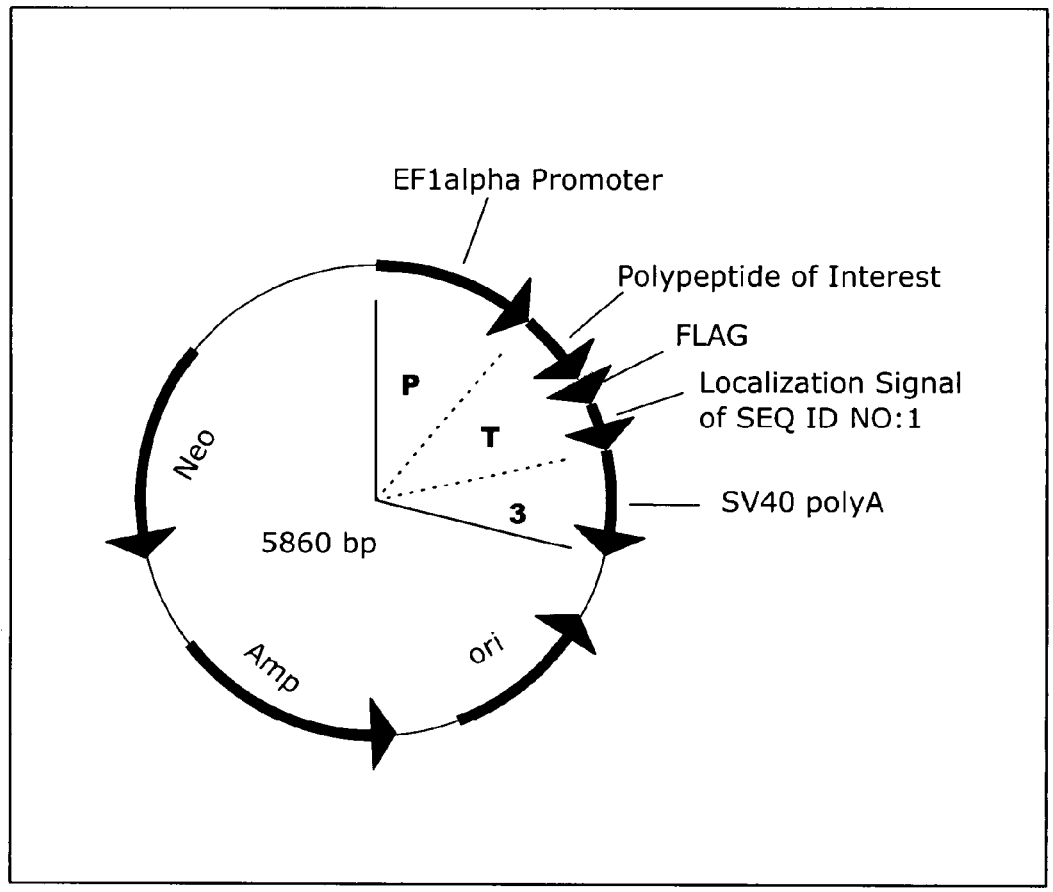

FIG. 15 shows a diagram of the vector used to transform the Cos7 cells of FIG. 13. Plasmid DNA vectors have the following architecture: VVN8159 contains a transgene with these components 5' to 3': PROMOTER (EFIalpha)-POLYPEPTIDE OF INTEREST (ERK1 decoy)-EPITOPE TAG (FLAG)-SEQ ID NO:1 (LOCALIZATION SIGNAL)-SV40PolyA. Abbreviations are as follows: Neo stands for neomycin resistance gene; Amp stands for ampicillin resistance gene; on stands for origin of replication; P stands for promoter domain; T stands for transcription domain; 3 stands for 3' regulatory domain.

Figure 16:
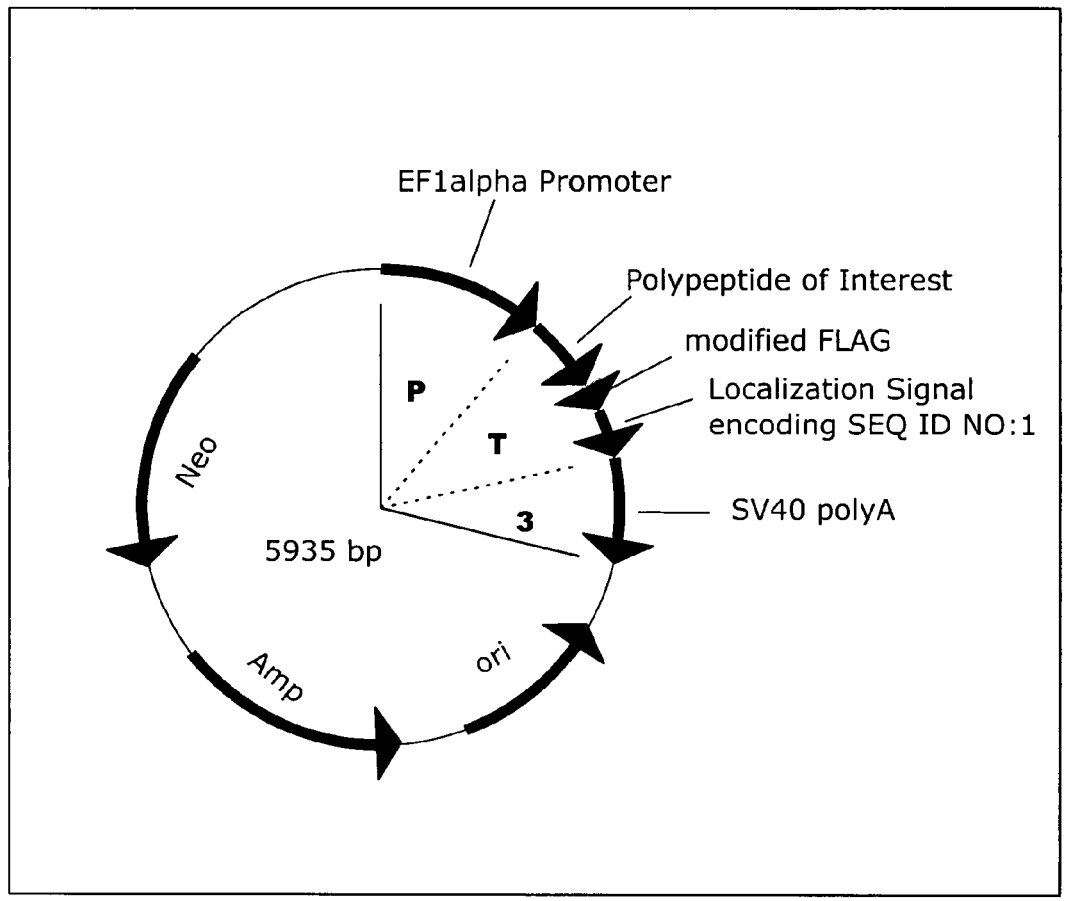

FIG. 16 shows a diagram of the vector used to transform the Cos7 cells of FIG. 14. Plasmid DNA vectors have the following architecture: VVN8174 contains a transgene with these components 5' to 3': PROMOTER (EFIalpha)-POLYPEPTIDE OF INTEREST (ERK1 decoy)-EPITOPE TAG (modified FLAG)-SEQ ID NO:1 (LOCALIZATION SIGNAL)-SV40PolyA. Abbreviations are as follows: Neo stands for neomycin resistance gene; Amp stands for ampicillin resistance gene; on stands for origin of replication; P stands for promoter domain; T stands for transcription domain; 3 stands for 3' regulatory domain.

BRIEF DESCRIPTION OF THE INVENTION

The invention relates to monomeric or multimeric endoplasmic reticulum localization signals. Various embodiments of the endoplasmic reticulum localization signals are represented in SEQ ID NOS:1-77. More specifically, the invention relates to monomeric or multimeric localization signals that comprise any one or more of SEQ ID NOS:39-77. Additionally, the invention relates to monomeric or multimeric polypeptide localization signals comprising one or more subsequences of SEQ ID NOS:17-38 or any portion thereof. Furthermore, the invention relates to monomeric or multimeric polypeptide localization signals with at least about 80%, 85%, 90%, 95%, 96%, 97%, 98% and 99% sequence identity to a polypeptide comprising one or more of SEQ ID NOS: 39-77 or any portion thereof. Furthermore, the invention relates to monomeric or multimeric polypeptide localization signals with at least about 80%, 85%, 90%, 95%, 96%, 97%, 98% and 99% sequence identity to a polypeptide comprising one or more subsequences of SEQ ID NOS:17-38.

Multimeric endoplasmic reticulum localization signals, which can be homomultimers or heteromultimers, are chimeric polypeptides composed of two or more monomers. An example of a monomeric localization signal is the polypeptide represented by SEQ ID NO:39. SEQ ID NO:39 is a selected subsequence of wild type full length SEQ ID NO:17. An example of a homomultimer is a polypeptide comprising a dimer or multimer of SEQ ID NO:39. An example of a heteromultimer is a polypeptide comprising SEQ ID NO:39 and one or more of SEQ ID NOS:40-77. There are numerous ways to combine SEQ ID NOS:39-77 into homomultimeric or heteromultimeric localization signals. Furthermore, there are numerous ways to combine additional subsequences of SEQ ID NOS:17-38 with each other and with SEQ ID NOS: 39-77 to make multimeric localization signals.

The localization signals of the invention optionally comprise spacer amino acids before, after or between monomers. SEQ ID NO:13 is an example of a heteromultimer with the structure X-S1-Y-S2-Y, where X and Y are selected from SEQ ID NOS:39-77 and S1 and S2 are amino acid spacers. This invention intends to capture all combinations of homomultimers and heteromultimers without limitation to the examples given above or below. In this description, use of the term localization signal encompasses monomeric, homomultimeric, and/or heteromultimeric polypeptide localization signals.

A monomeric ER localization signal is a polypeptide where at least a portion of the polypeptide is capable of functioning as an endoplasmic reticulum (ER) routing signal and/or as an endoplasmic reticulum retention signal. An ER routing signal functions to direct a polypeptide to the ER, while a retention signal functions to retain the polypeptide in the ER or to prevent secretion of ER-localized polypeptides.

A multimeric localization signal comprises two or more monomeric localization signals.

A homomultimeric localization signal is a multimer where each of the monomers is identical in amino acid sequence.

A heteromultimeric localization signal is a multimer where some of the monomers are not identical in amino acid sequence.

One embodiment of the invention is a monomeric localization signal containing a polypeptide at least 80% identical to one of SEQ ID NOS:39-69.

Another embodiment of the invention is a heteromultimeric localization signal containing polypeptides at least 80% identical to two or more of SEQ ID NOS:39-69.

Another embodiment of the invention is a heteromultimeric localization signal containing two or more of SEQ ID NOS:70-77.

Another embodiment of the invention is a heteromultimeric localization signal containing polypeptides at least 80% identical to two or more of SEQ ID NOS:39-77.

Another embodiment of the invention is a heteromultimeric localization signal containing a polypeptide at least 80% identical to one or more of SEQ ID NOS:39-69 adjacent to one or more of SEQ ID NOS:70-77.

Another embodiment of the invention is a heteromultimeric localization signal containing a polypeptide at least 80% identical to one or more subsequences of SEQ ID NOS:17-38 adjacent to one or more of SEQ ID NOS:70-77.

Another embodiment of the invention is a heteromultimeric localization signal containing polypeptides at least 80% identical to two or more subsequences of SEQ ID NOS:17-38.

The localization signals of the invention are optionally linked to additional molecules or amino acids that provide an epitope, a reporter, and/or an experimental or therapeutic molecule. The epitope and/or reporter and/or experimental molecule and/or therapeutic molecule may be the same molecule. The epitope and/or reporter and/or experimental molecule and/or therapeutic molecule may also be different molecules. Experimental or therapeutic molecules include but are not limited to proteins and polypeptides. In one embodiment, a localization signal for tethering a protein or macromolecule of interest to the cyoplasmic face of the ER is made where the localization signal is placed toward the C-terminus of the resultant fusion protein (FIGS. 7A, 7C, 7E, 7H). In another embodiment, a localization signal for tethering a protein or macromolecule of interest to the cyoplasmic face of the ER is made where the localization signal is placed toward the N-terminus of the resultant fusion protein (FIGS. 7B, 7D, 7F, 7G).

The invention also encompasses polynucleotides comprising nucleotide sequences encoding endoplasmic reticulum localization signals. The nucleic acids of the invention are optionally linked to additional nucleotide sequences encoding polypeptides with additional features, such as an epitope, a reporter, an experimental and/or therapeutic molecule. The polynucleotides are optionally flanked by nucleotide sequences comprising restriction endonuclease sites and other nucleotides needed for restriction endonuclease activity. The flanking sequences optionally provide unique cloning sites within a vector and optionally provide directionality of subsequence cloning. Further, the nucleic acids of the invention are optionally incorporated into vector polynucleotides. The localization signals of this invention have utility in compositions for research tools and/or therapeutics.

DETAILED DESCRIPTION OF THE INVENTION

The present invention relates to endoplasmic reticulum localization signals. Various embodiments of the localization signals are represented by SEQ ID NOS:1-77. Multimeric localization signals are chimeric polypeptides comprising two or more monomeric localization signals. An example of a monomeric localization signal is the polypeptide represented by SEQ ID NO:39. SEQ ID NO:39 is a selected subsequence of wild type full length SEQ ID NO:17. Another example of a monomeric localization signal is the polypeptide represented by SEQ ID NO:68. Each of SEQ ID NOS:39-77 represents an individual localization signal in monomeric form. SEQ ID NOS:39-69 are selected examples of subsequences of SEQ ID NOS:17-38, however, other subsequences of SEQ ID NOS:17-38 may also be utilized as monomeric localization signals. Monomeric subsequences of SEQ ID NOS:17-38 may be wild type subsequences. Additionally, monomeric subsequences of SEQ ID NOS:17-38 may have some amino acids different than the wild type parent. Furthermore, monomeric localization signals may have 80%, 85%, 90%, 95%, 96%, 97%, 98% or 99% sequence identity to a polypeptide comprising one or more of SEQ ID NOS:39-77. Furthermore, monomeric localization signals may have 80%, 85%, 90%, 95%, 96%, 97%, 98% and 99% sequence identity to a subsequence of SEQ ID NOS:17-38.

An example of a homomultimeric localization signal is a polypeptide comprising a dimer or multimer of SEQ ID NO:49. An example of a heteromultimeric localization signal is a polypeptide comprising SEQ ID NO:39 and one or more of SEQ ID NOS:40-77. There are numerous ways to combine SEQ ID NOS:39-77 into homomultimeric or heteromultimeric localization signals. Furthermore, there are numerous ways to combine additional subsequences of SEQ ID NOS:17-38 with each other and with SEQ ID NOS:39-77 to make multimeric localization signals.

Multimeric localization signals may comprise any two or more of SEQ ID NOS:39-77. A dimer or multimer of SEQ ID NO:66 is an example of a homomultimer. An example of a heteromultimer is a polypeptide comprising SEQ ID NO:77 and one or more of SEQ ID NOS:39-76. Another example of a heteromultimer is a polypeptide comprising SEQ ID NO:70 and one or more of SEQ ID NOS:39-69. Another example of a heteromultimer is a polypeptide comprising SEQ ID NO:72 and one or more of SEQ ID NOS:39-71. There are numerous ways to combine SEQ ID NOS:39-77 into homomultimeric or heteromultimeric localization signals. SEQ ID NOS:39-69 are selected examples of subsequences of SEQ ID NOS:17-38, however, additional subsequences, wild type or mutated, may be utilized to form multimeric localization signals. The instant invention is directed to all possible combinations of homomultimeric and heteromultimeric localization signals without limitation.

SEQ ID NOS:17-38 represent full length sequences of proteins that have endoplasmic reticulum localization activity. SEQ ID NOS:39-69 are subsequences of SEQ ID NOS:17-38 that are capable of conferring endoplasmic reticulum localization. SEQ ID NOS:70-77 are amino acid sequences that confer endoplasmic reticulum retention. Polypeptide subsequences that are identical to their wild type parent may be used as part of a localization signal, however in one embodiment some amino acids are mutated to another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, serine, threonine, or tyrosine. Mutation of amino acids may be performed for various reasons including, but not limited to, minimization of undesired biological activity, introduction or removal of secondary structure in the polypeptide; disruption of protein/protein interaction; modification of charge, hydrophobicity, or stability of the polypeptide; and introduction or removal of restriction sites in the nucleic acid encoding the polypeptide. As shown by SEQ ID NO:7, FIG. 12 and Example 4 below, the localization signals of the invention are capable of directing polypeptides of interest to the endoplasmic reticulum of eukaryotic cells.

In general, endoplasmic reticulum localization signals are built by identifying proteins that localize to the endoplasmic reticulum. Sometimes it is desirable to utilize wild type truncations as building blocks. However, it is sometimes desirable to modify one or more amino acids to enhance the localization. Other reasons for modifying the wild type sequences are to remove undesired characteristics, such as enzymatic activity or modulation of an endogenous cellular function. Monomeric building blocks may include an endoplasmic reticulum localization sequence as well as amino acids adjacent and contiguous on either side. Monomeric building blocks may therefore be any length provided the monomer confers endoplasmic localization, routing and/or retention. For example, the monomer may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the endoplasmic reticulum localization, routing or retention-conferring sequence.

For example, in one embodiment, the invention comprises an endoplasmic reticulum localization signal comprising at least one copy of a peptide selected from the group consisting of:
 a) a peptide at least 80%, 85%, 90%, 95%, 96%, 97%, 98% or 99% identical to a peptide comprising amino acid residues corresponding to amino acid residues 2338-2428 of the amino acid sequence of SEQ ID NO:17;
 b) a peptide at least 80%, 85%, 90%, 95%, 96%, 97%, 98% or 99% identical to a peptide comprising amino acid residues corresponding to amino acid residues 2341-2425 of the amino acid sequence of SEQ ID NO:17;
 c) a peptide at least 80%, 85%, 90%, 95%, 96%, 97%, 98% or 99% identical to a peptide comprising amino acid residues corresponding to amino acid residues 2349-2417 of the amino acid sequence of SEQ ID NO:17; and
 d) a peptide at least 80%, 85%, 90%, 95%, 96%, 97%, 98% or 99% identical to a peptide comprising amino acid residues corresponding to amino acid residues 2359-2407 of the amino acid sequence of SEQ ID NO:17.

In another embodiment, the invention comprises an endoplasmic reticulum localization signal comprising at least one copy of a peptide selected from SEQ ID NOS:70-77 and comprising at least one copy of a peptide selected from the group consisting of:
 a) a peptide at least 80%, 85%, 90%, 95%, 96%, 97%, 98% or 99% identical to a peptide comprising amino acid residues corresponding to amino acid residues 2338-2428 of the amino acid sequence of SEQ ID NO:17;
 b) a peptide at least 80%, 85%, 90%, 95%, 96%, 97%, 98% or 99% identical to a peptide comprising amino acid residues corresponding to amino acid residues 2341-2425 of the amino acid sequence of SEQ ID NO:17;
 c) a peptide at least 80%, 85%, 90%, 95%, 96%, 97%, 98% or 99% identical to a peptide comprising amino acid residues corresponding to amino acid residues 2349-2417 of the amino acid sequence of SEQ ID NO:17; and
 d) a peptide at least 80%, 85%, 90%, 95%, 96%, 97%, 98% or 99% identical to a peptide comprising amino acid residues corresponding to amino acid residues 2359-2407 of the amino acid sequence of SEQ ID NO:17.

As used herein, the terms "correspond(s) to" and "corresponding to," as they relate to sequence alignment, are intended to mean enumerated positions within a reference protein, e.g., IP3 Receptor (SEQ ID NO:17), and those positions that align with the positions on the reference protein. Thus, when the amino acid sequence of a subject peptide is aligned with the amino acid sequence of a reference peptide, e.g., SEQ ID NO:17, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers based on any putative or real polypeptide or protein that has endoplasmic reticulum localization, routing or retention activity, such as those identified by SEQ ID NOS:39-77. Furthermore, if the protein has more than one localization subsequence, then more than one monomer may be identified therein.

Another embodiment of the invention is a nucleic acid molecule comprising a polynucleotide sequence encoding at least one copy of a localization signal polypeptide.

Another embodiment of the invention is a nucleic acid molecule wherein the polynucleotide sequence encodes one or more copies of one or more localization signal polypeptides.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of an endoplasmic reticulum localization signal.

Another embodiment of the invention is a recombinant host cell comprising a vector comprising a nucleic acid molecule encoding at least one copy of an endoplasmic reticulum localization signal.

Another embodiment of the invention is a method of localizing a polypeptide to an endoplasmic reticulum subcellular compartment in a cell comprising linking a polypeptide open reading frame to a localization signal open reading frame to create a fusion protein coding sequence, and transfecting the fusion protein coding sequence into a host cell and culturing the transfected host cell under conditions suitable to produce at least one copy of the fusion protein.

Another embodiment of the invention is a method of delivering a therapeutic molecule to a subcellular location in a cell comprising transfecting a vector comprising a nucleic acid molecule encoding at least one copy of a localization signal linked to a therapeutic molecule into a host cell and culturing the transfected host cell under conditions suitable to produce at least one copy of the localization signal-containing therapeutic molecule.

The invention also relates to modified localization signals that are at least about 80%, 85%, 90% 95%, 96%, 97%, 98% or 99% identical to a reference polypeptide. A modified localization signal is used to mean a peptide that can be created by addition, deletion or substitution of one or more amino acids in the primary structure (amino acid sequence) of a localization signal protein or polypeptide. The terms "protein" and "polypeptide" and "peptide" are used interchangeably herein. The reference polypeptide is considered to be the wild type protein or a portion thereof. Thus, the reference polypeptide may be a protein whose sequence was previously modified over a wild type protein. The reference polypeptide may or may not be the wild type protein from a particular organism.

A polypeptide having an amino acid sequence at least, for example, about 95% identical to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., *Current Protocols in Protein Science*, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at the N- and C-terminal ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The multimeric localization signals of the invention optionally comprise spacer amino acids before, after, or between monomers (for example, FIGS. 2A-2C, 4A-4E). Additionally, the localization signals of the invention optionally comprise spacer amino acids before or after the localization signal (for example, FIGS. 2C, 4E, 5A, 5B, 5E, 5F, 6A, 6B, 6E, 6F, 7C, 7D, 7E, 7G, 8C, 8D, 8E, 8G and 8H). The length and composition of the spacer may vary. An example of a spacer is glycine, alanine, polyglycine, or polyalanine. In addition to providing space between monomers, spacers can be used for the purpose of engineering restriction sites in the encoding nucleic acid and can be used for modifying secondary structure of the polypeptide encoded. Specific examples of spacers used between monomers in SEQ ID NO:7 are the peptides EFGGGGG (SEQ ID NO: 79) and PGAG (SEQ ID NO: 78). In the instance of SEQ ID NO:7, the proline-containing spacer is intended to break an alpha helical secondary structure. At the C-terminal end of SEQ ID NO:7 is a five amino acid spacer with the sequence AAPAA (SEQ ID NO: 80). This particular spacer provides a linker to another module coding region such as a reporter, epitope or experimental or therapeutic polypeptide. The spacer amino acids may be any amino acid and are not limited to alanine, glycine and proline. The instant invention is directed to all combinations of homomultimers and heteromultimers, with or without spacers, and without limitation to the examples given above or below.

The localization signals of the invention are optionally linked to additional molecules or amino acids that provide an epitope, a reporter, and/or an experimental or therapeutic molecule (FIGS. 5A-5H, 6A-6H, 7A-7H, 8A-8H). Non-limiting examples of epitope are FLAG™ (Kodak; Rochester, N.Y.), HA (hemagluttinin), c-Myc and His6. Non-limiting examples of reporters are alkaline phosphatase, galactosidase, peroxidase, luciferase and fluorescent proteins. Non-limiting examples of experimental proteins are enzymes, enzyme binding partners, signalling factors, structural factors, and peptide ligands, metabolic binding factors, nucleic acid binding factors, and cellular binding factors. The epitopes, reporters and experimental or therapeutic molecules are given by way of example and without limitation. The epitope, reporter, experimental molecule and/or therapeutic molecule may be the same molecule. The epitope, reporter, experimental molecule and/or therapeutic molecule may also be different molecules.

Localization signals and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide synthesis methods known in the art. Recombinant techniques include insertion of localization signal encoding nucleic acids into expression vectors, wherein nucleic acid expression products are synthesized using cellular factors and processes.

Linkage of an epitope, reporter, experimental or therapeutic molecule to a localization signal can include covalent or enzymatic linkage. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The localization signals of the invention have utility as therapeutic targeting molecules. Pure peptides represent embodiments of conventional peptide therapeutics. However, polypeptides or proteins linked to localization signals have utility as subcellular tools or therapeutics. For example, polypeptides depicted generically in FIGS. 7A-7H represent localization signals with utility as subcellular tools or therapeutics. Localization signal-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 10A:
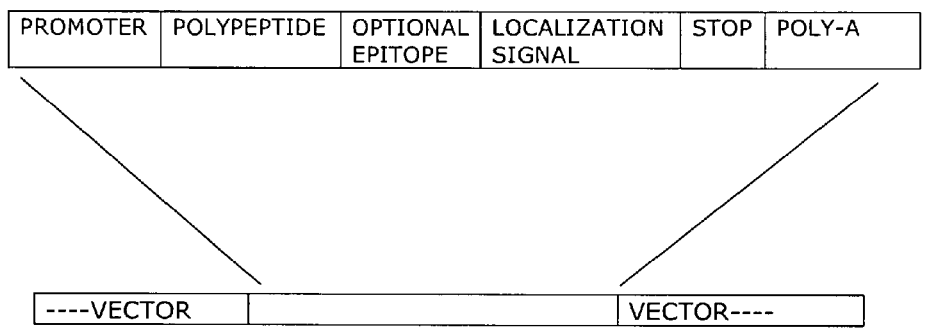
Figure 10B:
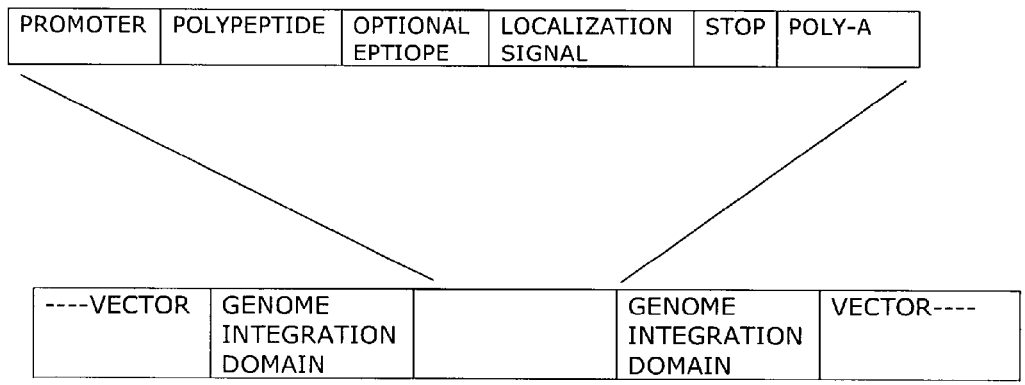
Figure 10C:
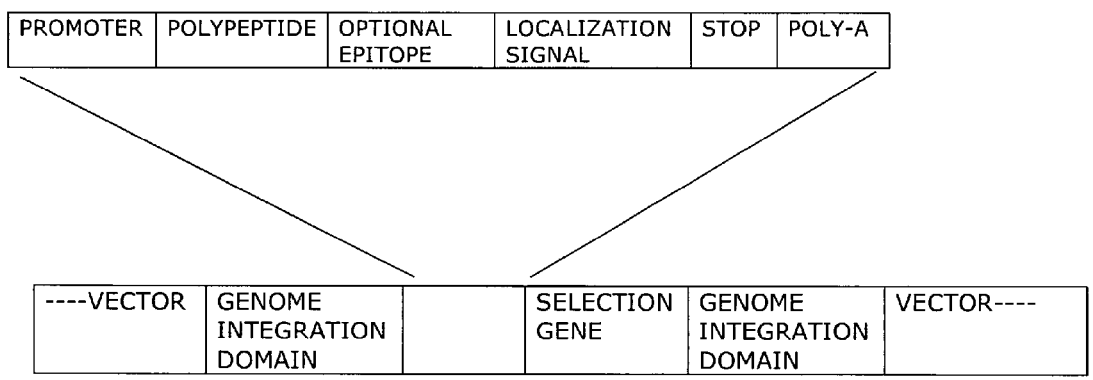

FIG. 10A shows a vector containing an endoplasmic reticulum localization signal and fluorescent protein gene construct, wherein the gene construct is releasable from the vector as a unit useful for generating transgenic animals. For example, the gene construct, or transgene, is released from the vector backbone by restriction endonuclease digestion. The released transgene is then injected into pronuclei of fertilized mouse eggs; or the transgene is used to transform embryonic stem cells. The vector containing a localization signal and reporter gene construct of FIG. 10A is also useful for transient transfection of the transgene, wherein the promoter and codons of the transgene are optimized for the host organism. The vector containing a gene construct of FIG. 10A is also useful for recombinant expression of polypeptides in fermentable organisms adaptable for small or large scale production, wherein the promoter and codons of the transgene are optimized for the fermentation host organism.

Figure 10D:
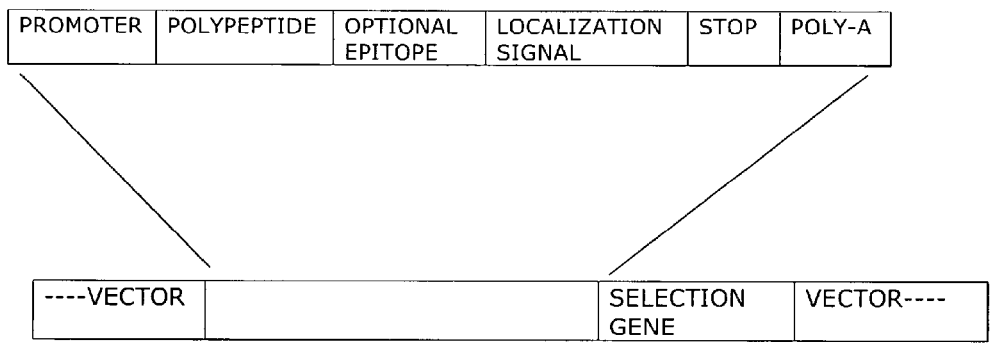

FIG. 10D shows a vector containing an endoplasmic reticulum localization signal gene construct useful for generating stable cell lines.

The invention also encompasses polynucleotides comprising nucleotide sequences encoding monomeric localization signals and multimeric localization signals. The polynucleotides of the invention are optionally linked to additional nucleotide sequences encoding epitopes, reporters and/or experimental or therapeutic molecules. Further, the nucleic acids of the invention are optionally incorporated into vector polynucleotides. The polynucleotides are optionally flanked by nucleotide sequences comprising restriction endonuclease sites and other nucleotides needed for restriction endonuclease activity. The flanking sequences optionally provide cloning sites within a vector. The restriction sites can include, but are not limited to, any of the commonly used sites in most commercially available cloning vectors. Non-limiting examples of such sites are those recognized by NsiI, ApaL1, MfeI, KpnI, BamHI, ClaI, EcoRI, EcoRV, SpeI, AflIII, NdeI, NheI, XbaI, XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Localization signals with or without epitopes, reporters, or experimental or therapeutic proteins are alternatively synthesized by recombinant techniques. Polynucleotide expression constructs are made containing desired components and inserted into an expression vector. The expression vector is then transfected into cells and the polypeptide products are expressed and isolated. Localization signals made according to recombinant DNA techniques have utility as research tools and/or subcellular therapeutic delivery agents.

The following is an example of how polynucleotides encoding localization signals are produced. Complimentary oligonucleotides encoding the localization signals and flanking sequences are synthesized and annealed. The resulting double-stranded DNA molecule is inserted into a cloning vector using techniques known in the art. When the localization signals are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promoter portion of the recombinant gene can be a constitutive promoter, a non-constitutive promoter, a tissue-specific promoter (constitutive or non-constitutive) or a selectively controlled promoter. Different selectively controlled promoters are controlled by different mechanisms. For example, a tetracycline-inducible promoter is activated to express a downstream coding sequence when the cell containing the promoter and other necessary cellular factors is treated with tetracycline. When tetracycline is removed, gene expression is subsequently reduced. Other inducible promoters are activated by other drugs or factors. RheoSwitch® is an inducible promoter system available from New England Biolabs (Ipswich, Mass.). Temperature sensitive promoters can also be used to increase or decrease gene expression. An embodiment of the invention comprises a localization signal containing gene construct whose expression is controlled by an inducible promoter. In one embodiment, the inducible promoter is tetracycline inducible.

Monomeric and multimeric ER localization signals and methods of making these localization signals are disclosed. Below are examples of methods of using ER localization signals. In general, localization signals linked to epitopes, reporters, and other desired proteins or molecules are delivered via adenovirus, lentivirus, adeno-associated virus, or other viral constructs that express protein product in a cell.

Methods

Cellular localization is tested using one or more of the following techniques.

Fluorescence microscopy is employed to determine spatial cellular localization. Fluorescence microscopy involves autofluorescence of fluorescent proteins fused to localization signals of the invention. Alternatively, fluorescence microscopy involves immunofluorescence of antibodies directed against epitopes fused to localization signals. Anti-epitope antibodies are either directly linked to a fluorochrome or are used in combination with a fluorescent secondary antibody.

Known cellular structures and locations are comparatively illustrated with well known and/or commercially available stains, dyes, antibodies and/or other reagents that identify cellular locations. Such reagents include but are not limited to: DAPI, Hoechst stains, acridine orange, Lysotracker (Invitrogen, Carlsbad, Calif.), ERtracker (Invitrogen, Carlsbad, Calif.), Golgitracker (Invitrogen, Carlsbad, Calif.), Mitotracker (Invitrogen, Carlsbad, Calif.), anti-CD25, anti-myc, anti-OSBP, anti-NSF, anti-transferrin receptor, anti-T-cell transferrin receptor, anti-AP2 alpha subunit, anti-clathrin heavy chain, anti-lamin, anti-histone, anti-histone deacetylase, anti-p53, phalloidin-coumarin, phalloidin-FITC, phalloidin-phycoerythrin, anti-oxysterol binding protein, anti-nem sensitive factor, anti-gm130, anti-lamp 1, anti-lamp2, acridine orange nonyl bromide, anti-tac antigen, anti-Na/K-ATPase, and anti-EGF receptor (antibody producing hybridomas available from ATCC).

Electron microscopy is employed to determine location at higher magnifications. Slides of cells expressing localization signals fused to epitopes are prepared using techniques known in the art. Anti-epitope antibodies are either directly linked to a gold label or in combination with a gold-labeled secondary antibody.

Immunoblotting is employed to determine quantitative expression levels and/or to biochemically corroborate microscopic observations. Immunoblotting or western blotting is performed on whole cell lysates and/or on cells that have been fractionated by density gradient centrifugation. Antibodies useful for fraction identification by western blot include but are not limited to anti-lamin, anti-histone, anti-histone deacetylase, anti-p53, anti-oxysterol binding protein, anti-nem sensitive factor, anti-gm130, anti-lamp1, anti-lamp2, anti-tac antigen, anti-caveolin-1 and anti-EGF receptor.

Epitopes for use in localization signal fusion proteins include hemagglutinin (HA), FLAG and Myc, among others. Specifically, localization signals fused to an epitope are expressed in Hela, HCTZ 16, HT1080, HCN1a, HCN2, SHSY5Y, ARPE19-HPV16 p5, U87-MG, C2Bbe1, HEK293, COS1, COS7, MDCK, C2C12, Sol8, P19, 10T1/2 and NIH3T3 (available from the ATCC). Anti-hemagluttinin antibodies and fluorescent secondary antibody are then employed to visualize location using standard methods such as those described in Giepmans et al. 2006 Science 312:217-24, incorporated by reference herein. For electron microscopy, methods such as those described in Ukimura et al. 1997 Am J. Pathol. 150:2061-2074 (incorporated by reference herein) are employed.

Alternatively, localization signals fused to a fluorescent protein are expressed in Hela, HCT116, HT 1080, HCN1a, HCN2, SHSY5Y, ARPE19-HPV16 p5, U87-MG, C2Bbe1, HEK293, COS 1, COS7, MDCK, C2C12, Sol8, P19, 10T1/2 and NIH3T3 (available from the ATCC). Location is visualized using standard methods such as those described in Giepmans et al. 2006 Science 312:217-24, incorporated by reference herein.

For immunoblot analysis, cellular fractions are obtained by taking cells expressing localization signals fused to a hemagluttinin epitope, and lightly homogenizing them, for example, in a Dounce homogenizer. Homogenized cells are then subjected to density gradient centrifugation as is known in the art and described in Current Methods in Cell Biology (Volume 1, Chapter 3, pages 3.0.1-3.11.22, Bonafacino et al. editors) (incorporated by reference herein). Fractions from the density gradient centrifugation are then electrophoresed on an acrylamide gel and subsequently transfered to a membrane electrophoretically. The membrane is then probed with appropriate anti-hemagluttinin antibodies and/or antibodies to known proteins. By comparing the gel lanes showing an anti-hemagglutinnin signal to gel lanes showing antibody signals of known proteins, cellular location of a localization signal of the invention is determined biochemically.

EXAMPLES

Example 1

A polypeptide comprising a multimeric endoplasmic reticulum localization signal and an epitope is synthesized. The structure of such a polypeptide is generically represented by FIG. 5C. The polypeptide is synthesized on an automated peptide synthesizer or is recombinantly expressed and purified. Purified polypeptide is solubilized in media and added to cells. Verification is performed by visualization of antibody binding to the epitope.

Example 2

A transgene is constructed using a human cytomegalovirus (CMV) promoter to direct expression of a fusion protein comprising SEQ ID NO:64, SEQ ID NO:69, and SEQ ID NO:72 (LOCALIZATION SIGNAL) and green fluorescent protein (REPORTER). Such a transgene is generically represented by FIG. 9G. The transgene is transfected into cells for transient expression. Verification of expression and location is performed by visualization of the fluorescent protein by confocal microscopy.

Example 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode a kinase inhibitor, a FLAG epitope, and an endoplasmic reticulum localization signal. The localization signal is a monomeric, homomultimeric, or heteromultimeric localization signal as described herein. Nucleotide sequences encoding a FLAG epitope are placed downstream of nucleotide sequences encoding the kinase inhibitor. Finally, nucleotide sequences encoding the localization signal are placed downstream of those encoding the FLAG epitope. The assembled gene expression unit is subsequently subcloned into an expression vector, such as that shown in FIG. 10A, and used to transiently transfect cells. Verification is performed by microscopic visualization of the epitope immunoreactivity at the endoplasmic reticulum.

Example 4

Subcellularly localized chloramphenicol acetyltransferase fragment was demonstrated in the endoplasmic reticulum of Cos7 cells using a transgene construct containing an endoplasmic reticulum localization signal, a c-Myc eptitope, and a chloramphenicol acetyltransferase fragment (non-enzymatic) was made. The expression unit contains nucleotides that encode an endoplasmic reticulum localization signal SEQ ID NO:7 (LOCALIZATION SIGNAL), a c-Myc epitope (EPITOPE), and a fragment of chloramphenicol acetyltransferase (POLYPEPTIDE OF INTEREST). This expression unit is subsequently subcloned into a vector between a CMV promoter and an SV40 polyadenylation signal (FIG. 11). The completed transgene-containing expression vector was then used to transfect Cos7 cells. FIG. 12 illustrates the subcellular colocation (yellow) of the c-Myc epitope (green) with calreticulin (red). In the presence of the localization signal, chloramphenicol acetyltransferase fragment is located at the endoplasmic reticulum.

Additionally, subcellularly localized polypeptide of interest was demonstrated in the endoplasmic reticulum of Cos7 cells using a transgene construct containing an endoplasmic reticulum localization signal, a FLAG (or modified FLAG) eptitope, and an ERK decoy polypeptide of interest. The expression unit of the transgene contains nucleotides that encode an ERK decoy (POLYPEPTIDE OF INTEREST), a FLAG (or modified FLAG) tag (EPITOPE), and endoplasmic reticulum localization signal SEQ ID NO:1 (LOCALIZATION SIGNAL). This expression unit was subsequently subcloned into a vector between an EF1alpha promoter and an SV40 polyadenylation signal (FIG. 15, FIG. 16). The completed transgene-containing expression vector was then used to transfect Cos7 cells. FIGS. 13 and 14 illustrate the subcellular location (red) of the FLAG (or modified FLAG) epitope.

Example 5

Fluorescent protein localization is demonstrated in vivo by making a transgene construct used to generate mice expressing a fusion protein targeted to the endoplasmic reticulum. The transgene construct is shown generically in FIG. 10B. The expression unit contains nucleotides that encode a dimer of SEQ ID NO:49 (LOCALIZATION SIGNAL) and green fluorescent protein (POLYPEPTIDE). This expression unit is subsequently subcloned into a vector between nucleotide sequences including a mammalian promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 4 harbor the transgene in their genomes.

Test 2: Tissues are prepared for microscopic analysis. This experiment demonstrates the transgene is expressed in tissues of transgenic mice because green fluorescent protein is visualized in transgenic tissues but not in non-transgenic tissues.

These examples demonstrate delivery of molecules to a localized region of a cell for therapeutic or experimental purposes. The purified polypeptide localization signals linked to therapeutics can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the localization signals permit incorporation into a vector designed to deliver and express a gene product in a subcellular compartment. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells. The invention encompasses transgenes comprising localization signals and non-human transgenic organisms harboring these transgenes. The transgenes may be under the control of inducible promoters or tissue-specific promoters.

Disclosed are endoplasmic localization signals and methods of making and using these localization signals. The localization signals are synthesized chemically or recombinantly and are utilized as research tools or as therapeutic delivery agents. The invention includes linking molecules to cellular localization signals for subcellular therapeutics.

What is claimed is:

1. An isolated polypeptide localization signal comprising:
   (a) an amino acid sequence at least 90% identical to SEQ ID NO: 64; and
   (b) an amino acid sequence at least 90% identical to SEQ ID NO: 69; and
   (c) the amino acid sequence of SEQ ID NO: 72.

2. The isolated polypeptide localization signal of claim 1, wherein (a) is SEQ ID NO: 64 and (b) is SEQ ID NO: 69.

3. The isolated polypeptide localization signal of claim 1 or claim 2, wherein said polypeptide localization signal is linked to a polypeptide of interest, a macromolecule, or a therapeutic molecule.

4. The isolated polypeptide localization signal of claim 1, further comprising linker amino acids before or after the amino acid sequence that is at least 90% identical to SEQ ID NO: 64, between the amino acid sequence that is at least 90% identical to SEQ ID NO: 64 and the amino acid sequence of SEQ ID NO: 69, before or after the amino acid sequence of SEQ ID NO: 69, between the amino acid sequence that is at least 90% identical to SEQ ID NO: 69 and the amino acid sequence of SEQ ID NO: 72, or before or after the amino acid sequence of SEQ ID NO: 72.

5. The isolated polypeptide localization signal of claim 1 or claim 2, wherein said polypeptide is linked to an epitope tag, or a reporter.

6. An isolated polynucleotide encoding the isolated polypeptide localization signal of claim 1 or claim 2.

7. The isolated polynucleotide of 6, wherein said polypeptide localization signal further comprises linker amino acids before or after the amino acid sequence that is at least 90% identical to SEQ ID NO: 64, between the amino acid sequence that is at least 90% identical to SEQ ID NO: 64 and the amino acid sequence of SEQ ID NO: 69, before or after the amino acid sequence of SEQ ID NO: 69, between the amino acid sequence that is at least 90% identical to SEQ ID NO: 69 and the amino acid sequence of SEQ ID NO: 72, or before or after the amino acid sequence of SEQ ID NO: 72.

8. The isolated polynucleotide claim 1 or claim 2, wherein said polypeptide localization signal is linked to an epitope tag, or a reporter.

9. A vector comprising the polynucleotide of claim 6.

10. An isolated host cell comprising the vector of claim 9.

11. The vector of claim 9, further comprising an inducible promoter, and wherein said polynucleotide is operably linked to said inducible promoter.

12. The vector of claim 9, further comprising a tissue-specific promoter, and wherein said polynucleotide is operably linked to said tissue-specific promoter.

13. An isolated host cell comprising the vector of claim 9.

14. A method of localizing a polypeptide of interest to an endoplasmic reticulum compartment in a cell, said method comprising:
- (a) linking a polynucleotide sequence encoding a polypeptide open reading frame to the isolated polynucleotide of claim 6 to create a fusion protein coding sequence,
- (b) transfecting the fusion protein coding sequence into a host cell, and
- (c) culturing the transfected host cell under conditions suitable to produce the fusion protein.

* * * * *

UNITED STATES PATENT AND TRADEMARK OFFICE
CERTIFICATE OF CORRECTION

PATENT NO. : 8,703,905 B2  Page 1 of 1
APPLICATION NO. : 13/369649
DATED : April 22, 2014
INVENTOR(S) : Thomas D. Reed It is certified that error appears in the above-identified patent and that said Letters Patent is hereby corrected as shown below:

In the Claims

Claim 8, Column 115
Line 9, "polynucleotide" should be replaced with --polypeptide--.

Claim 13, Column 115
Line 20, "vector of claim 9" should be replaced with --polynucleotide of claim 6--.

Signed and Sealed this
Sixteenth Day of December, 2014

Michelle K. Lee
*Deputy Director of the United States Patent and Trademark Office*

SEQUENCE LISTING

<160> NUMBER OF SEQ ID NOS: 80

<210> SEQ ID NO 1
<211> LENGTH: 79
<212> TYPE: PRT
<213> ORGANISM: artificial sequence
<220> FEATURE:
<223> OTHER INFORMATION: Synthetic

<400> SEQUENCE: 1

Asp Arg Leu Ile Ser His Cys Gly Pro Val Thr Gly Tyr Ile Phe Ala
1               5                   10                  15

Leu Leu Ala Val Leu Ser Tyr Leu Phe Leu Ile Phe Leu Gln Trp Met
            20                  25                  30

Thr Pro Asp Ser Val Ile Asp Val Ala Ile Asp Ala Thr Gly Pro Arg
        35                  40                  45

Arg Ala Trp Thr His Gln Trp Pro Arg Asp Glu Phe Cys Val Leu Phe
    50                  55                  60

Pro Gly Ala Gly Cys Val Leu Phe Ala Ala Ala Lys Asp Glu Leu
65                  70                  75

<210> SEQ ID NO 2
<211> LENGTH: 237
<212> TYPE: DNA
<213> ORGANISM: artificial sequence
<220> FEATURE:
<223> OTHER INFORMATION: Synthetic

<400> SEQUENCE: 2
gacaggctga tcagccactg cggccccgtg accggctaca tcttcgccct gctggccgtg        60
ctgagctacc tgttcctgat cttcctgcag tggatgaccc ccgacagcgt gatcgacgtg       120
gccatcgacg ccaccggccc caggagggcc tggacccacc agtggcccag ggacgagttc       180
tgcgtgctgt tccccggcgc cggctgcgtg ctgttcgccg ccgccaagga cgagctg          237

<210> SEQ ID NO 3
<211> LENGTH: 240
<212> TYPE: DNA
<213> ORGANISM: artificial sequence
<220> FEATURE:
<223> OTHER INFORMATION: Synthetic

```
<400> SEQUENCE: 3
gacagactca tcagtcactg tgggccagtg accggctaca tctttgccct gctcgctgtc      60
ctgagctatt tgttcctgat cttttttgcag tggatgactc ctgattctgt tattgacgta    120
gctatagatg ccactgggcc acggagagcc tggactcacc agtggcccag ggacgaattc     180
tgcgttctgt tccctggtgc ggggtgtgtc ctgttcgcag ccgcgaaaga cgaactttga     240

<210> SEQ ID NO 4
<211> LENGTH: 252
<212> TYPE: DNA
<213> ORGANISM: artificial sequence
<220> FEATURE:
<223> OTHER INFORMATION: Synthetic

<400> SEQUENCE: 4
catatggaca gactcatcag tcactgtggg ccagtgaccg gctacatctt tgccctgctc      60
gctgtcctga gctatttgtt cctgatcttt ttgcagtgga tgactcctga ttctgttatt    120
gacgtagcta tagatgccac tgggccacgg agagcctgga ctcaccagtg gcccagggac    180
gaattctgcg ttctgttccc tggtgcgggg tgtgtcctgt tcgcagccgc gaaagacgaa    240
ctttgaatgc at                                                        252

<210> SEQ ID NO 5
<211> LENGTH: 240
<212> TYPE: DNA
<213> ORGANISM: artificial sequence
<220> FEATURE:
<223> OTHER INFORMATION: Synthetic

<400> SEQUENCE: 5
gacagactca tcagtcactg tgggccagtg accggctaca tctttgccct gctcgctgtc      60
ctgagctatt tgttcctgat cttttttgcag tggatgactc ctgattctgt tattgacgta    120
gctatagatg ccactgggcc acggagagcc tggactcacc agtggcccag ggacgagttc     180
tgcgttctgt tccctggtgc ggggtgtgtc ctgttcgcag ccgcgaaaga cgaactttga     240

<210> SEQ ID NO 6
<211> LENGTH: 252
<212> TYPE: DNA
<213> ORGANISM: artificial sequence
<220> FEATURE:
<223> OTHER INFORMATION: Synthetic

<400> SEQUENCE: 6
catatggaca gactcatcag tcactgtggg ccagtgaccg gctacatctt tgccctgctc      60
gctgtcctga gctatttgtt cctgatcttt ttgcagtgga tgactcctga ttctgttatt    120
gacgtagcta tagatgccac tgggccacgg agagcctgga ctcaccagtg gcccagggac    180
gagttctgcg ttctgttccc tggtgcgggg tgtgtcctgt tcgcagccgc gaaagacgaa    240
ctttgaatgc at                                                        252

<210> SEQ ID NO 7
<211> LENGTH: 58
<212> TYPE: PRT
<213> ORGANISM: artificial sequence
<220> FEATURE:
<223> OTHER INFORMATION: Synthetic
```

<400> SEQUENCE: 7

Met Gly Val Lys Thr Val Leu Leu Ile Val Gly Val Leu Gly Ala
1               5                   10                  15

Tyr Tyr Val Tyr Thr Pro Leu Pro Asp Asn Ile Glu Glu Pro Trp Arg
            20                  25                  30

Leu Leu Glu Phe Gly Gly Gly Gly Cys Val Leu Phe Pro Gly Ala
        35                  40                  45

Gly Cys Val Leu Phe Ala Ala Pro Ala Ala
        50                  55

<210> SEQ ID NO 8
<211> LENGTH: 174
<212> TYPE: DNA
<213> ORGANISM: artificial sequence
<220> FEATURE:
<223> OTHER INFORMATION: Synthetic

<400> SEQUENCE: 8
atgggcgtga agaccgtgct gctgctgatc gtgggcgtgc tgggcgccta ctacgtgtac      60
acccccctgc ccgacaacat cgaggagccc tggaggctgc tggagttcgg cggcggcggc     120
ggctgcgtgc tgttccccgg cgccggctgc gtgctgttcg ccgcccccgc cgcc           174

<210> SEQ ID NO 9
<211> LENGTH: 174
<212> TYPE: DNA
<213> ORGANISM: artificial sequence
<220> FEATURE:
<223> OTHER INFORMATION: Synthetic

<400> SEQUENCE: 9
atgggagtaa agaccgttct cttgttgatc gtcggagttc tgggagccta ttacgtctac      60
accccactcc ccgacaacat tgaagaaccc tggagactgc tcgaattcgg cggggcgga     120 gggtgcgtgc ttttccctgg tgccggatgc gtcctgttcg ccgctccagc tgct           174

<210> SEQ ID NO 10
<211> LENGTH: 195
<212> TYPE: DNA
<213> ORGANISM: artificial sequence
<220> FEATURE:
<223> OTHER INFORMATION: Synthetic

<400> SEQUENCE: 10
ggcgccggag ccaccatggg agtaaagacc gttctcttgt tgatcgtcgg agttctggga      60
gcctattacg tctacacccc actccccgac aacattgaag aacctggag actgctcgaa     120 ttcggcgggg cggagggtg cgtgcttttc cctggtgccg gatgcgtcct gttcgccgct     180
ccagctgcta tgcat                                                      195

<210> SEQ ID NO 11
<211> LENGTH: 174
<212> TYPE: DNA
<213> ORGANISM: artificial sequence
<220> FEATURE:
<223> OTHER INFORMATION: Synthetic

<400> SEQUENCE: 11
atgggagtaa agaccgttct cttgttgatc gtcggagttc tgggagccta ttacgtctac      60
accccactcc ccgacaacat tgaagaaccc tggagactgc tcgagttcgg cggggcgga     120 gggtgcgtgc ttttccctgg tgccggatgc gtcctgttcg ccgctccagc tgct           174

```
<210> SEQ ID NO 12
<211> LENGTH: 195
<212> TYPE: DNA
<213> ORGANISM: artificial sequence
<220> FEATURE:
<223> OTHER INFORMATION: Synthetic

<400> SEQUENCE: 12
ggcgccggag ccaccatggg agtaaagacc gttctcttgt tgatcgtcgg agttctggga      60
gcctattacg tctacacccc actccccgac aacattgaag aaccctggag actgctcgag     120
ttcggcgggg gcggagggtg cgtgcttttc cctggtgccg gatgcgtcct gttcgccgct     180
ccagctgcta tgcat                                                      195

<210> SEQ ID NO 13
<211> LENGTH: 53
<212> TYPE: PRT
<213> ORGANISM: artificial sequence
<220> FEATURE:
<223> OTHER INFORMATION: Synthetic

<400> SEQUENCE: 13

Met Gly Val Lys Thr Val Leu Leu Leu Ile Val Gly Val Leu Gly Ala
1               5                   10                  15

Tyr Tyr Val Tyr Thr Pro Leu Pro Asp Asn Ile Glu Glu Pro Trp Arg
            20                  25                  30

Leu Leu Glu Phe Gly Gly Gly Gly Gly Cys Val Leu Phe Pro Gly Ala
        35                  40                  45

Gly Cys Val Leu Phe
    50

<210> SEQ ID NO 14
<211> LENGTH: 159
<212> TYPE: DNA
<213> ORGANISM: artificial sequence
<220> FEATURE:
<223> OTHER INFORMATION: Synthetic

<400> SEQUENCE: 14
atgggcgtga agaccgtgct gctgctgatc gtgggcgtgc tgggcgccta ctacgtgtac      60 accccccctgc cgacaacat cgaggagccc tggaggctgc tggagttcgg cggcggcggc     120
ggctgcgtgc tgttccccgg cgccggctgc gtgctgttc                            159

<210> SEQ ID NO 15
<211> LENGTH: 159
<212> TYPE: DNA
<213> ORGANISM: artificial sequence
<220> FEATURE:
<223> OTHER INFORMATION: Synthetic

<400> SEQUENCE: 15
atgggagtaa agaccgttct cttgttgatc gtcggagttc tgggagccta ttacgtctac      60
accccactcc ccgacaacat tgaagaaccc tggagactgc tcgaattcgg cggggcgga     120 gggtgcgtgc ttttccctgg tgccggatgc gtcctgttc                            159

<210> SEQ ID NO 16
<211> LENGTH: 180
<212> TYPE: DNA
<213> ORGANISM: artificial sequence
<220> FEATURE:
<223> OTHER INFORMATION: Synthetic

<400> SEQUENCE: 16
```

```
ggcgccggag ccaccatggg agtaaagacc gttctcttgt tgatcgtcgg agttctggga    60
gcctattacg tctacacccc actccccgac aacattgaag aaccctggag actgctcgaa   120
ttcggcgggg gcggagggtg cgtgctttc cctggtgccg gatgcgtcct gttcatgcat   180
```

<210> SEQ ID NO 17
<211> LENGTH: 2749
<212> TYPE: PRT
<213> ORGANISM: Rattus sp.

<400> SEQUENCE: 17

| | | | | | | | | | | | | | | |
|---|---|---|---|---|---|---|---|---|---|---|---|---|---|---|
| Met | Ser | Asp | Lys | Met | Ser | Ser | Phe | Leu | His | Ile | Gly | Asp | Ile | Cys | Ser |
| 1 | | | | 5 | | | | | 10 | | | | | 15 | |
| Leu | Tyr | Ala | Glu | Gly | Ser | Thr | Asn | Gly | Phe | Ile | Ser | Thr | Leu | Gly | Leu |
| | | | 20 | | | | | 25 | | | | | 30 | | |
| Val | Asp | Asp | Arg | Cys | Val | Val | Gln | Pro | Glu | Ala | Gly | Asp | Leu | Asn | Asn |
| | | | 35 | | | | 40 | | | | | 45 | | | |
| Pro | Pro | Lys | Lys | Phe | Arg | Asp | Cys | Leu | Phe | Lys | Leu | Cys | Pro | Met | Asn |
| | 50 | | | | | 55 | | | | | 60 | | | | |
| Arg | Tyr | Ser | Ala | Gln | Lys | Gln | Phe | Trp | Lys | Ala | Ala | Lys | Pro | Gly | Ala |
| 65 | | | | | 70 | | | | | 75 | | | | | 80 |
| Asn | Ser | Thr | Thr | Asp | Ala | Val | Leu | Leu | Asn | Lys | Leu | His | His | Ala | Ala |
| | | | | 85 | | | | | 90 | | | | | 95 | |
| Asp | Leu | Glu | Lys | Lys | Gln | Asn | Glu | Thr | Glu | Asn | Arg | Lys | Leu | Leu | Gly |
| | | | 100 | | | | | 105 | | | | | 110 | | |
| Thr | Val | Ile | Gln | Tyr | Gly | Asn | Val | Ile | Gln | Leu | Leu | His | Leu | Lys | Ser |
| | | | 115 | | | | | 120 | | | | | 125 | | |
| Asn | Lys | Tyr | Leu | Thr | Val | Asn | Lys | Arg | Leu | Pro | Ala | Leu | Leu | Glu | Lys |
| | 130 | | | | | 135 | | | | | 140 | | | | |
| Asn | Ala | Met | Arg | Val | Thr | Leu | Asp | Glu | Ala | Gly | Asn | Glu | Gly | Ser | Trp |
| 145 | | | | | 150 | | | | | 155 | | | | | 160 |
| Phe | Tyr | Ile | Gln | Pro | Phe | Tyr | Lys | Leu | Arg | Ser | Ile | Gly | Asp | Ser | Val |
| | | | | 165 | | | | | 170 | | | | | 175 | |
| Val | Ile | Gly | Asp | Lys | Val | Val | Leu | Asn | Pro | Val | Asn | Ala | Gly | Gln | Pro |
| | | | 180 | | | | | 185 | | | | | 190 | | |
| Leu | His | Ala | Ser | Ser | His | Gln | Leu | Val | Asp | Asn | Pro | Gly | Cys | Asn | Glu |
| | | | 195 | | | | | 200 | | | | | 205 | | |
| Val | Asn | Ser | Val | Asn | Cys | Asn | Thr | Ser | Trp | Lys | Ile | Val | Leu | Phe | Met |
| | 210 | | | | | 215 | | | | | 220 | | | | |
| Lys | Trp | Ser | Asp | Asn | Lys | Asp | Asp | Ile | Leu | Lys | Gly | Gly | Asp | Val | Val |
| 225 | | | | | 230 | | | | | 235 | | | | | 240 |
| Arg | Leu | Phe | His | Ala | Glu | Gln | Glu | Lys | Phe | Leu | Thr | Cys | Asp | Glu | His |
| | | | | 245 | | | | | 250 | | | | | 255 | |
| Arg | Lys | Lys | Gln | His | Val | Phe | Leu | Arg | Thr | Thr | Gly | Arg | Gln | Ser | Ala |
| | | | 260 | | | | | 265 | | | | | 270 | | |
| Thr | Ser | Ala | Thr | Ser | Ser | Lys | Ala | Leu | Trp | Glu | Val | Glu | Val | Val | Gln |
| | | 275 | | | | | 280 | | | | | 285 | | | |
| His | Asp | Pro | Cys | Arg | Gly | Gly | Ala | Gly | Tyr | Trp | Asn | Ser | Leu | Phe | Arg |
| | 290 | | | | | 295 | | | | | 300 | | | | |
| Phe | Lys | His | Leu | Ala | Thr | Gly | His | Tyr | Leu | Ala | Ala | Glu | Val | Asp | Pro |
| 305 | | | | | 310 | | | | | 315 | | | | | 320 |
| Asp | Phe | Glu | Glu | Glu | Cys | Leu | Glu | Phe | Gln | Pro | Ser | Val | Asp | Pro | Asp |
| | | | | 325 | | | | | 330 | | | | | 335 | |
| Gln | Asp | Ala | Ser | Arg | Ser | Arg | Leu | Arg | Asn | Ala | Gln | Glu | Lys | Met | Val |
| | | | 340 | | | | | 345 | | | | | 350 | | |

```
Tyr Ser Leu Val Ser Val Pro Glu Gly Asn Asp Ile Ser Ser Ile Phe
            355                 360                 365

Glu Leu Asp Pro Thr Thr Leu Arg Gly Gly Asp Ser Leu Val Pro Arg
        370                 375                 380

Asn Ser Tyr Val Arg Leu Arg His Leu Cys Thr Asn Thr Trp Val His
385                 390                 395                 400

Ser Thr Asn Ile Pro Ile Asp Lys Glu Glu Lys Pro Val Met Leu
                405                 410                 415

Lys Ile Gly Thr Ser Pro Leu Lys Glu Asp Lys Glu Ala Phe Ala Ile
            420                 425                 430

Val Pro Val Ser Pro Ala Glu Val Arg Asp Leu Asp Phe Ala Asn Asp
        435                 440                 445

Ala Ser Lys Val Leu Gly Ser Ile Ala Gly Lys Leu Glu Lys Gly Thr
    450                 455                 460

Ile Thr Gln Asn Glu Arg Arg Ser Val Thr Lys Leu Leu Glu Asp Leu
465                 470                 475                 480

Val Tyr Phe Val Thr Gly Gly Thr Asn Ser Gly Gln Asp Val Leu Glu
                485                 490                 495

Val Val Phe Ser Lys Pro Asn Arg Glu Arg Gln Lys Leu Met Arg Glu
            500                 505                 510

Gln Asn Ile Leu Lys Gln Ile Phe Lys Leu Leu Gln Ala Pro Phe Thr
        515                 520                 525

Asp Cys Gly Asp Gly Pro Met Leu Arg Leu Glu Glu Leu Gly Asp Gln
    530                 535                 540

Arg His Ala Pro Phe Arg His Ile Cys Arg Leu Cys Tyr Arg Val Leu
545                 550                 555                 560

Arg His Ser Gln Gln Asp Tyr Arg Lys Asn Gln Glu Tyr Ile Ala Lys
                565                 570                 575

Gln Phe Gly Phe Met Gln Lys Gln Ile Gly Tyr Asp Val Leu Ala Glu
            580                 585                 590

Asp Thr Ile Thr Ala Leu Leu His Asn Asn Arg Lys Leu Leu Glu Lys
        595                 600                 605

His Ile Thr Ala Ala Glu Ile Asp Thr Phe Val Ser Leu Val Arg Lys
    610                 615                 620

Asn Arg Glu Pro Arg Phe Leu Asp Tyr Leu Ser Asp Leu Cys Val Ser
625                 630                 635                 640

Met Asn Lys Ser Ile Pro Val Thr Gln Glu Leu Ile Cys Lys Ala Val
                645                 650                 655

Leu Asn Pro Thr Asn Ala Asp Ile Leu Ile Glu Thr Lys Leu Val Leu
            660                 665                 670

Ser Arg Phe Glu Phe Glu Gly Val Ser Thr Gly Glu Asn Ala Leu Glu
        675                 680                 685

Ala Gly Glu Asp Glu Glu Glu Val Trp Leu Phe Trp Arg Asp Ser Asn
    690                 695                 700

Lys Glu Ile Arg Ser Lys Ser Val Arg Glu Leu Ala Gln Asp Ala Lys
705                 710                 715                 720

Glu Gly Gln Lys Glu Asp Arg Asp Val Leu Ser Tyr Tyr Arg Tyr Gln
                725                 730                 735

Leu Asn Leu Phe Ala Arg Met Cys Leu Asp Arg Gln Tyr Leu Ala Ile
            740                 745                 750

Asn Glu Ile Ser Gly Gln Leu Asp Val Asp Leu Ile Leu Arg Cys Met
        755                 760                 765

Ser Asp Glu Asn Leu Pro Tyr Asp Leu Arg Ala Ser Phe Cys Arg Leu
```

-continued

```
            770                 775                 780
Met Leu His Met His Val Asp Arg Asp Pro Gln Glu Gln Val Thr Pro
785                 790                 795                 800

Val Lys Tyr Ala Arg Leu Trp Ser Glu Ile Pro Ser Glu Ile Ala Ile
                805                 810                 815

Asp Asp Tyr Asp Ser Ser Gly Ala Ser Lys Asp Glu Ile Lys Glu Arg
                820                 825                 830

Phe Ala Gln Thr Met Glu Phe Val Glu Tyr Leu Arg Asp Val Val
                    835                 840                 845

Cys Gln Arg Phe Pro Phe Ser Asp Lys Glu Lys Asn Lys Leu Thr Phe
        850                 855                 860

Glu Val Val Asn Leu Ala Arg Asn Leu Ile Tyr Phe Gly Phe Tyr Asn
865                 870                 875                 880

Phe Ser Asp Leu Leu Arg Leu Thr Lys Ile Leu Leu Ala Ile Leu Asp
                    885                 890                 895

Cys Val His Val Thr Thr Ile Phe Pro Ile Ser Lys Met Thr Lys Gly
                900                 905                 910

Glu Glu Asn Lys Gly Ser Asn Val Met Arg Ser Ile His Gly Val Gly
                915                 920                 925

Glu Leu Met Thr Gln Val Val Leu Arg Gly Gly Phe Leu Pro Met
            930                 935                 940

Thr Pro Met Ala Ala Pro Glu Gly Asn Val Lys Gln Ala Glu Pro
945                 950                 955                 960

Glu Lys Glu Asp Ile Met Val Met Asp Thr Lys Leu Lys Ile Ile Glu
                965                 970                 975

Ile Leu Gln Phe Ile Leu Asn Val Arg Leu Asp Tyr Arg Ile Ser Cys
                980                 985                 990

Leu Leu Cys Ile Phe Lys Arg Glu Phe Asp Glu Ser Asn Ser Gln Ser
        995                 1000                1005

Ser Glu Thr Ser Ser Gly Asn Ser Ser Gln Glu Gly Pro Ser Asn
    1010                1015                1020

Val Pro Gly Ala Leu Asp Phe Glu His Ile Glu Glu Gln Ala Glu
    1025                1030                1035

Gly Ile Phe Gly Gly Ser Glu Glu Asn Thr Pro Leu Asp Leu Asp
    1040                1045                1050

Asp His Gly Gly Arg Thr Phe Leu Arg Val Leu Leu His Leu Thr
    1055                1060                1065

Met His Asp Tyr Pro Pro Leu Val Ser Gly Ala Leu Gln Leu Leu
    1070                1075                1080

Phe Arg His Phe Ser Gln Arg Gln Glu Val Leu Gln Ala Phe Lys
    1085                1090                1095

Gln Val Gln Leu Leu Val Thr Ser Gln Asp Val Asp Asn Tyr Lys
    1100                1105                1110

Gln Ile Lys Gln Asp Leu Asp Gln Leu Arg Ser Ile Val Glu Lys
    1115                1120                1125

Ser Glu Leu Trp Val Tyr Lys Gly Gln Gly Pro Asp Glu Pro Met
    1130                1135                1140

Asp Gly Ala Ser Gly Glu Asn Glu His Lys Lys Thr Glu Glu Gly
    1145                1150                1155

Thr Ser Lys Pro Leu Lys His Glu Ser Thr Ser Ser Tyr Asn Tyr
    1160                1165                1170

Arg Val Val Lys Glu Ile Leu Ile Arg Leu Ser Lys Leu Cys Val
    1175                1180                1185
```

```
Gln Glu Ser Ala Ser Val Arg Lys Ser Arg Lys Gln Gln Arg
    1190            1195            1200

Leu Leu Arg Asn Met Gly Ala His Ala Val Val Leu Glu Leu Leu
1205            1210            1215

Gln Ile Pro Tyr Glu Lys Ala Glu Asp Thr Lys Met Gln Glu Ile
1220            1225            1230

Met Arg Leu Ala His Glu Phe Leu Gln Asn Phe Cys Ala Gly Asn
1235            1240            1245

Gln Gln Asn Gln Ala Leu Leu His Lys His Ile Asn Leu Phe Leu
1250            1255            1260

Asn Pro Gly Ile Leu Glu Ala Val Thr Met Gln His Ile Phe Met
1265            1270            1275

Asn Asn Phe Gln Leu Cys Ser Glu Ile Asn Glu Arg Val Val Gln
1280            1285            1290

His Phe Val His Cys Ile Glu Thr His Gly Arg Asn Val Gln Tyr
1295            1300            1305

Ile Lys Phe Leu Gln Thr Ile Val Lys Ala Glu Gly Lys Phe Ile
1310            1315            1320

Lys Lys Cys Gln Asp Met Val Met Ala Glu Leu Val Asn Ser Gly
1325            1330            1335

Glu Asp Val Leu Val Phe Tyr Asn Asp Arg Ala Ser Phe Gln Thr
1340            1345            1350

Leu Ile Gln Met Met Arg Ser Glu Arg Asp Arg Met Asp Glu Asn
1355            1360            1365

Ser Pro Leu Phe Met Tyr His Ile His Leu Val Glu Leu Leu Ala
1370            1375            1380

Val Cys Thr Glu Gly Lys Asn Val Tyr Thr Glu Ile Lys Cys Asn
1385            1390            1395

Ser Leu Leu Pro Leu Asp Asp Ile Val Arg Val Val Thr His Glu
1400            1405            1410

Asp Cys Ile Pro Glu Val Lys Ile Ala Tyr Ile Asn Phe Leu Asn
1415            1420            1425

His Cys Tyr Val Asp Thr Glu Val Glu Met Lys Glu Ile Tyr Thr
1430            1435            1440

Ser Asn His Met Trp Lys Leu Phe Glu Asn Phe Leu Val Asp Ile
1445            1450            1455

Cys Arg Ala Cys Asn Asn Thr Ser Asp Arg Lys His Ala Asp Ser
1460            1465            1470

Val Leu Glu Lys Tyr Val Thr Glu Ile Val Met Ser Ile Val Thr
1475            1480            1485

Thr Phe Phe Ser Ser Pro Phe Ser Asp Gln Ser Thr Thr Leu Gln
1490            1495            1500

Thr Arg Gln Pro Val Phe Val Gln Leu Leu Gln Gly Val Phe Arg
1505            1510            1515

Val Tyr His Cys Asn Trp Leu Met Pro Ser Gln Lys Ala Ser Val
1520            1525            1530

Glu Ser Cys Ile Arg Val Leu Ser Asp Val Ala Lys Ser Arg Ala
1535            1540            1545

Ile Ala Ile Pro Val Asp Leu Asp Ser Gln Val Asn Asn Leu Phe
1550            1555            1560

Leu Lys Ser His Asn Ile Val Gln Lys Thr Ala Met Asn Trp Arg
1565            1570            1575

Leu Ser Ala Arg Asn Ala Ala Arg Arg Asp Ser Val Leu Ala Ala
1580            1585            1590
```

```
Ser Arg Asp Tyr Arg Asn Ile Ile Glu Arg Leu Gln Asp Ile Val
1595                1600                1605

Ser Ala Leu Glu Asp Arg Leu Arg Pro Leu Val Gln Ala Glu Leu
1610                1615                1620

Ser Val Leu Val Asp Val Leu His Arg Pro Glu Leu Leu Phe Pro
1625                1630                1635

Glu Asn Thr Asp Ala Arg Arg Lys Cys Glu Ser Gly Gly Phe Ile
1640                1645                1650

Cys Lys Leu Ile Lys His Thr Lys Gln Leu Leu Glu Glu Asn Glu
1655                1660                1665

Glu Lys Leu Cys Ile Lys Val Leu Gln Thr Leu Arg Glu Met Met
1670                1675                1680

Thr Lys Asp Arg Gly Tyr Gly Glu Lys Gln Ile Ser Ile Asp Glu
1685                1690                1695

Leu Glu Asn Ala Glu Leu Pro Gln Pro Pro Glu Ala Glu Asn Ser
1700                1705                1710

Thr Glu Glu Leu Glu Pro Ser Pro Pro Leu Arg Gln Leu Glu Asp
1715                1720                1725

His Lys Arg Gly Glu Ala Leu Arg Gln Ile Leu Val Asn Arg Tyr
1730                1735                1740

Tyr Gly Asn Ile Arg Pro Ser Gly Arg Arg Glu Ser Leu Thr Ser
1745                1750                1755

Phe Gly Asn Gly Pro Leu Ser Pro Gly Gly Pro Ser Lys Pro Gly
1760                1765                1770

Gly Gly Gly Gly Gly Pro Gly Ser Gly Ser Thr Ser Arg Gly Glu
1775                1780                1785

Met Ser Leu Ala Glu Val Gln Cys His Leu Asp Lys Glu Gly Ala
1790                1795                1800

Ser Asn Leu Val Ile Asp Leu Ile Met Asn Ala Ser Ser Asp Arg
1805                1810                1815

Val Phe His Glu Ser Ile Leu Leu Ala Ile Ala Leu Leu Glu Gly
1820                1825                1830

Gly Asn Thr Thr Ile Gln His Ser Phe Phe Cys Arg Leu Thr Glu
1835                1840                1845

Asp Lys Lys Ser Glu Lys Phe Phe Lys Val Phe Tyr Asp Arg Met
1850                1855                1860

Lys Val Ala Gln Gln Glu Ile Lys Ala Thr Val Thr Val Asn Thr
1865                1870                1875

Ser Asp Leu Gly Asn Lys Lys Lys Asp Asp Glu Val Asp Arg Asp
1880                1885                1890

Ala Pro Ser Arg Lys Lys Ala Lys Glu Pro Thr Thr Gln Ile Thr
1895                1900                1905

Glu Glu Val Arg Asp Gln Leu Leu Glu Ala Ser Ala Ala Thr Arg
1910                1915                1920

Lys Ala Phe Thr Thr Phe Arg Arg Glu Ala Asp Pro Asp Asp His
1925                1930                1935

Tyr Gln Ser Gly Glu Gly Thr Gln Ala Thr Thr Asp Lys Ala Lys
1940                1945                1950

Asp Asp Leu Glu Met Ser Ala Val Ile Thr Ile Met Gln Pro Ile
1955                1960                1965

Leu Arg Phe Leu Gln Leu Leu Cys Glu Asn His Asn Arg Asp Leu
1970                1975                1980

Gln Asn Phe Leu Arg Cys Gln Asn Asn Lys Thr Asn Tyr Asn Leu
```

-continued

```
          1985                1990                1995

Val Cys Glu Thr Leu Gln Phe Leu Asp Cys Ile Cys Gly Ser Thr
     2000                2005                2010

Thr Gly Gly Leu Gly Leu Leu Gly Leu Tyr Ile Asn Glu Lys Asn
     2015                2020                2025

Val Ala Leu Ile Asn Gln Thr Leu Glu Ser Leu Thr Glu Tyr Cys
     2030                2035                2040

Gln Gly Pro Cys His Glu Asn Gln Asn Cys Ile Ala Thr His Glu
     2045                2050                2055

Ser Asn Gly Ile Asp Ile Ile Thr Ala Leu Ile Leu Asn Asp Ile
     2060                2065                2070

Asn Pro Leu Gly Lys Lys Arg Met Asp Leu Val Leu Glu Leu Lys
     2075                2080                2085

Asn Asn Ala Ser Lys Leu Leu Leu Ala Ile Met Glu Ser Arg His
     2090                2095                2100

Asp Ser Glu Asn Ala Glu Arg Ile Leu Tyr Asn Met Arg Pro Lys
     2105                2110                2115

Glu Leu Val Glu Val Ile Lys Lys Ala Tyr Met Gln Gly Glu Val
     2120                2125                2130

Glu Phe Glu Asp Gly Glu Asn Gly Glu Asp Gly Ala Ala Ser Pro
     2135                2140                2145

Arg Asn Val Gly His Asn Ile Tyr Ile Leu Ala His Gln Leu Ala
     2150                2155                2160

Arg His Asn Lys Glu Leu Gln Thr Met Leu Lys Pro Gly Gly Gln
     2165                2170                2175

Val Asp Gly Asp Glu Ala Leu Glu Phe Tyr Ala Lys His Thr Ala
     2180                2185                2190

Gln Ile Glu Ile Val Arg Leu Asp Arg Thr Met Glu Gln Ile Val
     2195                2200                2205

Phe Pro Val Pro Ser Ile Cys Glu Phe Leu Thr Lys Glu Ser Lys
     2210                2215                2220

Leu Arg Ile Tyr Tyr Thr Thr Glu Arg Asp Glu Gln Gly Ser Lys
     2225                2230                2235

Ile Asn Asp Phe Phe Leu Arg Ser Glu Asp Leu Phe Asn Glu Met
     2240                2245                2250

Asn Trp Gln Lys Lys Leu Arg Ala Gln Pro Val Leu Tyr Trp Cys
     2255                2260                2265

Ala Arg Asn Met Ser Phe Trp Ser Ser Ile Ser Phe Asn Leu Ala
     2270                2275                2280

Val Leu Met Asn Leu Leu Val Ala Phe Phe Tyr Pro Phe Lys Gly
     2285                2290                2295

Val Arg Gly Gly Thr Leu Glu Pro His Trp Ser Gly Leu Leu Trp
     2300                2305                2310

Thr Ala Met Leu Ile Ser Leu Ala Ile Val Ile Ala Leu Pro Lys
     2315                2320                2325

Pro His Gly Ile Arg Ala Leu Ile Ala Ser Thr Ile Leu Arg Leu
     2330                2335                2340

Ile Phe Ser Val Gly Leu Gln Pro Thr Leu Phe Leu Leu Gly Ala
     2345                2350                2355

Phe Asn Val Cys Asn Lys Ile Ile Phe Leu Met Ser Phe Val Gly
     2360                2365                2370

Asn Cys Gly Thr Phe Thr Arg Gly Tyr Arg Ala Met Val Leu Asp
     2375                2380                2385
```

```
Val Glu Phe Leu Tyr His Leu Leu Tyr Leu Leu Ile Cys Ala Met
2390                2395                2400

Gly Leu Phe Val His Glu Phe Phe Tyr Ser Leu Leu Leu Phe Asp
2405                2410                2415

Leu Val Tyr Arg Glu Glu Thr Leu Leu Asn Val Ile Lys Ser Val
2420                2425                2430

Thr Arg Asn Gly Arg Pro Ile Ile Leu Thr Ala Ala Leu Ala Leu
2435                2440                2445

Ile Leu Val Tyr Leu Phe Ser Ile Val Gly Tyr Leu Phe Phe Lys
2450                2455                2460

Asp Asp Phe Ile Leu Glu Val Asp Arg Leu Pro Asn Glu Thr Ala
2465                2470                2475

Gly Pro Glu Thr Gly Glu Ser Leu Ala Asn Asp Phe Leu Tyr Ser
2480                2485                2490

Asp Val Cys Arg Val Glu Thr Gly Glu Asn Cys Thr Ser Pro Ala
2495                2500                2505

Pro Lys Glu Glu Leu Leu Pro Val Glu Thr Glu Gln Asp Lys
2510                2515                2520

Glu His Thr Cys Glu Thr Leu Leu Met Cys Ile Val Thr Val Leu
2525                2530                2535

Ser His Gly Leu Arg Ser Gly Gly Gly Val Gly Asp Val Leu Arg
2540                2545                2550

Lys Pro Ser Lys Glu Glu Pro Leu Phe Ala Ala Arg Val Ile Tyr
2555                2560                2565

Asp Leu Leu Phe Phe Phe Met Val Ile Ile Ile Val Leu Asn Leu
2570                2575                2580

Ile Phe Gly Val Ile Ile Asp Thr Phe Ala Asp Leu Arg Ser Glu
2585                2590                2595

Lys Gln Lys Lys Glu Glu Ile Leu Lys Thr Thr Cys Phe Ile Cys
2600                2605                2610

Gly Leu Glu Arg Asp Lys Phe Asp Asn Lys Thr Val Thr Phe Glu
2615                2620                2625

Glu His Ile Lys Glu Glu His Asn Met Trp His Tyr Leu Cys Phe
2630                2635                2640

Ile Val Leu Val Lys Val Lys Asp Ser Thr Glu Tyr Thr Gly Pro
2645                2650                2655

Glu Ser Tyr Val Ala Glu Met Ile Arg Glu Arg Asn Leu Asp Trp
2660                2665                2670

Phe Pro Arg Met Arg Ala Met Ser Leu Val Ser Ser Asp Ser Glu
2675                2680                2685

Gly Glu Gln Asn Glu Leu Arg Asn Leu Gln Glu Lys Leu Glu Ser
2690                2695                2700

Thr Met Lys Leu Val Thr Asn Leu Ser Gly Gln Leu Ser Glu Leu
2705                2710                2715

Lys Asp Gln Met Thr Glu Gln Arg Lys Gln Lys Gln Arg Ile Gly
2720                2725                2730

Leu Leu Gly His Pro Pro His Met Asn Val Asn Pro Gln Gln Pro
2735                2740                2745

Ala

<210> SEQ ID NO 18
<211> LENGTH: 252
<212> TYPE: PRT
<213> ORGANISM: Homo sapiens
```

<400> SEQUENCE: 18

```
Met Glu Ala Met Trp Leu Leu Cys Val Ala Leu Ala Val Leu Ala Trp
1               5                   10                  15

Gly Phe Leu Trp Val Trp Asp Ser Ser Glu Arg Met Lys Ser Arg Glu
            20                  25                  30

Gln Gly Gly Arg Leu Gly Ala Glu Ser Arg Thr Leu Leu Val Ile Ala
        35                  40                  45

His Pro Asp Asp Glu Ala Met Phe Phe Ala Pro Thr Val Leu Gly Leu
    50                  55                  60

Ala Arg Leu Arg His Trp Val Tyr Leu Leu Cys Phe Ser Ala Gly Asn
65                  70                  75                  80

Tyr Tyr Asn Gln Gly Glu Thr Arg Lys Lys Glu Leu Leu Gln Ser Cys
                85                  90                  95

Asp Val Leu Gly Ile Pro Leu Ser Ser Val Met Ile Ile Asp Asn Arg
            100                 105                 110

Asp Phe Pro Asp Pro Gly Met Gln Trp Asp Thr Glu His Val Ala
        115                 120                 125

Arg Val Leu Leu Gln His Ile Glu Val Asn Gly Ile Asn Leu Val Val
    130                 135                 140

Thr Phe Asp Ala Gly Gly Val Ser Gly His Ser Asn His Ile Ala Leu
145                 150                 155                 160

Tyr Ala Ala Val Arg Ala Leu His Ser Glu Gly Lys Leu Pro Lys Gly
                165                 170                 175

Cys Ser Val Leu Thr Leu Gln Ser Val Asn Val Leu Arg Lys Tyr Ile
            180                 185                 190

Ser Leu Leu Asp Leu Pro Leu Ser Leu His Thr Gln Asp Val Leu
        195                 200                 205

Phe Val Leu Asn Ser Lys Glu Val Ala Gln Ala Lys Lys Ala Met Ser
    210                 215                 220

Cys His Arg Ser Gln Leu Leu Trp Phe Arg Arg Leu Tyr Ile Ile Phe
225                 230                 235                 240

Ser Arg Tyr Met Arg Ile Asn Ser Leu Ser Phe Leu
                245                 250
```

<210> SEQ ID NO 19
<211> LENGTH: 920
<212> TYPE: PRT
<213> ORGANISM: Rattus sp.

<400> SEQUENCE: 19

```
Met Glu Arg Ser Thr Val Leu Ile Gln Pro Gly Leu Trp Thr Arg Asp
1               5                   10                  15

Thr Ser Trp Thr Leu Leu Tyr Phe Leu Cys Tyr Ile Leu Pro Gln Thr
            20                  25                  30

Ser Pro Gln Val Leu Arg Ile Gly Gly Ile Phe Glu Thr Val Glu Asn
        35                  40                  45

Glu Pro Val Asn Val Glu Glu Leu Ala Phe Lys Phe Ala Val Thr Ser
    50                  55                  60

Ile Asn Arg Asn Arg Thr Leu Met Pro Asn Thr Thr Leu Thr Tyr Asp
65                  70                  75                  80

Ile Gln Arg Ile Asn Leu Phe Asp Ser Phe Glu Ala Ser Arg Arg Ala
                85                  90                  95

Cys Asp Gln Leu Ala Leu Gly Val Ala Ala Leu Phe Gly Pro Ser His
            100                 105                 110

Ser Ser Ser Val Ser Ala Val Gln Ser Ile Cys Asn Ala Leu Glu Val
```

```
                115                 120                 125
Pro His Ile Gln Thr Arg Trp Lys His Pro Ser Val Asp Ser Arg Asp
130                 135                 140

Leu Phe Tyr Ile Asn Leu Tyr Pro Asp Tyr Ala Ala Ile Ser Arg Ala
145                 150                 155                 160

Val Leu Asp Leu Val Leu Tyr Tyr Asn Trp Lys Thr Val Thr Val Val
                165                 170                 175

Tyr Glu Asp Ser Thr Gly Leu Ile Arg Leu Gln Glu Leu Ile Lys Ala
                180                 185                 190

Pro Ser Arg Tyr Asn Ile Lys Ile Lys Ile Arg Gln Leu Pro Pro Ala
                195                 200                 205

Asn Lys Asp Ala Lys Pro Leu Leu Lys Glu Met Lys Lys Ser Lys Glu
210                 215                 220

Phe Tyr Val Ile Phe Asp Cys Ser His Glu Thr Ala Ala Glu Ile Leu
225                 230                 235                 240

Lys Gln Ile Leu Phe Met Gly Met Met Thr Glu Tyr Tyr His Tyr Phe
                245                 250                 255

Phe Thr Thr Leu Asp Leu Phe Ala Leu Asp Leu Glu Leu Tyr Arg Tyr
                260                 265                 270

Ser Gly Val Asn Met Thr Gly Phe Arg Lys Leu Asn Ile Asp Asn Pro
                275                 280                 285

His Val Ser Ser Ile Ile Glu Lys Trp Ser Met Glu Arg Leu Gln Ala
                290                 295                 300

Pro Pro Arg Pro Glu Thr Gly Leu Leu Asp Gly Met Met Thr Thr Glu
305                 310                 315                 320

Ala Ala Leu Met Tyr Asp Ala Val Tyr Met Val Ala Ile Ala Ser His
                325                 330                 335

Arg Ala Ser Gln Leu Thr Val Ser Ser Leu Gln Cys His Arg His Lys
                340                 345                 350

Pro Cys Ala Leu Gly Pro Arg Phe Met Asn Leu Ile Lys Glu Ala Arg
                355                 360                 365

Trp Asp Gly Leu Thr Gly Arg Ile Thr Phe Asn Lys Thr Asp Gly Leu
370                 375                 380

Arg Lys Asp Phe Asp Leu Asp Ile Ile Ser Leu Lys Glu Glu Gly Thr
385                 390                 395                 400

Glu Lys Ala Ser Gly Glu Val Ser Lys His Leu Tyr Lys Val Trp Lys
                405                 410                 415

Lys Ile Gly Ile Trp Asn Ser Asn Ser Gly Leu Asn Met Thr Asp Gly
                420                 425                 430

Asn Arg Asp Arg Ser Asn Asn Ile Thr Asp Ser Leu Ala Asn Arg Thr
                435                 440                 445

Leu Ile Val Thr Thr Ile Leu Glu Glu Pro Tyr Val Met Tyr Arg Lys
450                 455                 460

Ser Asp Lys Pro Leu Tyr Gly Asn Asp Arg Phe Glu Ala Tyr Cys Leu
465                 470                 475                 480

Asp Leu Leu Lys Glu Leu Ser Asn Ile Leu Gly Phe Leu Tyr Asp Val
                485                 490                 495

Lys Leu Val Pro Asp Gly Lys Tyr Gly Ala Gln Asn Asp Lys Gly Glu
                500                 505                 510

Trp Asn Gly Met Val Lys Glu Leu Ile Asp His Arg Ala Asp Leu Ala
                515                 520                 525

Val Ala Pro Leu Thr Ile Thr Tyr Val Arg Glu Lys Val Ile Asp Phe
530                 535                 540
```

```
Ser Lys Pro Phe Met Thr Leu Gly Ile Ser Ile Leu Tyr Arg Lys Pro
545                 550                 555                 560

Asn Gly Thr Asn Pro Gly Val Phe Ser Phe Leu Asn Pro Leu Ser Pro
                565                 570                 575

Asp Ile Trp Met Tyr Val Leu Leu Ala Cys Leu Gly Val Ser Cys Val
            580                 585                 590

Leu Phe Val Ile Ala Arg Phe Thr Pro Tyr Glu Trp Tyr Asn Pro His
        595                 600                 605

Pro Cys Asn Pro Asp Ser Asp Val Glu Asn Asn Phe Thr Leu Leu
    610                 615                 620

Asn Ser Phe Trp Phe Gly Val Gly Ala Leu Met Gln Gln Gly Ser Glu
625                 630                 635                 640

Leu Met Pro Lys Ala Leu Ser Thr Arg Ile Val Gly Gly Ile Trp Trp
                645                 650                 655

Phe Phe Thr Leu Ile Ile Ile Ser Ser Tyr Thr Ala Asn Leu Ala Ala
                660                 665                 670

Phe Leu Thr Val Glu Arg Met Glu Ser Pro Ile Asp Ser Ala Asp Asp
            675                 680                 685

Leu Ala Lys Gln Thr Lys Ile Glu Tyr Gly Ala Val Arg Asp Gly Ser
690                 695                 700

Thr Met Thr Phe Phe Lys Lys Ser Lys Ile Ser Thr Tyr Glu Lys Met
705                 710                 715                 720

Trp Ala Phe Met Ser Ser Arg Gln Gln Ser Ala Leu Val Lys Asn Ser
                725                 730                 735

Asp Glu Gly Ile Gln Arg Val Leu Thr Thr Asp Tyr Ala Leu Leu Met
                740                 745                 750

Glu Ser Thr Ser Ile Glu Tyr Val Thr Gln Arg Asn Cys Asn Leu Thr
            755                 760                 765

Gln Ile Gly Gly Leu Ile Asp Ser Lys Gly Tyr Gly Val Gly Thr Pro
        770                 775                 780

Ile Gly Ser Pro Tyr Arg Asp Lys Ile Thr Ile Ala Ile Leu Gln Leu
785                 790                 795                 800

Gln Glu Glu Gly Lys Leu His Met Met Lys Glu Lys Trp Trp Arg Gly
                805                 810                 815

Asn Gly Cys Pro Glu Glu Asp Ser Lys Glu Ala Ser Ala Leu Gly Val
                820                 825                 830

Glu Asn Ile Gly Gly Ile Phe Ile Val Leu Ala Ala Gly Leu Val Leu
            835                 840                 845

Ser Val Phe Val Ala Ile Gly Glu Phe Leu Tyr Lys Ser Arg Lys Asn
850                 855                 860

Asn Asp Val Glu Gln Cys Leu Ser Phe Asn Ala Ile Met Glu Glu Leu
865                 870                 875                 880

Gly Ile Ser Leu Lys Asn Gln Lys Lys Leu Lys Lys Ser Arg Thr
                885                 890                 895

Lys Gly Lys Ser Ser Phe Thr Ser Ile Leu Thr Cys His Gln Arg Arg
                900                 905                 910

Thr Gln Arg Lys Glu Thr Val Ala
                915                 920

<210> SEQ ID NO 20
<211> LENGTH: 3011
<212> TYPE: PRT
<213> ORGANISM: Unknown
<220> FEATURE:
<223> OTHER INFORMATION: Viral
```

-continued

<400> SEQUENCE: 20

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
            195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Gly Cys
        290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly His Thr Val Ser Gly Ser Val
385                 390                 395                 400

Ser Phe Leu Ala Pro Gly Ala Lys Gln Asn Val Gln Leu Ile Asn Thr
                405                 410                 415

```
Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
            435                 440                 445

Ser Ser Gly Cys Pro Glu Arg Leu Ala Ser Cys Arg Pro Leu Thr Asp
        450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
            515                 520                 525

Trp Gly Glu Asn Asp Thr Asp Val Phe Val Leu Asn Asn Thr Arg Pro
            530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
            595                 600                 605

Val Asp Tyr Pro Tyr Arg Leu Trp His Tyr Pro Cys Thr Ile Asn Tyr
610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Lys Trp Val Pro
        770                 775                 780

Gly Ala Val Tyr Thr Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
            835                 840                 845
```

```
Phe Leu Thr Arg Val Glu Ala Gln Leu His Val Trp Ile Pro Pro Leu
    850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ala Gly Gly His Tyr Val Gln Met Val Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Ala Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
    1085                1090                1095

Gln Met Tyr Thr Asn Val Asp Gln Asp Leu Val Gly Trp Pro Ala
    1100                1105                1110

Pro Gln Gly Ser Arg Ser Leu Thr Pro Cys Thr Cys Gly Ser Ser
    1115                1120                1125

Asp Leu Tyr Leu Val Thr Arg His Ala Asp Val Ile Pro Val Arg
    1130                1135                1140

Arg Arg Gly Asp Ser Arg Gly Ser Leu Leu Ser Pro Arg Pro Ile
    1145                1150                1155

Ser Tyr Leu Lys Gly Ser Ser Gly Gly Pro Leu Leu Cys Pro Ala
    1160                1165                1170

Gly His Ala Val Gly Ile Phe Arg Ala Ala Val Cys Thr Arg Gly
    1175                1180                1185

Val Ala Lys Ala Val Asp Phe Ile Pro Val Glu Asn Leu Glu Thr
    1190                1195                1200

Thr Met Arg Ser Pro Val Phe Thr Asp Asn Ser Ser Pro Pro Val
    1205                1210                1215

Val Pro Gln Ser Phe Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Gly
```

```
                    1250                1255                1260
Phe Gly Ala Tyr Met Ser Lys Ala His Gly Ile Asp Pro Asn Ile
    1265                1270                1275
Arg Thr Gly Val Arg Thr Ile Thr Thr Gly Ser Pro Ile Thr Tyr
    1280                1285                1290
Ser Thr Tyr Gly Lys Phe Leu Ala Asp Gly Gly Cys Ser Gly Gly
    1295                1300                1305
Ala Tyr Asp Ile Ile Ile Cys Asp Glu Cys His Ser Thr Asp Ala
    1310                1315                1320
Thr Ser Ile Leu Gly Ile Gly Thr Val Leu Asp Gln Ala Glu Thr
    1325                1330                1335
Ala Gly Ala Arg Leu Val Val Leu Ala Thr Ala Thr Pro Pro Gly
    1340                1345                1350
Ser Val Thr Val Pro His Pro Asn Ile Glu Glu Val Ala Leu Ser
    1355                1360                1365
Thr Thr Gly Glu Ile Pro Phe Tyr Gly Lys Ala Ile Pro Leu Glu
    1370                1375                1380
Val Ile Lys Gly Gly Arg His Leu Ile Phe Cys His Ser Lys Lys
    1385                1390                1395
Lys Cys Asp Glu Leu Ala Ala Lys Leu Val Ala Leu Gly Ile Asn
    1400                1405                1410
Ala Val Ala Tyr Tyr Arg Gly Leu Asp Val Ser Val Ile Pro Thr
    1415                1420                1425
Ser Gly Asp Val Val Val Ala Thr Asp Ala Leu Met Thr Gly
    1430                1435                1440
Tyr Thr Gly Asp Phe Asp Ser Val Ile Asp Cys Asn Thr Cys Val
    1445                1450                1455
Thr Gln Thr Val Asp Phe Ser Leu Asp Pro Thr Phe Thr Ile Glu
    1460                1465                1470
Thr Ile Thr Leu Pro Gln Asp Ala Val Ser Arg Thr Gln Arg Arg
    1475                1480                1485
Gly Arg Thr Gly Arg Gly Lys Pro Gly Ile Tyr Arg Phe Val Ala
    1490                1495                1500
Pro Gly Glu Arg Pro Ser Gly Met Phe Asp Ser Ser Val Leu Cys
    1505                1510                1515
Glu Cys Tyr Asp Ala Gly Cys Ala Trp Tyr Glu Leu Thr Pro Ala
    1520                1525                1530
Glu Thr Thr Val Arg Leu Arg Ala Tyr Met Asn Thr Pro Gly Leu
    1535                1540                1545
Pro Val Cys Gln Asp His Leu Glu Phe Trp Glu Gly Val Phe Thr
    1550                1555                1560
Gly Leu Thr His Ile Asp Ala His Phe Leu Ser Gln Thr Lys Gln
    1565                1570                1575
Ser Gly Glu Asn Leu Pro Tyr Leu Val Ala Tyr Gln Ala Thr Val
    1580                1585                1590
Cys Ala Arg Ala Gln Ala Pro Pro Pro Ser Trp Asp Gln Met Trp
    1595                1600                1605
Lys Cys Leu Ile Arg Leu Lys Pro Thr Leu His Gly Pro Thr Pro
    1610                1615                1620
Leu Leu Tyr Arg Leu Gly Ala Val Gln Asn Glu Ile Thr Leu Thr
    1625                1630                1635
His Pro Val Thr Lys Tyr Ile Met Thr Cys Met Ser Ala Asp Leu
    1640                1645                1650
```

-continued

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Val Val Leu Ser Gly Lys Pro Ala Ile Ile Pro Asp Arg
1685                1690                1695

Glu Val Leu Tyr Gln Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg Gln Ala
1730                1735                1740

Glu Val Ile Ala Pro Ala Val Gln Thr Asn Trp Gln Lys Leu Glu
1745                1750                1755

Thr Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Ser Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Ile Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Ala Ile Leu Ser Ser Leu Thr Val
1940                1945                1950

Thr Gln Leu Leu Arg Arg Leu His Gln Trp Ile Ser Ser Glu Cys
1955                1960                1965

Thr Thr Pro Cys Ser Gly Ser Trp Leu Arg Asp Ile Trp Asp Trp
1970                1975                1980

Ile Cys Glu Val Leu Ser Asp Phe Lys Thr Trp Leu Lys Ala Lys
1985                1990                1995

Leu Met Pro Gln Leu Pro Gly Ile Pro Phe Val Ser Cys Gln Arg
2000                2005                2010

Gly Tyr Lys Gly Val Trp Arg Gly Asp Gly Ile Met His Thr Arg
2015                2020                2025

Cys His Cys Gly Ala Glu Ile Thr Gly His Val Lys Asn Gly Thr
2030                2035                2040

Met Arg Ile Val Gly Pro Arg Thr Cys Arg Asn Met Trp Ser Gly
2045                2050                2055

| | | | | | | | | | | |
|---|---|---|---|---|---|---|---|---|---|---|
|Thr|Phe 2060|Pro|Ile|Asn|Ala 2065|Tyr|Thr|Thr|Gly 2070|Pro|Cys|Thr|Pro|Leu|
|Pro|Ala 2075|Pro|Asn|Tyr|Thr 2080|Phe|Ala|Leu|Trp 2085|Arg|Val|Ser|Ala|Glu|
|Glu|Tyr 2090|Val|Glu|Ile|Arg 2095|Gln|Val|Gly|Asp 2100|Phe|His|Tyr|Val|Thr|
|Gly|Met 2105|Thr|Thr|Asp|Asn 2110|Leu|Lys|Cys|Pro 2115|Cys|Gln|Val|Pro|Ser|
|Pro|Glu 2120|Phe|Phe|Thr|Glu 2125|Leu|Asp|Gly|Val 2130|Arg|Leu|His|Arg|Phe|
|Ala|Pro 2135|Pro|Cys|Lys|Pro 2140|Leu|Leu|Arg|Glu 2145|Glu|Val|Ser|Phe|Arg|
|Val|Gly 2150|Leu|His|Glu|Tyr 2155|Pro|Val|Gly|Ser 2160|Gln|Leu|Pro|Cys|Glu|
|Pro|Glu 2165|Pro|Asp|Val|Ala 2170|Val|Leu|Thr|Ser 2175|Met|Leu|Thr|Asp|Pro|
|Ser|His 2180|Ile|Thr|Ala|Glu 2185|Ala|Ala|Gly|Arg 2190|Arg|Leu|Ala|Arg|Gly|
|Ser|Pro 2195|Pro|Ser|Val|Ala 2200|Ser|Ser|Ala|Ser 2205|Gln|Leu|Ser|Ala|
|Pro|Ser 2210|Leu|Lys|Ala|Thr 2215|Cys|Thr|Ala|Asn 2220|His|Asp|Ser|Pro|Asp|
|Ala|Glu 2225|Leu|Ile|Glu|Ala 2230|Asn|Leu|Leu|Trp 2235|Arg|Gln|Glu|Met|Gly|
|Gly|Asn 2240|Ile|Thr|Arg|Val 2245|Glu|Ser|Glu|Asn 2250|Lys|Val|Val|Ile|Leu|
|Asp|Ser 2255|Phe|Asp|Pro|Leu 2260|Val|Ala|Glu|Glu 2265|Asp|Glu|Arg|Glu|Ile|
|Ser|Val 2270|Pro|Ala|Glu|Ile 2275|Leu|Arg|Lys|Ser 2280|Arg|Arg|Phe|Ala|Gln|
|Ala|Leu 2285|Pro|Val|Trp|Ala 2290|Arg|Pro|Asp|Tyr 2295|Asn|Pro|Pro|Leu|Val|
|Glu|Thr 2300|Trp|Lys|Lys|Pro 2305|Asp|Tyr|Glu|Pro 2310|Pro|Val|Val|His|Gly|
|Cys|Pro 2315|Leu|Pro|Pro|Lys 2320|Ser|Pro|Pro|Val 2325|Pro|Pro|Pro|Arg|
|Lys|Lys 2330|Arg|Thr|Val|Val 2335|Leu|Thr|Glu|Ser 2340|Thr|Leu|Ser|Thr|Ala|
|Leu|Ala 2345|Glu|Leu|Ala|Ile 2350|Lys|Ser|Phe|Gly 2355|Ser|Ser|Ser|Thr|Ser|
|Gly|Ile 2360|Thr|Gly|Asp|Asn 2365|Thr|Thr|Thr|Ser 2370|Ser|Glu|Pro|Ala|Pro|
|Ser|Gly 2375|Cys|Pro|Arg|Asp 2380|Ser|Asp|Ala|Glu 2385|Ser|Tyr|Ser|Ser|Met|
|Pro|Pro 2390|Leu|Glu|Gly|Glu 2395|Pro|Gly|Asp|Pro 2400|Asp|Leu|Ser|Asp|Gly|
|Ser|Trp 2405|Ser|Thr|Val|Ser 2410|Ser|Glu|Ala|Ser 2415|Ala|Glu|Asp|Val|Val|
|Cys|Cys 2420|Ser|Met|Ser|Tyr 2425|Ser|Trp|Thr|Gly 2430|Ala|Leu|Val|Thr|Pro|
|Cys|Ala 2435|Ala|Glu|Glu|Gln 2440|Lys|Leu|Pro|Ile 2445|Asn|Ala|Leu|Ser|Asn|
|Ser|Leu|Leu|Arg|His|His|Asn|Leu|Val|Tyr|Ser|Thr|Thr|Ser|Arg|

-continued

```
                    2450                2455                2460

Ser Ala Cys Gln Arg Gln Lys Lys Val Thr Phe Asp Arg Leu Gln
2465                2470                2475

Val Leu Asp Ser His Tyr Gln Asp Val Leu Lys Glu Val Lys Ala
      2480                2485                2490

Ala Ala Ser Lys Val Lys Ala Asn Leu Leu Ser Val Glu Glu Ala
2495                2500                2505

Cys Ser Leu Thr Pro Pro His Ser Ala Lys Ser Lys Phe Gly Tyr
2510                2515                2520

Gly Ala Lys Asp Val Arg Cys His Ala Arg Lys Ala Val Thr His
2525                2530                2535

Ile Asn Ser Val Trp Lys Asp Leu Leu Glu Asp Asn Val Thr Pro
2540                2545                2550

Ile Asp Thr Thr Ile Met Ala Lys Asn Glu Val Phe Cys Val Gln
2555                2560                2565

Pro Glu Lys Gly Gly Arg Lys Pro Ala Arg Leu Ile Val Phe Pro
2570                2575                2580

Asp Leu Gly Val Arg Val Cys Glu Lys Met Ala Leu Tyr Asp Val
2585                2590                2595

Val Thr Lys Leu Pro Leu Ala Val Met Gly Ser Ser Tyr Gly Phe
2600                2605                2610

Gln Tyr Ser Pro Gly Gln Arg Val Glu Phe Leu Val Gln Ala Trp
2615                2620                2625

Lys Ser Lys Lys Thr Pro Met Gly Phe Ser Tyr Asp Thr Arg Cys
2630                2635                2640

Phe Asp Ser Thr Val Thr Glu Ser Asp Ile Arg Thr Glu Glu Ala
2645                2650                2655

Ile Tyr Gln Cys Cys Asp Leu Asp Pro Gln Ala Arg Val Ala Ile
2660                2665                2670

Lys Ser Leu Thr Glu Arg Leu Tyr Val Gly Gly Pro Leu Thr Asn
2675                2680                2685

Ser Arg Gly Glu Asn Cys Gly Tyr Arg Arg Cys Arg Ala Ser Gly
2690                2695                2700

Val Leu Thr Thr Ser Cys Gly Asn Thr Leu Thr Cys Tyr Ile Lys
2705                2710                2715

Ala Arg Ala Ala Cys Arg Ala Ala Gly Leu Gln Asp Cys Thr Met
2720                2725                2730

Leu Val Cys Gly Asp Asp Leu Val Val Ile Cys Glu Ser Ala Gly
2735                2740                2745

Val Gln Glu Asp Ala Ala Ser Leu Arg Ala Phe Thr Glu Ala Met
2750                2755                2760

Thr Arg Tyr Ser Ala Pro Pro Gly Asp Pro Pro Gln Pro Glu Tyr
2765                2770                2775

Asp Leu Glu Leu Ile Thr Ser Cys Ser Ser Asn Val Ser Val Ala
2780                2785                2790

His Asp Gly Ala Gly Lys Arg Val Tyr Tyr Leu Thr Arg Asp Pro
2795                2800                2805

Thr Thr Pro Leu Ala Arg Ala Ala Trp Glu Thr Ala Arg His Thr
2810                2815                2820

Pro Val Asn Ser Trp Leu Gly Asn Ile Ile Met Phe Ala Pro Thr
2825                2830                2835

Leu Trp Ala Arg Met Ile Leu Met Thr His Phe Phe Ser Val Leu
2840                2845                2850
```

-continued

```
Ile Ala Arg Asp Gln Leu Glu Gln Ala Leu Asp Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
    2915                2920                2925

Ala Arg Leu Leu Ala Arg Gly Gly Arg Ala Ala Ile Cys Gly Lys
    2930                2935                2940

Tyr Leu Phe Asn Trp Ala Val Arg Thr Lys Leu Lys Leu Thr Pro
    2945                2950                2955

Ile Ala Ala Ala Gly Gln Leu Asp Leu Ser Gly Trp Phe Thr Ala
    2960                2965                2970

Gly Tyr Ser Gly Gly Asp Ile Tyr His Ser Val Ser His Ala Arg
    2975                2980                2985

Pro Arg Trp Phe Trp Phe Cys Leu Leu Leu Leu Ala Ala Gly Val
    2990                2995                3000

Gly Ile Tyr Leu Leu Pro Asn Arg
    3005                3010

<210> SEQ ID NO 21
<211> LENGTH: 160
<212> TYPE: PRT
<213> ORGANISM: Unknown
<220> FEATURE:
<223> OTHER INFORMATION: Viral

<400> SEQUENCE: 21

Met Ile Arg Tyr Ile Ile Leu Gly Leu Leu Thr Leu Ala Ser Ala His
1               5                   10                  15

Gly Thr Thr Gln Lys Val Asp Phe Lys Glu Pro Ala Cys Asn Val Thr
                20                  25                  30

Phe Ala Ala Glu Ala Asn Glu Cys Thr Thr Leu Ile Lys Cys Thr Thr
            35                  40                  45

Glu His Glu Lys Leu Leu Ile Arg His Lys Asn Lys Ile Gly Lys Tyr
        50                  55                  60

Ala Val Tyr Ala Ile Trp Gln Pro Gly Asp Thr Thr Glu Tyr Asn Val
    65                  70                  75                  80

Thr Val Phe Gln Gly Lys Ser His Lys Thr Phe Met Tyr Thr Phe Pro
                    85                  90                  95

Phe Tyr Glu Met Cys Asp Ile Thr Met Tyr Met Ser Lys Gln Tyr Lys
                100                 105                 110

Leu Trp Pro Pro Gln Asn Cys Val Glu Asn Thr Gly Thr Phe Cys Cys
            115                 120                 125

Thr Ala Met Leu Ile Thr Val Leu Ala Leu Val Cys Thr Leu Leu Tyr
        130                 135                 140

Ile Lys Tyr Lys Ser Arg Arg Ser Phe Ile Glu Glu Lys Lys Met Pro
145                 150                 155                 160

<210> SEQ ID NO 22
<211> LENGTH: 490
<212> TYPE: PRT
<213> ORGANISM: Unknown
<220> FEATURE:
<223> OTHER INFORMATION: Rabbit
```

```
<400> SEQUENCE: 22

Met Asp Pro Val Val Leu Gly Leu Cys Leu Ser Cys Leu Leu Leu
1               5                   10                  15

Leu Ser Leu Trp Lys Gln Ser Tyr Gly Gly Lys Leu Pro Pro Gly
            20                  25                  30

Pro Thr Pro Phe Pro Ile Leu Gly Asn Ile Leu Gln Ile Gly Ile Gln
            35                  40                  45

Asp Ile Ser Lys Ser Phe Thr Lys Leu Ser Glu Val Tyr Gly Pro Val
        50                  55                  60

Phe Thr Val Tyr Leu Gly Met Lys Pro Thr Val Val Ile His Gly Tyr
65                  70                  75                  80

Asp Ala Val Lys Glu Ala Leu Val Asp Leu Gly Glu Glu Phe Ser Gly
                85                  90                  95

Arg Ile Val Phe Pro Leu Thr Ala Lys Ile Asn Lys Gly Tyr Gly Ile
            100                 105                 110

Val Phe Ser Asn Gly Lys Arg Trp Lys Glu Thr Arg Phe Ser Leu
            115                 120                 125

Met Thr Leu Arg Asp Phe Gly Met Gly Lys Arg Ser Ile Glu Asp Arg
130                 135                 140

Val Gln Glu Glu Ala Arg Cys Leu Val Glu Glu Leu Arg Lys Thr Asn
145                 150                 155                 160

Gly Ser Pro Cys Asn Pro Thr Phe Ile Leu Gly Ala Ala Pro Cys Asn
                165                 170                 175

Val Ile Cys Ser Val Ile Phe Gln Asn Arg Phe Asp Tyr Thr Asp Gln
            180                 185                 190

Asp Phe Leu Ser Leu Met Gly Lys Leu Asn Glu Asn Phe Lys Ile Leu
            195                 200                 205

Asn Ser Pro Trp Val Gln Met Cys Asn Asn Phe Pro Ile Leu Ile Asp
            210                 215                 220

Tyr Leu Pro Gly Ser His Asn Lys Ile Leu Arg Asn Asn Ile Tyr Ile
225                 230                 235                 240

Arg Asn Tyr Val Leu Glu Lys Ile Lys Glu His Gln Glu Thr Leu Asp
                245                 250                 255

Ile Asn Asn Pro Arg Asp Phe Ile Asp Cys Phe Leu Ile Lys Met Glu
            260                 265                 270

Gln Glu Lys Asp Asn Gln Gln Ser Glu Phe Thr Ile Glu Asn Leu Met
            275                 280                 285

Thr Thr Leu Ser Asp Val Phe Gly Ala Gly Thr Glu Thr Thr Ser Thr
            290                 295                 300

Thr Leu Arg Tyr Gly Leu Leu Leu Met Lys His Pro Glu Val Ile
305                 310                 315                 320

Ala Lys Val Gln Glu Glu Ile Glu Arg Val Ile Gly Arg His Arg Ser
                325                 330                 335

Pro Cys Met Gln Asp Arg Ser Arg Met Pro Tyr Thr Asp Ala Thr Val
            340                 345                 350

His Glu Ile Gln Arg Tyr Ile Asn Leu Ile Pro Asn Asn Val Pro Arg
            355                 360                 365

Ala Thr Thr Cys Asn Val Lys Phe Arg Ser Tyr Leu Ile Pro Lys Gly
            370                 375                 380

Thr Ala Val Ile Thr Ser Leu Thr Ser Met Leu Tyr Asn Asp Lys Glu
385                 390                 395                 400

Phe Pro Asn Pro Asp Arg Phe Asp Pro Gly His Phe Leu Asp Ala Ser
                405                 410                 415
```

```
Gly Lys Phe Arg Lys Ser Asp Tyr Phe Met Pro Phe Ser Thr Gly Lys
            420                 425                 430

Arg Val Cys Val Gly Glu Val Leu Ala Arg Met Glu Leu Phe Leu Phe
            435                 440                 445

Leu Thr Ala Ile Leu Gln Asn Phe Thr Pro Lys Pro Leu Val Asp Pro
450                 455                 460

Lys Asp Ile Asp Thr Thr Pro Leu Val Ser Gly Leu Gly Arg Val Pro
465                 470                 475                 480

Pro Leu Tyr Gln Leu Ser Phe Ile Pro Ala
            485                 490

<210> SEQ ID NO 23
<211> LENGTH: 578
<212> TYPE: PRT
<213> ORGANISM: Homo sapiens

<400> SEQUENCE: 23

Met Ala Ala Met Pro Leu Ala Leu Leu Val Leu Leu Leu Leu Leu Gly
1               5                   10                  15

Pro Gly Gly Trp Cys Leu Ala Glu Pro Pro Arg Asp Ser Leu Arg Glu
            20                  25                  30

Glu Leu Val Ile Thr Pro Leu Pro Ser Gly Asp Val Ala Ala Thr Phe
        35                  40                  45

Gln Phe Arg Thr Arg Trp Asp Ser Glu Leu Gln Arg Glu Gly Val Ser
    50                  55                  60

His Tyr Arg Leu Phe Pro Lys Ala Leu Gly Gln Leu Ile Ser Lys Tyr
65                  70                  75                  80

Ser Leu Arg Glu Leu His Leu Ser Phe Thr Gln Gly Phe Trp Arg Thr
                85                  90                  95

Arg Tyr Trp Gly Pro Pro Phe Leu Gln Ala Pro Ser Gly Ala Glu Leu
            100                 105                 110

Trp Val Trp Phe Gln Asp Thr Val Thr Asp Val Asp Lys Ser Trp Lys
        115                 120                 125

Glu Leu Ser Asn Val Leu Ser Gly Ile Phe Cys Ala Ser Leu Asn Phe
    130                 135                 140

Ile Asp Ser Thr Asn Thr Val Thr Pro Thr Ala Ser Phe Lys Pro Leu
145                 150                 155                 160

Gly Leu Ala Asn Asp Thr Asp His Tyr Phe Leu Arg Tyr Ala Val Leu
                165                 170                 175

Pro Arg Glu Val Val Cys Thr Glu Asn Leu Thr Pro Trp Lys Lys Leu
            180                 185                 190

Leu Pro Cys Ser Ser Lys Ala Gly Leu Ser Val Leu Leu Lys Ala Asp
        195                 200                 205

Arg Leu Phe His Thr Ser Tyr His Ser Gln Ala Val His Ile Arg Pro
    210                 215                 220

Val Cys Arg Asn Ala Arg Cys Thr Ser Ile Ser Trp Glu Leu Arg Gln
225                 230                 235                 240

Thr Leu Ser Val Val Phe Asp Ala Phe Ile Thr Gly Gln Gly Lys Lys
                245                 250                 255

Asp Trp Ser Leu Phe Arg Met Phe Ser Arg Thr Leu Thr Glu Pro Cys
            260                 265                 270

Pro Leu Ala Ser Glu Ser Arg Val Tyr Val Asp Ile Thr Thr Tyr Asn
        275                 280                 285

Gln Asp Asn Glu Thr Leu Glu Val His Pro Pro Thr Thr Thr Thr Tyr
    290                 295                 300
```

```
Gln Asp Val Ile Leu Gly Thr Arg Lys Thr Tyr Ala Ile Tyr Asp Leu
305                 310                 315                 320

Leu Asp Thr Ala Met Ile Asn Asn Ser Arg Asn Leu Asn Ile Gln Leu
            325                 330                 335

Lys Trp Lys Arg Pro Pro Glu Asn Glu Ala Pro Pro Val Pro Phe Leu
        340                 345                 350

His Ala Gln Arg Tyr Val Ser Gly Tyr Gly Leu Gln Lys Gly Glu Leu
    355                 360                 365

Ser Thr Leu Leu Tyr Asn Thr His Pro Tyr Arg Ala Phe Pro Val Leu
370                 375                 380

Leu Leu Asp Thr Val Pro Trp Tyr Leu Arg Leu Tyr Val His Thr Leu
385                 390                 395                 400

Thr Ile Thr Ser Lys Gly Lys Glu Asn Lys Pro Ser Tyr Ile His Tyr
                405                 410                 415

Gln Pro Ala Gln Asp Arg Leu Gln Pro His Leu Leu Glu Met Leu Ile
            420                 425                 430

Gln Leu Pro Ala Asn Ser Val Thr Lys Val Ser Ile Gln Phe Glu Arg
        435                 440                 445

Ala Leu Leu Lys Trp Thr Glu Tyr Thr Pro Asp Pro Asn His Gly Phe
450                 455                 460

Tyr Val Ser Pro Ser Val Leu Ser Ala Leu Val Pro Ser Met Val Ala
465                 470                 475                 480

Ala Lys Pro Val Asp Trp Glu Glu Ser Pro Leu Phe Asn Ser Leu Phe
                485                 490                 495

Pro Val Ser Asp Gly Ser Asn Tyr Phe Val Arg Leu Tyr Thr Glu Pro
            500                 505                 510

Leu Leu Val Asn Leu Pro Thr Pro Asp Phe Ser Met Pro Tyr Asn Val
        515                 520                 525

Ile Cys Leu Thr Cys Thr Val Ala Val Cys Tyr Gly Ser Phe Tyr
530                 535                 540

Asn Leu Leu Thr Arg Thr Phe His Ile Glu Glu Pro Arg Thr Gly Gly
545                 550                 555                 560

Leu Ala Lys Arg Leu Ala Asn Leu Ile Arg Arg Ala Arg Gly Val Pro
                565                 570                 575

Pro Leu

<210> SEQ ID NO 24
<211> LENGTH: 134
<212> TYPE: PRT
<213> ORGANISM: Rattus sp.

<400> SEQUENCE: 24

Met Ala Glu Gln Ser Asp Lys Asp Val Lys Tyr Tyr Thr Leu Glu Glu
1               5                   10                  15

Ile Gln Lys His Lys Asp Ser Lys Ser Thr Trp Val Ile Leu His His
            20                  25                  30

Lys Val Tyr Asp Leu Thr Lys Phe Leu Glu Glu His Pro Gly Gly Glu
        35                  40                  45

Glu Val Leu Arg Glu Gln Ala Gly Gly Asp Ala Thr Glu Asn Phe Glu
    50                  55                  60

Asp Val Gly His Ser Thr Asp Ala Arg Glu Leu Ser Lys Thr Tyr Ile
65                  70                  75                  80

Ile Gly Glu Leu His Pro Asp Asp Arg Ser Lys Ile Ala Lys Pro Ser
                85                  90                  95
```

```
Glu Thr Leu Ile Thr Thr Val Glu Ser Asn Ser Ser Trp Trp Thr Asn
            100                 105                 110
Trp Val Ile Pro Ala Ile Ser Ala Leu Val Val Ala Leu Met Tyr Arg
            115                 120                 125
Leu Tyr Met Ala Glu Asp
            130
```

<210> SEQ ID NO 25
<211> LENGTH: 857
<212> TYPE: PRT
<213> ORGANISM: Homo sapiens

<400> SEQUENCE: 25

```
Met Ala Ile Gln Leu Arg Ser Leu Phe Pro Leu Ala Leu Pro Gly Met
1               5                   10                  15
Leu Ala Leu Leu Gly Trp Trp Trp Phe Ser Arg Lys Lys Asp Arg
            20                  25                  30
Leu Ser Ser Ser Asp Lys Gln Val Glu Thr Leu Lys Val Gly Pro Ala
            35                  40                  45
Ile Lys Asp Arg Arg Leu Ser Glu Glu Ala Cys Pro Gly Val Leu Ser
50                  55                  60
Val Ala Pro Thr Val Thr Gln Pro Pro Gly Arg Glu Glu Gln Arg Ser
65                  70                  75                  80
Val Asp Lys Pro Ser Thr Glu Pro Leu Ala Leu Pro Arg Thr Arg Gln
                85                  90                  95
Val Arg Arg Arg Ser Glu Ser Ser Gly Asn Leu Pro Ser Val Ala Asp
                100                 105                 110
Thr Arg Ser Gln Pro Gly Pro Cys Arg Asp Glu Ile Ala Lys Val Glu
                115                 120                 125
Leu Ser Leu Met Gly Asp Lys Ala Lys Ser Ile Pro Leu Gly Cys Pro
            130                 135                 140
Leu Leu Pro Lys Asp Ala Ser Phe Pro Tyr Glu Ala Val Glu Arg Cys
145                 150                 155                 160
Lys Gln Glu Ser Ala Leu Gly Lys Thr Pro Gly Arg Gly Trp Pro Ser
                165                 170                 175
Pro Tyr Ala Ala Ser Gly Glu Lys Ala Arg Glu Thr Gly Gly Thr Glu
                180                 185                 190
Gly Thr Gly Asp Ala Val Leu Gly Glu Asn Val Ser Glu Glu Gly Leu
            195                 200                 205
Leu Ser Gln Glu Cys Val Ser Glu Val Glu Lys Ser Glu Phe Pro Ile
            210                 215                 220
Leu Ala Pro Gly Gly Gly Glu Gly Glu Val Ser His Gly Pro Pro
225                 230                 235                 240
Gln Val Ala Glu Leu Leu Lys Lys Glu Glu Tyr Ile Val Gly Lys Leu
                245                 250                 255
Pro Ser Ser Phe Val Glu Pro Val His Ser Pro Val Lys Asp Glu
                260                 265                 270
Asp Ala Leu Glu Pro Gln Val Lys Gly Ser Ser Asn Thr Ser Asp Arg
            275                 280                 285
Asp Leu Ala Gly Glu Leu Asp Lys Asp Glu Thr Val Pro Glu Asn Asp
290                 295                 300
Gln Ile Lys Gln Ala Ala Phe Gln Leu Ile Ser Gln Val Ile Leu Glu
305                 310                 315                 320
Ala Thr Glu Glu Leu Arg Pro Thr Thr Val Gly Lys Thr Val Ala Gln
                325                 330                 335
```

```
Val His Pro Ile Ser Ala Thr Gln Pro Lys Gly Lys Glu Glu Ser Cys
            340                 345                 350

Val Pro Ala Ser Gln Glu Thr Ser Leu Gly Gln Asp Thr Ser Asp Pro
            355                 360                 365

Ala Ser Thr Arg Thr Gly Ala Thr Ala Ser Pro Ser Ala Glu Ala Leu
            370                 375                 380

Pro Pro Lys Thr Tyr Val Ser Cys Leu Ser Ser Pro Leu Ser Gly Pro
385                 390                 395                 400

Thr Lys Asp Gln Lys Pro Lys Asn Ser Ala His His Ile Ser Leu Ala
            405                 410                 415

Pro Cys Pro Pro Val Thr Pro Gln Arg Gln Ser Leu Glu Gly Ala
            420                 425                 430

Ser Asn Pro Arg Gly Asp Asp Asn Phe Val Ala Cys Met Ala Asn Asn
            435                 440                 445

Ser Gln Ser Val Leu Ser Val Ser Ser Leu Gly Gln Cys Ser Asp Pro
            450                 455                 460

Val Ser Thr Ser Gly Leu Glu Asp Ser Cys Thr Glu Thr Ile Ser Ser
465                 470                 475                 480

Ser Gly Asp Lys Ala Ile Thr Pro Pro Leu Pro Val Ser Thr Gln Pro
            485                 490                 495

Phe Ser Asn Gly Val Leu Lys Glu Glu Leu Ser Asp Leu Gly Thr Glu
            500                 505                 510

Asp Gly Trp Thr Met Asp Thr Glu Ala Asp His Ser Gly Gly Ser Asp
            515                 520                 525

Gly Asn Ser Met Asp Ser Val Asp Ser Cys Cys Gly Leu Thr Lys Pro
            530                 535                 540

Asp Ser Pro Gln Ser Val Gln Ala Gly Ser Asn Pro Lys Lys Val Asp
545                 550                 555                 560

Leu Ile Ile Trp Glu Ile Glu Val Pro Lys His Leu Val Gly Arg Leu
            565                 570                 575

Ile Gly Lys Gln Gly Arg Tyr Val Ser Phe Leu Lys Gln Thr Ser Gly
            580                 585                 590

Ala Lys Ile Tyr Ile Ser Thr Leu Pro Tyr Thr Gln Asn Ile Gln Ile
            595                 600                 605

Cys His Ile Glu Gly Ser Gln His His Val Asp Lys Ala Leu Asn Leu
            610                 615                 620

Ile Gly Lys Lys Phe Lys Glu Leu Asn Leu Thr Asn Ile Tyr Ala Pro
625                 630                 635                 640

Pro Leu Pro Ser Leu Ala Leu Pro Ser Leu Pro Met Thr Ser Trp Leu
            645                 650                 655

Met Leu Pro Asp Gly Ile Thr Val Glu Val Ile Val Asn Gln Val
            660                 665                 670

Asn Ala Gly His Leu Phe Val Gln Gln His Thr His Pro Thr Phe His
            675                 680                 685

Ala Leu Arg Ser Leu Asp Gln Gln Met Tyr Leu Cys Tyr Ser Gln Pro
            690                 695                 700

Gly Ile Pro Thr Leu Pro Thr Pro Val Glu Ile Thr Val Ile Cys Ala
705                 710                 715                 720

Ala Pro Gly Ala Asp Gly Ala Trp Trp Arg Ala Gln Val Val Ala Ser
            725                 730                 735

Tyr Glu Glu Thr Asn Glu Val Glu Ile Arg Tyr Val Asp Tyr Gly Gly
            740                 745                 750

Tyr Lys Arg Val Lys Val Asp Val Leu Arg Gln Ile Arg Ser Asp Phe
            755                 760                 765
```

Val Thr Leu Pro Phe Gln Gly Ala Glu Val Leu Leu Asp Ser Val Val
770 775 780

Pro Leu Ser Asp Asp His Phe Ser Pro Glu Ala Asp Ala Ala Met
785 790 795 800

Ser Glu Met Thr Gly Asn Thr Ala Leu Leu Ala Gln Val Thr Ser Tyr
805 810 815

Ser Ala Thr Gly Leu Pro Leu Ile Gln Leu Trp Ser Val Val Gly Asp
820 825 830

Glu Val Val Leu Ile Asn Arg Ser Leu Val Glu Arg Gly Leu Ala Gln
835 840 845

Trp Val Asp Ser Tyr Tyr Ala Ser Leu
850 855

<210> SEQ ID NO 26
<211> LENGTH: 890
<212> TYPE: PRT
<213> ORGANISM: Homo sapiens

<400> SEQUENCE: 26

Met Gly Cys Lys Thr Gly Pro Lys Pro Phe Gly Gly Glu Thr Ile
1 5 10 15

Arg Pro Ile Arg Ile Arg Arg Cys Ser Tyr Phe Thr Ser Thr Asp Ser
20 25 30

Lys Met Ala Ile Gln Leu Arg Ser Leu Phe Pro Leu Ala Leu Pro Gly
35 40 45

Met Leu Ala Leu Leu Gly Trp Trp Phe Phe Ser Arg Lys Lys Asp
50 55 60

Arg Leu Ser Ser Asp Lys Gln Val Glu Thr Leu Lys Val Gly Pro
65 70 75 80

Ala Ile Lys Asp Arg Arg Leu Ser Glu Glu Ala Cys Pro Gly Val Leu
85 90 95

Ser Val Ala Pro Thr Val Thr Gln Pro Pro Gly Arg Glu Glu Gln Arg
100 105 110

Ser Val Asp Lys Pro Ser Thr Glu Pro Leu Ala Leu Pro Arg Thr Arg
115 120 125

Gln Val Arg Arg Arg Ser Glu Ser Ser Gly Asn Leu Pro Ser Val Ala
130 135 140

Asp Thr Arg Ser Gln Pro Gly Pro Cys Arg Asp Glu Ile Ala Lys Val
145 150 155 160

Glu Leu Ser Leu Met Gly Asp Lys Ala Lys Ser Ile Pro Leu Gly Cys
165 170 175

Pro Leu Leu Pro Lys Asp Ala Ser Phe Pro Tyr Glu Ala Val Glu Arg
180 185 190

Cys Lys Gln Glu Ser Ala Leu Gly Lys Thr Pro Gly Arg Gly Trp Pro
195 200 205

Ser Pro Tyr Ala Ala Ser Gly Glu Lys Ala Arg Glu Thr Gly Gly Thr
210 215 220

Glu Gly Thr Gly Asp Ala Val Leu Gly Glu Asn Val Ser Glu Glu Gly
225 230 235 240

Leu Leu Ser Gln Glu Cys Val Ser Glu Val Glu Lys Ser Glu Phe Pro
245 250 255

Ile Leu Ala Pro Gly Gly Gly Glu Glu Val Ser His Gly Pro
260 265 270

Pro Gln Val Ala Glu Leu Leu Lys Lys Glu Glu Tyr Ile Val Gly Lys
275 280 285

```
Leu Pro Ser Ser Phe Val Glu Pro Val His Ser Glu Pro Val Lys Asp
    290                 295                 300

Glu Asp Ala Leu Glu Pro Gln Val Lys Gly Ser Ser Asn Thr Ser Asp
305                 310                 315                 320

Arg Asp Leu Ala Gly Glu Leu Asp Lys Asp Glu Thr Val Pro Glu Asn
                325                 330                 335

Asp Gln Ile Lys Gln Ala Ala Phe Gln Leu Ile Ser Gln Val Ile Leu
                340                 345                 350

Glu Ala Thr Glu Glu Leu Arg Pro Thr Thr Val Gly Lys Thr Val Ala
            355                 360                 365

Gln Val His Pro Ile Ser Ala Thr Gln Pro Lys Gly Lys Glu Glu Ser
            370                 375                 380

Cys Val Pro Ala Ser Gln Glu Thr Ser Leu Gly Gln Asp Thr Ser Asp
385                 390                 395                 400

Pro Ala Ser Thr Arg Thr Gly Ala Thr Ala Ser Pro Ser Ala Glu Ala
                405                 410                 415

Leu Pro Pro Lys Thr Tyr Val Ser Cys Leu Ser Ser Pro Leu Ser Gly
                420                 425                 430

Pro Thr Lys Asp Gln Lys Pro Lys Asn Ser Ala His Ile Ser Leu
            435                 440                 445

Ala Pro Cys Pro Pro Val Thr Pro Gln Arg Gln Ser Leu Glu Gly
450                 455                 460

Ala Ser Asn Pro Arg Gly Asp Asn Phe Val Ala Cys Met Ala Asn
465                 470                 475                 480

Asn Ser Gln Ser Val Leu Ser Val Ser Ser Leu Gly Gln Cys Ser Asp
            485                 490                 495

Pro Val Ser Thr Ser Gly Leu Glu Asp Ser Cys Thr Glu Thr Ile Ser
            500                 505                 510

Ser Ser Gly Asp Lys Ala Ile Thr Pro Pro Leu Pro Val Ser Thr Gln
            515                 520                 525

Pro Phe Ser Asn Gly Val Leu Lys Glu Glu Leu Ser Asp Leu Gly Thr
        530                 535                 540

Glu Asp Gly Trp Thr Met Asp Thr Glu Ala Asp His Ser Gly Gly Ser
545                 550                 555                 560

Asp Gly Asn Ser Met Asp Ser Val Asp Ser Cys Cys Gly Leu Thr Lys
                565                 570                 575

Pro Asp Ser Pro Gln Ser Val Gln Ala Gly Ser Asn Pro Lys Lys Val
            580                 585                 590

Asp Leu Ile Ile Trp Glu Ile Glu Val Pro Lys His Leu Val Gly Arg
        595                 600                 605

Leu Ile Gly Lys Gln Gly Arg Tyr Val Ser Phe Leu Lys Gln Thr Ser
    610                 615                 620

Gly Ala Lys Ile Tyr Ile Ser Thr Leu Pro Tyr Thr Gln Asn Ile Gln
625                 630                 635                 640

Ile Cys His Ile Glu Gly Ser Gln His His Val Asp Lys Ala Leu Asn
                645                 650                 655

Leu Ile Gly Lys Lys Phe Lys Glu Leu Asn Leu Thr Asn Ile Tyr Ala
            660                 665                 670

Pro Pro Leu Pro Ser Leu Ala Leu Pro Ser Leu Pro Met Thr Ser Trp
            675                 680                 685

Leu Met Leu Pro Asp Gly Ile Thr Val Glu Val Ile Val Asn Gln
690                 695                 700

Val Asn Ala Gly His Leu Phe Val Gln Gln His Thr His Pro Thr Phe
```

```
                705                 710                 715                 720
His Ala Leu Arg Ser Leu Asp Gln Gln Met Tyr Leu Cys Tyr Ser Gln
                    725                 730                 735

Pro Gly Ile Pro Thr Leu Pro Thr Pro Val Glu Ile Thr Val Ile Cys
                740                 745                 750

Ala Ala Pro Gly Ala Asp Gly Ala Trp Trp Arg Ala Gln Val Val Ala
            755                 760                 765

Ser Tyr Glu Glu Thr Asn Glu Val Glu Ile Arg Tyr Val Asp Tyr Gly
        770                 775                 780

Gly Tyr Lys Arg Val Lys Val Asp Val Leu Arg Gln Ile Arg Ser Asp
785                 790                 795                 800

Phe Val Thr Leu Pro Phe Gln Gly Ala Glu Val Leu Leu Asp Ser Val
                805                 810                 815

Val Pro Leu Ser Asp Asp His Phe Ser Pro Glu Ala Asp Ala Ala
                820                 825                 830

Met Ser Glu Met Thr Gly Asn Thr Ala Leu Leu Ala Gln Val Thr Ser
            835                 840                 845

Tyr Ser Ala Thr Gly Leu Pro Leu Ile Gln Leu Trp Ser Val Val Gly
        850                 855                 860

Asp Glu Val Val Leu Ile Asn Arg Ser Leu Val Glu Arg Gly Leu Ala
865                 870                 875                 880

Gln Trp Val Asp Ser Tyr Tyr Ala Ser Leu
                885                 890

<210> SEQ ID NO 27
<211> LENGTH: 292
<212> TYPE: PRT
<213> ORGANISM: Homo sapiens

<400> SEQUENCE: 27

Met Ala Phe Met Lys Lys Tyr Leu Leu Pro Ile Leu Gly Leu Phe Met
1               5                   10                  15

Ala Tyr Tyr Tyr Ser Ala Asn Glu Glu Phe Arg Pro Glu Met Leu
            20                  25                  30

Gln Gly Lys Lys Val Ile Val Thr Gly Ala Ser Lys Gly Ile Gly Arg
        35                  40                  45

Glu Met Ala Tyr His Leu Ala Lys Met Gly Ala His Val Val Val Thr
    50                  55                  60

Ala Arg Ser Lys Glu Thr Leu Gln Lys Val Val Ser His Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Val Ala Gln Ala Gly Lys Leu Met Gly Gly
            100                 105                 110

Leu Asp Met Leu Ile Leu Asn His Ile Thr Asn Thr Ser Leu Asn Leu
        115                 120                 125

Phe His Asp Asp Ile His His Val Arg Lys Ser Met Glu Val Asn Phe
    130                 135                 140

Leu Ser Tyr Val Val Leu Thr Val Ala Ala Leu Pro Met Leu Lys Gln
145                 150                 155                 160

Ser Asn Gly Ser Ile Val Val Ser Ser Leu Ala Gly Lys Val Ala
                165                 170                 175

Tyr Pro Met Val Ala Ala Tyr Ser Ala Ser Lys Phe Ala Leu Asp Gly
            180                 185                 190

Phe Phe Ser Ser Ile Arg Lys Glu Tyr Ser Val Ser Arg Val Asn Val
```

```
                195                 200                 205
Ser Ile Thr Leu Cys Val Leu Gly Leu Ile Asp Thr Glu Thr Ala Met
210                 215                 220

Lys Ala Val Ser Gly Ile Val His Met Gln Ala Pro Lys Glu Glu
225                 230                 235                 240

Cys Ala Leu Glu Ile Ile Lys Gly Gly Ala Leu Arg Gln Glu Val
                245                 250                 255

Tyr Tyr Asp Ser Ser Leu Trp Thr Thr Leu Leu Ile Arg Asn Pro Cys
                260                 265                 270

Arg Lys Ile Leu Glu Phe Leu Tyr Ser Thr Ser Tyr Asn Met Asp Arg
                275                 280                 285

Phe Ile Asn Lys
    290

<210> SEQ ID NO 28
<211> LENGTH: 398
<212> TYPE: PRT
<213> ORGANISM: Unknown
<220> FEATURE:
<223> OTHER INFORMATION: Rabbit

<400> SEQUENCE: 28

Gly Val Lys Thr Val Leu Leu Ile Gly Val Leu Gly Ala Tyr
1               5                   10                  15

Tyr Val Tyr Thr Pro Leu Pro Asp Asn Ile Glu Glu Pro Trp Arg Leu
                20                  25                  30

Leu Trp Val Asn Ala His Met Lys Thr Leu Thr Asn Leu Ala Leu Phe
                35                  40                  45

Ala Glu Tyr Leu Gly Ser Asn Ile Phe Met Asn Thr Val Lys Phe Leu
50                  55                  60

Thr Ser Phe Gln Glu Val Pro Pro Thr Ser Asp Glu Asn Val Thr Val
65                  70                  75                  80

Thr Glu Thr Thr Phe Asn Asn Val Pro Val Arg Val Tyr Val Pro Lys
                85                  90                  95

Arg Lys Ser Lys Thr Leu Arg Arg Gly Leu Phe Tyr Ile His Gly Gly
                100                 105                 110

Gly Trp Cys Val Gly Ser Ala Ala Leu Ser Gly Tyr Asp Leu Leu Ser
        115                 120                 125

Arg Arg Thr Ala Asp Arg Leu Asp Val Val Val Ser Thr Asn Tyr
130                 135                 140

Arg Leu Ala Pro Glu Tyr His Phe Pro Ile Gln Phe Glu Asp Val Tyr
145                 150                 155                 160

Asp Ala Leu Lys Trp Phe Leu Arg Gln Asp Val Leu Glu Lys Tyr Gly
                165                 170                 175

Val Asp Pro Glu Arg Val Gly Val Ser Gly Asp Ser Ala Gly Gly Asn
                180                 185                 190

Leu Ala Ala Ala Val Ala Gln Gln Leu Ile Lys Asp Pro Asp Val Lys
        195                 200                 205

Ile Lys Leu Lys Thr Gln Ser Leu Ile Tyr Pro Ala Leu Gln Thr Leu
        210                 215                 220

Asp Met Asp Leu Pro Ser Tyr Arg Glu Asn Ala Gln Phe Pro Ile Leu
225                 230                 235                 240

Ser Lys Ser Phe Met Val Arg Leu Trp Ser Glu Tyr Phe Thr Ser Asp
                245                 250                 255

Arg Ser Leu Glu Lys Ala Met Leu Leu Asn Gln His Val Pro Val Glu
                260                 265                 270
```

Ser Ser His Leu Phe Lys Phe Thr Asn Trp Ser Ser Leu Leu Pro Glu
            275                 280                 285

Lys Phe Lys Lys Gly His Val Tyr Asn Thr Pro Thr Tyr Gly Ser Ser
            290                 295                 300

Glu Leu Ala Arg Lys Tyr Pro Gly Phe Leu Asp Val Arg Ala Ala Pro
305                 310                 315                 320

Leu Leu Ala Asp Asp Ala Gln Leu Arg Gly Phe Pro Leu Thr Tyr Val
                325                 330                 335

Ile Thr Cys Gln Tyr Asp Val Leu Arg Asp Asp Gly Val Met Tyr Val
                340                 345                 350

Thr Arg Leu Arg Asn Ala Gly Val Gln Val Thr His Asn His Ile Glu
            355                 360                 365

Asp Gly Phe His Gly Ala Leu Ser Tyr Asn Gly Phe Lys Thr Gly Tyr
            370                 375                 380

Arg Val Glu Lys Gln Tyr Phe Glu Trp Leu Arg Glu Asn Val
385                 390                 395

<210> SEQ ID NO 29
<211> LENGTH: 399
<212> TYPE: PRT
<213> ORGANISM: Unknown
<220> FEATURE:
<223> OTHER INFORMATION: Rabbit

<400> SEQUENCE: 29

Met Gly Val Lys Thr Val Leu Leu Ile Val Gly Val Leu Gly Ala
1               5                   10                  15

Tyr Tyr Val Tyr Thr Pro Leu Pro Asp Asn Ile Glu Glu Pro Trp Arg
                20                  25                  30

Leu Leu Trp Val Asn Ala His Met Lys Thr Leu Thr Asn Leu Ala Leu
            35                  40                  45

Phe Ala Glu Tyr Leu Gly Ser Asn Ile Phe Met Asn Thr Val Lys Phe
50                  55                  60

Leu Thr Ser Phe Gln Glu Val Pro Pro Thr Ser Asp Glu Asn Val Thr
65                  70                  75                  80

Val Thr Glu Thr Thr Phe Asn Asn Val Pro Val Arg Val Tyr Val Pro
                85                  90                  95

Lys Arg Lys Ser Lys Thr Leu Arg Arg Gly Leu Phe Tyr Ile His Gly
            100                 105                 110

Gly Gly Trp Cys Val Gly Ser Ala Ala Leu Ser Gly Tyr Asp Leu Leu
            115                 120                 125

Ser Arg Arg Thr Ala Asp Arg Leu Asp Val Val Val Ser Thr Asn
130                 135                 140

Tyr Arg Leu Ala Pro Glu Tyr His Phe Pro Ile Gln Phe Glu Asp Val
145                 150                 155                 160

Tyr Asp Ala Leu Lys Trp Phe Leu Arg Gln Val Leu Glu Lys Tyr
                165                 170                 175

Gly Val Asp Pro Glu Arg Val Gly Val Ser Gly Asp Ser Ala Gly Gly
            180                 185                 190

Asn Leu Ala Ala Ala Val Ala Gln Gln Leu Ile Lys Asp Pro Asp Val
            195                 200                 205

Lys Ile Lys Leu Lys Thr Gln Ser Leu Ile Tyr Pro Ala Leu Gln Thr
            210                 215                 220

Leu Asp Met Asp Leu Pro Ser Tyr Arg Glu Asn Ala Gln Phe Pro Ile
225                 230                 235                 240

Leu Ser Lys Ser Phe Met Val Arg Leu Trp Ser Glu Tyr Phe Thr Ser
            245                 250                 255

Asp Arg Ser Leu Glu Lys Ala Met Leu Leu Asn Gln His Val Pro Val
            260                 265                 270

Glu Ser Ser His Leu Phe Lys Phe Thr Asn Trp Ser Ser Leu Leu Pro
            275                 280                 285

Glu Lys Phe Lys Lys Gly His Val Tyr Asn Thr Pro Thr Tyr Gly Ser
            290                 295                 300

Ser Glu Leu Ala Arg Lys Tyr Pro Gly Phe Leu Asp Val Arg Ala Ala
305                 310                 315                 320

Pro Leu Leu Ala Asp Asp Ala Gln Leu Arg Gly Phe Pro Leu Thr Tyr
                325                 330                 335

Val Ile Thr Cys Gln Tyr Asp Val Leu Arg Asp Asp Gly Val Met Tyr
                340                 345                 350

Val Thr Arg Leu Arg Asn Ala Gly Val Gln Val Thr His Asn His Ile
                355                 360                 365

Glu Asp Gly Phe His Gly Ala Leu Ser Tyr Asn Gly Phe Lys Thr Gly
                370                 375                 380

Tyr Arg Val Glu Lys Gln Tyr Phe Glu Trp Leu Arg Glu Asn Val
385                 390                 395

<210> SEQ ID NO 30
<211> LENGTH: 229
<212> TYPE: PRT
<213> ORGANISM: Unknown
<220> FEATURE:
<223> OTHER INFORMATION: Bovine

<400> SEQUENCE: 30

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser Thr Pro
            20                  25                  30

Val Cys Pro Asn Gly Pro Gly Asn Cys Gln Val Ser Leu Arg Asp Leu
            35                  40                  45

Phe Asp Arg Ala Val Met Val Ser His Tyr Ile His Asp Leu Ser Ser
        50                  55                  60

Glu Met Phe Asn Glu Phe Asp Lys Arg Tyr Ala Gln Gly Lys Gly Phe
65                  70                  75                  80

Ile Thr Met Ala Leu Asn Ser Cys His Thr Ser Ser Leu Pro Thr Pro
                85                  90                  95

Glu Asp Lys Glu Gln Ala Gln Gln Thr His His Glu Val Leu Met Ser
            100                 105                 110

Leu Ile Leu Gly Leu Leu Arg Ser Trp Asn Asp Pro Leu Tyr His Leu
            115                 120                 125

Val Thr Glu Val Arg Gly Met Lys Gly Ala Pro Asp Ala Ile Leu Ser
        130                 135                 140

Arg Ala Ile Glu Ile Glu Glu Glu Asn Lys Arg Leu Leu Glu Gly Met
145                 150                 155                 160

Glu Met Ile Phe Gly Gln Val Ile Pro Gly Ala Lys Glu Thr Glu Pro
                165                 170                 175

Tyr Pro Val Trp Ser Gly Leu Pro Ser Leu Gln Thr Lys Asp Glu Asp
            180                 185                 190

Ala Arg Tyr Ser Ala Phe Tyr Asn Leu Leu His Cys Leu Arg Arg Asp
            195                 200                 205

Ser Ser Lys Ile Asp Thr Tyr Leu Lys Leu Leu Asn Cys Arg Ile Ile

-continued

Tyr Asn Asn Asn Cys
225

<210> SEQ ID NO 31
<211> LENGTH: 216
<212> TYPE: PRT
<213> ORGANISM: Sus sp.

<400> SEQUENCE: 31

Met Ala Ala Gly Pro Arg Thr Ser Val Leu Leu Ala Phe Ala Leu Leu
1               5                   10                  15

Cys Leu Pro Trp Thr Gln Glu Val Gly Ala Phe Pro Ala Met Pro Leu
            20                  25                  30

Ser Ser Leu Phe Ala Asn Ala Val Leu Arg Ala Gln His Leu His Gln
        35                  40                  45

Leu Ala Ala Asp Thr Tyr Lys Glu Phe Glu Arg Ala Tyr Ile Pro Glu
    50                  55                  60

Gly Gln Arg Tyr Ser Ile Gln Asn Ala Gln Ala Ala Phe Cys Phe Ser
65                  70                  75                  80

Glu Thr Ile Pro Ala Pro Thr Gly Lys Asp Glu Ala Gln Gln Arg Ser
                85                  90                  95

Asp Val Glu Leu Leu Arg Phe Ser Leu Leu Leu Ile Gln Ser Trp Leu
            100                 105                 110

Gly Pro Val Gln Phe Leu Ser Arg Val Phe Thr Asn Ser Leu Val Phe
        115                 120                 125

Gly Thr Ser Asp Arg Val Tyr Glu Lys Leu Lys Asp Leu Glu Glu Gly
    130                 135                 140

Ile Gln Ala Leu Met Arg Glu Leu Glu Asp Gly Ser Pro Arg Ala Gly
145                 150                 155                 160

Gln Ile Leu Lys Gln Thr Tyr Asp Lys Phe Asp Thr Asn Leu Arg Ser
                165                 170                 175

Asp Asp Ala Leu Leu Lys Asn Tyr Gly Leu Leu Ser Cys Phe Lys Lys
            180                 185                 190

Asp Leu His Lys Ala Glu Thr Tyr Leu Arg Val Met Lys Cys Arg Arg
        195                 200                 205

Phe Val Glu Ser Ser Cys Ala Phe
    210                 215

<210> SEQ ID NO 32
<211> LENGTH: 317
<212> TYPE: PRT
<213> ORGANISM: Rattus sp.

<400> SEQUENCE: 32

Met Arg Leu Ala Val Val Cys Phe Cys Leu Phe Gly Leu Ala Ser Cys
1               5                   10                  15

Leu Pro Val Lys Val Ala Glu Phe Gly Ser Ser Glu Glu Lys Ala His
            20                  25                  30

Tyr Ser Lys His Ser Asp Ala Val Ala Thr Trp Leu Lys Pro Asp Pro
        35                  40                  45

Ser Gln Lys Gln Asn Leu Leu Ala Pro Gln Asn Ser Val Ser Ser Glu
    50                  55                  60

Glu Thr Asp Asp Phe Lys Gln Glu Thr Leu Pro Ser Asn Ser Asn Glu
65                  70                  75                  80

Ser His Asp His Met Asp Asp Asp Asp Asp Asp Asp Asp Gly Asp
                85                  90                  95

```
His Ala Glu Ser Glu Asp Ser Val Asn Ser Asp Glu Ser Asp Glu Ser
            100                 105                 110

His His Ser Asp Glu Ser Asp Glu Ser Phe Thr Ala Ser Thr Gln Ala
            115                 120                 125

Asp Val Leu Thr Pro Ile Ala Pro Thr Val Asp Val Pro Asp Gly Arg
130                 135                 140

Gly Asp Ser Leu Ala Tyr Gly Leu Arg Ser Lys Ser Arg Ser Phe Pro
145                 150                 155                 160

Val Ser Asp Glu Gln Tyr Pro Asp Ala Thr Asp Glu Asp Leu Thr Ser
            165                 170                 175

Arg Met Lys Ser Gln Glu Ser Asp Glu Ala Leu Lys Val Ile Pro Val
            180                 185                 190

Ala Gln Arg Leu Ser Val Pro Ser Asp Gln Asp Ser Asn Gly Lys Thr
            195                 200                 205

Ser His Glu Ser Ser Gln Leu Asp Glu Pro Ser Val Glu Thr His Ser
            210                 215                 220

Leu Glu Gln Ser Lys Glu Tyr Lys Gln Arg Ala Ser His Glu Ser Thr
225                 230                 235                 240

Glu Gln Ser Asp Ala Ile Asp Ser Ala Glu Lys Pro Asp Ala Ile Asp
                245                 250                 255

Ser Ala Glu Arg Ser Asp Ala Ile Asp Ser Gln Ala Ser Ser Lys Ala
            260                 265                 270

Ser Leu Glu His Gln Ser His Glu Phe His Ser His Glu Asp Lys Leu
            275                 280                 285

Val Leu Asp Pro Lys Ser Lys Glu Asp Asp Arg Tyr Leu Lys Phe Arg
            290                 295                 300

Ile Ser His Glu Leu Glu Ser Ser Ser Glu Val Asn
305                 310                 315

<210> SEQ ID NO 33
<211> LENGTH: 254
<212> TYPE: PRT
<213> ORGANISM: Unknown
<220> FEATURE:
<223> OTHER INFORMATION: Hamster

<400> SEQUENCE: 33

Met Ala Asn Leu Ser Tyr Trp Leu Leu Ala Leu Phe Val Ala Thr Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly
50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Thr His
                85                  90                  95

Asn Gln Trp Asn Lys Pro Asn Lys Pro Lys Thr Ser Met Lys His Met
            100                 105                 110

Ala Gly Ala Ala Ala Ala Gly Ala Val Val Gly Leu Gly Gly Tyr
            115                 120                 125

Met Leu Gly Ser Ala Met Ser Arg Pro Met Leu His Phe Gly Asn Asp
130                 135                 140
```

```
Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Gln Asn Asn Phe Val
            165                 170                 175

His Asp Cys Val Asn Ile Thr Ile Lys Gln His Thr Val Thr Thr Thr
        180                 185                 190

Thr Lys Gly Glu Asn Phe Thr Glu Thr Asp Val Lys Met Met Glu Arg
            195                 200                 205

Val Val Glu Gln Met Cys Val Thr Gln Tyr Gln Lys Glu Ser Gln Ala
210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Ile Val Gly
            245                 250

<210> SEQ ID NO 34
<211> LENGTH: 167
<212> TYPE: PRT
<213> ORGANISM: Sus sp.

<400> SEQUENCE: 34

Met Arg Cys Gly Pro Leu Cys Arg Phe Leu Trp Leu Trp Pro Tyr Leu
1               5                   10                  15

Ser Tyr Val Glu Ala Val Pro Ile Trp Arg Val Gln Asp Asp Thr Lys
            20                  25                  30

Thr Leu Ile Lys Thr Ile Val Thr Arg Ile Ser Asp Ile Ser His Met
        35                  40                  45

Gln Ser Val Ser Ser Lys Gln Arg Val Thr Gly Leu Asp Phe Ile Pro
50                  55                  60

Gly Leu His Pro Val Leu Ser Leu Ser Lys Met Asp Gln Thr Leu Ala
65                  70                  75                  80

Ile Tyr Gln Gln Ile Leu Thr Ser Leu Pro Ser Arg Asn Val Ile Gln
                85                  90                  95

Ile Ser Asn Asp Leu Glu Asn Leu Arg Asp Leu Leu His Leu Leu Ala
            100                 105                 110

Ser Ser Lys Ser Cys Pro Leu Pro Gln Arg Arg Ala Leu Glu Thr Leu
        115                 120                 125

Glu Ser Leu Gly Gly Val Leu Glu Ala Ser Leu Tyr Ser Thr Glu Val
130                 135                 140

Val Ala Leu Ser Arg Leu Gln Gly Ala Leu Gln Asp Met Leu Arg Gln
145                 150                 155                 160

Leu Asp Leu Ser Pro Gly Cys
                165

<210> SEQ ID NO 35
<211> LENGTH: 485
<212> TYPE: PRT
<213> ORGANISM: Homo sapiens

<400> SEQUENCE: 35

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
```

-continued

```
                50                  55                  60
Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
                100                 105                 110

Leu Gly Phe Arg Ile Tyr Gly Met His Ser Glu Leu Trp Gly Val Val
                115                 120                 125

His Gly Ala Thr Val Leu Ser Pro Thr Ala Val Phe Gly Thr Leu Ala
130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
                180                 185                 190

Ala Gln Gly Arg Ala Asp Ser Gln Ala Gln Leu Leu Leu Ser Thr Val
                195                 200                 205

Val Gly Val Phe Thr Ala Pro Gly Leu His Leu Lys Gln Pro Phe Val
210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Thr Gly Ala Ser Val
                260                 265                 270

Asp Ser Thr Leu Ala Phe Asn Thr Tyr Val His Phe Gln Gly Lys Met
                275                 280                 285

Lys Gly Phe Ser Leu Leu Ala Glu Pro Gln Glu Phe Trp Val Asp Asn
                290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Ser Phe
                325                 330                 335

Thr Glu Ser Ala Cys Leu Leu Leu Ile Gln Pro His Tyr Ala Ser Asp
                340                 345                 350

Leu Asp Lys Val Glu Gly Leu Thr Phe Gln Gln Asn Ser Leu Asn Trp
                355                 360                 365

Met Lys Lys Leu Ser Pro Arg Thr Ile His Leu Thr Met Pro Gln Leu
370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
                420                 425                 430

Glu Ala Asp Glu Arg Glu Pro Thr Glu Ser Thr Gln Gln Leu Asn Lys
                435                 440                 445

Pro Glu Val Leu Glu Val Thr Leu Asn Arg Pro Phe Leu Phe Ala Val
                450                 455                 460

Tyr Asp Gln Ser Ala Thr Ala Leu His Phe Leu Gly Arg Val Ala Asn
465                 470                 475                 480
```

```
Pro Leu Ser Thr Ala
            485

<210> SEQ ID NO 36
<211> LENGTH: 150
<212> TYPE: PRT
<213> ORGANISM: Sus sp.

<400> SEQUENCE: 36

Met Ser Ser Phe Thr Ile Thr Val Ser Phe Leu Leu Val Leu Val Phe
1               5                   10                  15

Gln Phe Pro Gly Gln Thr Arg Ala Asn Pro Val Tyr Gly Ser Val Ser
            20                  25                  30

Asn Ala Asp Leu Met Asp Phe Lys Asn Leu Leu Asp His Leu Glu Asp
        35                  40                  45

Lys Met Pro Leu Glu Asp Glu Ala Met Pro Pro Gln Val Leu Ser Glu
    50                  55                  60

Gln Asn Glu Glu Val Gly Ala Pro Leu Ser Pro Leu Leu Glu Val Pro
65                  70                  75                  80

Pro Trp Thr Gly Glu Val Asn Pro Ala Gln Arg Asp Gly Gly Ala Leu
                85                  90                  95

Gly Arg Gly Pro Trp Asp Ala Ser Asp Arg Ser Ala Leu Leu Lys Ser
            100                 105                 110

Lys Leu Arg Ala Leu Leu Ala Ala Pro Arg Ser Leu Arg Arg Ser Ser
        115                 120                 125

Cys Phe Gly Gly Arg Met Asp Arg Ile Gly Ala Gln Ser Gly Leu Gly
    130                 135                 140

Cys Asn Ser Phe Arg Tyr
145                 150

<210> SEQ ID NO 37
<211> LENGTH: 166
<212> TYPE: PRT
<213> ORGANISM: Sus sp.

<400> SEQUENCE: 37

Met Ser Tyr Thr Thr Tyr Phe Leu Ala Phe Gln Leu Cys Val Thr Leu
1               5                   10                  15

Cys Phe Ser Gly Ser Tyr Cys Gln Ala Pro Phe Phe Lys Glu Ile Thr
            20                  25                  30

Ile Leu Lys Asp Tyr Phe Asn Ala Ser Thr Ser Asp Val Pro Asn Gly
        35                  40                  45

Gly Pro Leu Phe Leu Glu Ile Leu Lys Asn Trp Lys Glu Glu Ser Asp
    50                  55                  60

Lys Lys Ile Ile Gln Ser Gln Ile Val Ser Phe Tyr Phe Lys Phe Phe
65                  70                  75                  80

Glu Ile Phe Lys Asp Asn Gln Ala Ile Gln Arg Ser Met Asp Val Ile
                85                  90                  95

Lys Gln Asp Met Phe Gln Arg Phe Leu Asn Gly Ser Ser Gly Lys Leu
            100                 105                 110

Asn Asp Phe Glu Lys Leu Ile Lys Ile Pro Val Asp Asn Leu Gln Ile
        115                 120                 125

Gln Arg Lys Ala Ile Ser Glu Leu Ile Lys Val Met Asn Asp Leu Ser
    130                 135                 140

Pro Arg Ser Asn Leu Arg Lys Arg Lys Arg Ser Gln Thr Met Phe Gln
145                 150                 155                 160

Gly Gln Arg Ala Ser Lys
```

<210> SEQ ID NO 38
<211> LENGTH: 485
<212> TYPE: PRT
<213> ORGANISM: Rattus sp.

<400> SEQUENCE: 38

```
Met Ala Asn Arg Arg Gly Gly Gln Gly Gln Pro Pro Ser Val Ser
1               5                  10                  15

Pro Ser Pro Gly Ser Ser Gly Ser Leu Ser Thr Asp Arg Thr Cys Thr
                20                  25                  30

His Asn Ile Cys Met Val Ser Asp Phe Phe Tyr Pro Asn Met Gly Gly
                35                  40                  45

Val Glu Ser His Ile Tyr Gln Leu Ser Gln Cys Leu Ile Glu Arg Gly
    50                  55                  60

His Lys Val Ile Thr Val Thr His Ala Tyr Gly Asn Arg Lys Gly Val
65                  70                  75                  80

Arg Tyr Leu Thr Asn Gly Leu Lys Val Tyr Tyr Leu Pro Leu Arg Val
                85                  90                  95

Met Tyr Asn Gln Ser Thr Ala Thr Thr Leu Phe His Ser Leu Pro Leu
                100                 105                 110

Leu Arg Tyr Ile Phe Val Arg Glu Arg Ile Thr Ile Ile His Ser His
                115                 120                 125

Ser Ser Phe Ser Ala Met Ala His Asp Ala Leu Phe His Ala Lys Thr
                130                 135                 140

Met Gly Leu Gln Thr Val Phe Thr Asp His Ser Leu Phe Gly Phe Ala
145                 150                 155                 160

Asp Val Ser Ser Val Leu Thr Asn Lys Leu Leu Thr Val Ser Leu Cys
                165                 170                 175

Asp Thr Asn His Ile Ile Cys Val Ser Tyr Thr Ser Lys Glu Asn Thr
                180                 185                 190

Val Leu Arg Ala Ala Leu Asn Pro Glu Ile Val Ser Val Ile Pro Asn
                195                 200                 205

Ala Val Asp Pro Thr Asp Phe Thr Pro Glu Pro Phe Arg Arg His Asp
    210                 215                 220

Ser Val Ile Thr Val Val Val Ser Arg Leu Val Tyr Arg Lys Gly
225                 230                 235                 240

Thr Asp Leu Leu Ser Gly Ile Ile Pro Glu Leu Cys Gln Lys Tyr Gln
                245                 250                 255

Glu Leu Asn Phe Leu Ile Gly Gly Glu Gly Pro Lys Arg Ile Ile Leu
                260                 265                 270

Glu Glu Val Arg Glu Arg Tyr Gln Leu His Asp Arg Val Gln Leu Leu
                275                 280                 285

Gly Ala Leu Glu His Lys Asp Val Arg Asn Val Leu Val Gln Gly His
    290                 295                 300

Ile Phe Leu Asn Thr Ser Leu Thr Glu Ala Phe Cys Met Ala Ile Val
305                 310                 315                 320

Glu Ala Ala Ser Cys Gly Leu Gln Val Val Ser Thr Lys Val Gly Gly
                325                 330                 335

Ile Pro Glu Val Leu Pro Glu Asn Leu Ile Leu Cys Glu Pro Ser
                340                 345                 350

Val Lys Ser Leu Cys Glu Gly Leu Glu Lys Ala Ile Phe Gln Val Lys
                355                 360                 365

Ser Gly Thr Leu Pro Ala Pro Glu Asn Ile His Asn Val Val Lys Thr
```

```
                    370                 375                 380
Phe Tyr Thr Trp Arg Asn Val Ala Glu Arg Thr Glu Lys Val Tyr Glu
385                 390                 395                 400

Arg Val Ser Lys Glu Ser Val Leu Pro Met His Lys Arg Leu Asp Arg
                405                 410                 415

Leu Ile Ser His Cys Gly Pro Val Thr Gly Tyr Ile Phe Ala Leu Leu
                420                 425                 430

Ala Val Leu Ser Tyr Leu Phe Leu Ile Phe Leu Gln Trp Met Thr Pro
                435                 440                 445

Asp Ser Val Ile Asp Val Ala Ile Asp Ala Thr Gly Pro Arg Arg Ala
                450                 455                 460

Trp Thr His Gln Trp Pro Arg Asp Lys Lys Arg Asp Glu Asn Asp Lys
465                 470                 475                 480

Val Ser Lys Ser Arg
                485

<210> SEQ ID NO 39
<211> LENGTH: 91
<212> TYPE: PRT
<213> ORGANISM: artificial sequence
<220> FEATURE:
<223> OTHER INFORMATION: Synthetic

<400> SEQUENCE: 39

Ser Thr Ile Leu Arg Leu Ile Phe Ser Val Gly Leu Gln Pro Thr Leu
1               5                   10                  15

Phe Leu Leu Gly Ala Phe Asn Val Cys Asn Lys Ile Ile Phe Leu Met
                20                  25                  30

Ser Phe Val Gly Asn Cys Gly Thr Phe Thr Arg Gly Tyr Arg Ala Met
            35                  40                  45

Val Leu Asp Val Glu Phe Leu Tyr His Leu Leu Tyr Leu Leu Ile Cys
        50                  55                  60

Ala Met Gly Leu Phe Val His Glu Phe Phe Tyr Ser Leu Leu Leu Phe
65                  70                  75                  80

Asp Leu Val Tyr Arg Glu Glu Thr Leu Leu Asn
                85                  90

<210> SEQ ID NO 40
<211> LENGTH: 160
<212> TYPE: PRT
<213> ORGANISM: artificial sequence
<220> FEATURE:
<223> OTHER INFORMATION: Synthetic

<400> SEQUENCE: 40

Lys Ser Val Thr Arg Asn Gly Arg Pro Ile Ile Leu Thr Ala Ala Leu
1               5                   10                  15

Ala Leu Ile Leu Val Tyr Leu Phe Ser Ile Val Gly Tyr Leu Phe Phe
                20                  25                  30

Lys Asp Asp Phe Ile Leu Glu Val Asp Arg Leu Pro Asn Glu Thr Ala
            35                  40                  45

Gly Pro Glu Thr Gly Glu Ser Leu Ala Asn Asp Phe Leu Tyr Ser Asp
        50                  55                  60

Val Cys Arg Val Glu Thr Gly Glu Asn Cys Thr Ser Pro Ala Pro Lys
65                  70                  75                  80

Glu Glu Leu Leu Pro Val Glu Glu Thr Glu Gln Asp Lys Glu His Thr
                85                  90                  95

Cys Glu Thr Leu Leu Met Cys Ile Val Thr Val Leu Ser His Gly Leu
```

```
                    100                 105                 110
Arg Ser Gly Gly Gly Val Gly Asp Val Leu Arg Lys Pro Ser Lys Glu
        115                 120                 125

Glu Pro Leu Phe Ala Ala Arg Val Ile Tyr Asp Leu Leu Phe Phe Phe
        130                 135                 140

Met Val Ile Ile Ile Val Leu Asn Leu Ile Phe Gly Val Ile Ile Asp
145                 150                 155                 160

<210> SEQ ID NO 41
<211> LENGTH: 50
<212> TYPE: PRT
<213> ORGANISM: artificial sequence
<220> FEATURE:
<223> OTHER INFORMATION: Synthetic

<400> SEQUENCE: 41

Asp Arg Leu Ile Ser His Cys Gly Pro Val Thr Gly Tyr Ile Phe Ala
1               5                   10                  15

Leu Leu Ala Val Leu Ser Tyr Leu Phe Leu Ile Phe Leu Gln Trp Met
            20                  25                  30

Thr Pro Asp Ser Val Ile Asp Val Ala Ile Asp Ala Thr Gly Pro Arg
        35                  40                  45

Arg Ala
    50

<210> SEQ ID NO 42
<211> LENGTH: 58
<212> TYPE: PRT
<213> ORGANISM: artificial sequence
<220> FEATURE:
<223> OTHER INFORMATION: Synthetic

<400> SEQUENCE: 42

Asp Arg Leu Ile Ser His Cys Gly Pro Val Thr Gly Tyr Ile Phe Ala
1               5                   10                  15

Leu Leu Ala Val Leu Ser Tyr Leu Phe Leu Ile Phe Leu Gln Trp Met
            20                  25                  30

Thr Pro Asp Ser Val Ile Asp Val Ala Ile Asp Ala Thr Gly Pro Arg
        35                  40                  45

Arg Ala Trp Thr His Gln Trp Pro Arg Asp
    50                  55

<210> SEQ ID NO 43
<211> LENGTH: 139
<212> TYPE: PRT
<213> ORGANISM: artificial sequence
<220> FEATURE:
<223> OTHER INFORMATION: Synthetic

<400> SEQUENCE: 43

Met Glu Ala Met Trp Leu Leu Cys Val Ala Leu Ala Val Leu Ala Trp
1               5                   10                  15

Gly Phe Leu Trp Val Trp Asp Ser Ser Glu Arg Met Lys Ser Arg Glu
            20                  25                  30

Gln Gly Gly Arg Leu Gly Ala Glu Ser Arg Thr Leu Leu Val Ile Ala
        35                  40                  45

His Pro Asp Asp Glu Ala Met Phe Phe Ala Pro Thr Val Leu Gly Leu
    50                  55                  60

Ala Arg Leu Arg His Trp Val Tyr Leu Leu Cys Phe Ser Ala Gly Asn
65                  70                  75                  80
```

```
Tyr Tyr Asn Gln Gly Glu Thr Arg Lys Lys Glu Leu Leu Gln Ser Cys
            85                  90                  95

Asp Val Leu Gly Ile Pro Leu Ser Ser Val Met Ile Ile Asp Asn Arg
            100                 105                 110

Asp Phe Pro Asp Pro Gly Met Gln Trp Thr Glu His Val Ala
        115                 120                 125

Arg Val Leu Leu Gln His Ile Glu Val Asn Gly
        130                 135

<210> SEQ ID NO 44
<211> LENGTH: 45
<212> TYPE: PRT
<213> ORGANISM: artificial sequence
<220> FEATURE:
<223> OTHER INFORMATION: Synthetic

<400> SEQUENCE: 44

Met Glu Ala Met Trp Leu Leu Cys Val Ala Leu Ala Val Leu Ala Trp
1               5                   10                  15

Gly Phe Leu Trp Val Trp Asp Ser Ser Glu Arg Met Lys Ser Arg Glu
            20                  25                  30

Gln Gly Gly Arg Leu Gly Ala Glu Ser Arg Thr Leu Leu
        35                  40                  45

<210> SEQ ID NO 45
<211> LENGTH: 65
<212> TYPE: PRT
<213> ORGANISM: artificial sequence
<220> FEATURE:
<223> OTHER INFORMATION: Synthetic

<400> SEQUENCE: 45

Val Leu Ala Ala Gly Leu Val Leu Ser Val Phe Val Ala Ile Gly Glu
1               5                   10                  15

Phe Leu Tyr Lys Ser Arg Lys Asn Asn Asp Val Glu Gln Cys Leu Ser
            20                  25                  30

Phe Asn Ala Ile Met Glu Glu Leu Gly Ile Ser Leu Lys Asn Gln Lys
        35                  40                  45

Lys Leu Lys Lys Lys Ser Arg Thr Lys Gly Lys Ser Ser Phe Thr Ser
    50                  55                  60
Ile
65

<210> SEQ ID NO 46
<211> LENGTH: 84
<212> TYPE: PRT
<213> ORGANISM: artificial sequence
<220> FEATURE:
<223> OTHER INFORMATION: Synthetic

<400> SEQUENCE: 46

Gly Ile Phe Ile Val Leu Ala Ala Gly Leu Val Leu Ser Val Phe Val
1               5                   10                  15

Ala Ile Gly Glu Phe Leu Tyr Lys Ser Arg Lys Asn Asn Asp Val Glu
            20                  25                  30

Gln Cys Leu Ser Phe Asn Ala Ile Met Glu Glu Leu Gly Ile Ser Leu
        35                  40                  45

Lys Asn Gln Lys Lys Leu Lys Lys Lys Ser Arg Thr Lys Gly Lys Ser
    50                  55                  60

Ser Phe Thr Ser Ile Leu Thr Cys His Gln Arg Arg Thr Gln Arg Lys
65                  70                  75                  80
```

Glu Thr Val Ala

<210> SEQ ID NO 47
<211> LENGTH: 31
<212> TYPE: PRT
<213> ORGANISM: artificial sequence
<220> FEATURE:
<223> OTHER INFORMATION: Synthetic

<400> SEQUENCE: 47

Trp Gly Val Leu Ala Gly Ile Ala Tyr Phe Ser Met Val Gly Asn Trp
1               5                   10                  15

Ala Lys Val Leu Val Val Leu Leu Leu Phe Ala Gly Val Asp Ala
            20                  25                  30

<210> SEQ ID NO 48
<211> LENGTH: 15
<212> TYPE: PRT
<213> ORGANISM: artificial sequence
<220> FEATURE:
<223> OTHER INFORMATION: Synthetic

<400> SEQUENCE: 48

Lys Tyr Lys Ser Arg Arg Ser Phe Ile Glu Glu Lys Lys Met Pro
1               5                   10                  15

<210> SEQ ID NO 49
<211> LENGTH: 37
<212> TYPE: PRT
<213> ORGANISM: artificial sequence
<220> FEATURE:
<223> OTHER INFORMATION: Synthetic

<400> SEQUENCE: 49

Gly Thr Phe Cys Cys Thr Ala Met Leu Ile Thr Val Leu Ala Leu Val
1               5                   10                  15

Cys Thr Leu Leu Tyr Ile Lys Tyr Lys Ser Arg Arg Ser Phe Ile Glu
            20                  25                  30

Glu Lys Lys Met Pro
        35

<210> SEQ ID NO 50
<211> LENGTH: 29
<212> TYPE: PRT
<213> ORGANISM: artificial sequence
<220> FEATURE:
<223> OTHER INFORMATION: Synthetic

<400> SEQUENCE: 50

Met Asp Pro Val Val Leu Gly Leu Cys Leu Ser Cys Leu Leu Leu
1               5                   10                  15

Leu Ser Leu Trp Lys Gln Ser Tyr Gly Gly Lys Leu
            20                  25

<210> SEQ ID NO 51
<211> LENGTH: 63
<212> TYPE: PRT
<213> ORGANISM: artificial sequence
<220> FEATURE:
<223> OTHER INFORMATION: Synthetic

<400> SEQUENCE: 51

Asn Leu Pro Thr Pro Asp Phe Ser Met Pro Tyr Asn Val Ile Cys Leu
1               5                   10                  15

```
Thr Cys Thr Val Val Ala Val Cys Tyr Gly Ser Phe Tyr Asn Leu Leu
            20                  25                  30

Thr Arg Thr Phe His Ile Glu Glu Pro Arg Thr Gly Leu Ala Lys
        35                  40                  45

Arg Leu Ala Asn Leu Ile Arg Arg Ala Arg Gly Val Pro Pro Leu
    50                  55                  60

<210> SEQ ID NO 52
<211> LENGTH: 35
<212> TYPE: PRT
<213> ORGANISM: artificial sequence
<220> FEATURE:
<223> OTHER INFORMATION: Synthetic

<400> SEQUENCE: 52

Ile Thr Thr Val Glu Ser Asn Ser Ser Trp Trp Thr Asn Trp Val Ile
1               5                   10                  15

Pro Ala Ile Ser Ala Leu Val Val Ala Leu Met Tyr Arg Leu Tyr Met
            20                  25                  30

Ala Glu Asp
        35

<210> SEQ ID NO 53
<211> LENGTH: 31
<212> TYPE: PRT
<213> ORGANISM: artificial sequence
<220> FEATURE:
<223> OTHER INFORMATION: Synthetic

<400> SEQUENCE: 53

Glu Ser Asn Ser Ser Trp Trp Thr Asn Trp Val Ile Pro Ala Ile Ser
1               5                   10                  15

Ala Leu Val Val Ala Leu Met Tyr Arg Leu Tyr Met Ala Glu Asp
            20                  25                  30

<210> SEQ ID NO 54
<211> LENGTH: 63
<212> TYPE: PRT
<213> ORGANISM: artificial sequence
<220> FEATURE:
<223> OTHER INFORMATION: Synthetic

<400> SEQUENCE: 54

Met Gly Cys Lys Thr Gly Pro Lys Pro Phe Gly Gly Glu Thr Ile
1               5                   10                  15

Arg Pro Ile Arg Ile Arg Arg Cys Ser Tyr Phe Thr Ser Thr Asp Ser
            20                  25                  30

Lys Met Ala Ile Gln Leu Arg Ser Pro Phe Pro Leu Ala Leu Pro Gly
        35                  40                  45

Met Leu Ala Leu Leu Gly Trp Trp Trp Phe Phe Ser Arg Lys Lys
    50                  55                  60

<210> SEQ ID NO 55
<211> LENGTH: 63
<212> TYPE: PRT
<213> ORGANISM: artificial sequence
<220> FEATURE:
<223> OTHER INFORMATION: Synthetic

<400> SEQUENCE: 55

Met Gly Cys Lys Thr Gly Pro Lys Pro Phe Gly Gly Glu Thr Ile
1               5                   10                  15

Arg Pro Ile Arg Ile Arg Arg Cys Ser Tyr Phe Thr Ser Thr Asp Ser
```

```
                20                  25                  30

Lys Leu Ala Ile Gln Leu Arg Ser Pro Phe Pro Leu Ala Leu Pro Gly
         35                  40                  45

Leu Leu Ala Leu Leu Gly Trp Trp Phe Phe Ser Arg Lys Lys
     50                  55                  60

<210> SEQ ID NO 56
<211> LENGTH: 23
<212> TYPE: PRT
<213> ORGANISM: artificial sequence
<220> FEATURE:
<223> OTHER INFORMATION: Synthetic

<400> SEQUENCE: 56

Met Lys Lys Tyr Leu Leu Pro Ile Leu Gly Leu Phe Met Ala Tyr Tyr
1               5                   10                  15

Tyr Tyr Ser Ala Asn Glu Glu
            20

<210> SEQ ID NO 57
<211> LENGTH: 23
<212> TYPE: PRT
<213> ORGANISM: artificial sequence
<220> FEATURE:
<223> OTHER INFORMATION: Synthetic

<400> SEQUENCE: 57

Met Lys Lys Tyr Leu Leu Pro Leu Leu Gly Leu Phe Leu Ala Tyr Tyr
1               5                   10                  15

Tyr Tyr Ser Ala Asn Glu Glu
            20

<210> SEQ ID NO 58
<211> LENGTH: 26
<212> TYPE: PRT
<213> ORGANISM: artificial sequence
<220> FEATURE:
<223> OTHER INFORMATION: Synthetic

<400> SEQUENCE: 58

Met Ala Phe Met Lys Lys Tyr Leu Leu Pro Ile Leu Gly Leu Phe Met
1               5                   10                  15

Ala Tyr Tyr Tyr Tyr Ser Ala Asn Glu Glu
            20                  25

<210> SEQ ID NO 59
<211> LENGTH: 33
<212> TYPE: PRT
<213> ORGANISM: artificial sequence
<220> FEATURE:
<223> OTHER INFORMATION: Synthetic

<400> SEQUENCE: 59

Gly Val Lys Thr Val Leu Leu Ile Val Gly Val Leu Gly Ala Tyr
1               5                   10                  15

Tyr Val Tyr Thr Pro Leu Pro Asp Asn Ile Glu Pro Trp Arg Leu
            20                  25                  30

Leu

<210> SEQ ID NO 60
<211> LENGTH: 34
<212> TYPE: PRT
<213> ORGANISM: artificial sequence
<220> FEATURE:
```

<223> OTHER INFORMATION: Synthetic

<400> SEQUENCE: 60

Met Gly Val Lys Thr Val Leu Leu Ile Val Gly Val Leu Gly Ala
1               5                   10                  15

Tyr Tyr Val Tyr Thr Pro Leu Pro Asp Asn Ile Glu Glu Pro Trp Arg
            20                  25                  30

Leu Leu

<210> SEQ ID NO 61
<211> LENGTH: 30
<212> TYPE: PRT
<213> ORGANISM: artificial sequence
<220> FEATURE:
<223> OTHER INFORMATION: Synthetic

<400> SEQUENCE: 61

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 62
<211> LENGTH: 26
<212> TYPE: PRT
<213> ORGANISM: artificial sequence
<220> FEATURE:
<223> OTHER INFORMATION: Synthetic

<400> SEQUENCE: 62

Met Ala Ala Gly Pro Arg Thr Ser Ala Leu Leu Ala Phe Ala Leu Leu
1               5                   10                  15

Cys Leu Pro Trp Thr Arg Glu Val Gly Ala
            20                  25

<210> SEQ ID NO 63
<211> LENGTH: 26
<212> TYPE: PRT
<213> ORGANISM: artificial sequence
<220> FEATURE:
<223> OTHER INFORMATION: Synthetic

<400> SEQUENCE: 63

Met Ala Ala Gly Pro Arg Thr Ser Val Leu Leu Ala Phe Ala Leu Leu
1               5                   10                  15

Cys Leu Pro Trp Thr Arg Glu Val Gly Ala
            20                  25

<210> SEQ ID NO 64
<211> LENGTH: 16
<212> TYPE: PRT
<213> ORGANISM: artificial sequence
<220> FEATURE:
<223> OTHER INFORMATION: Synthetic

<400> SEQUENCE: 64

Met Arg Leu Ala Val Val Cys Leu Cys Leu Phe Gly Leu Ala Ser Cys
1               5                   10                  15

<210> SEQ ID NO 65
<211> LENGTH: 22
<212> TYPE: PRT
<213> ORGANISM: artificial sequence
<220> FEATURE:
<223> OTHER INFORMATION: Synthetic -continued

```
<400> SEQUENCE: 65

Met Ala Asn Leu Ser Tyr Trp Leu Leu Ala Leu Phe Val Ala Met Trp
1               5                   10                  15

Thr Asp Val Gly Leu Cys
            20

<210> SEQ ID NO 66
<211> LENGTH: 21
<212> TYPE: PRT
<213> ORGANISM: Unknown
<220> FEATURE:
<223> OTHER INFORMATION: Porcine

<400> SEQUENCE: 66

Met Arg Cys Gly Pro Leu Cys Arg Phe Leu Trp Leu Trp Pro Tyr Leu
1               5                   10                  15

Ser Tyr Val Glu Ala
            20

<210> SEQ ID NO 67
<211> LENGTH: 33
<212> TYPE: PRT
<213> ORGANISM: artificial sequence
<220> FEATURE:
<223> OTHER INFORMATION: Synthetic

<400> SEQUENCE: 67

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly

<210> SEQ ID NO 68
<211> LENGTH: 28
<212> TYPE: PRT
<213> ORGANISM: artificial sequence
<220> FEATURE:
<223> OTHER INFORMATION: Synthetic

<400> SEQUENCE: 68

Met Ser Ser Phe Thr Ile Thr Val Ser Phe Leu Leu Val Leu Val Phe
1               5                   10                  15

Gln Phe Pro Gly Gln Thr Arg Ala Asn Pro Val Tyr
            20                  25

<210> SEQ ID NO 69
<211> LENGTH: 17
<212> TYPE: PRT
<213> ORGANISM: artificial sequence
<220> FEATURE:
<223> OTHER INFORMATION: Synthetic

<400> SEQUENCE: 69

Met Ser Tyr Thr Thr Tyr Phe Leu Ala Phe Gln Leu Cys Val Thr Leu
1               5                   10                  15

Cys

<210> SEQ ID NO 70
<211> LENGTH: 33
<212> TYPE: PRT
<213> ORGANISM: artificial sequence
<220> FEATURE:
<223> OTHER INFORMATION: Synthetic
```

```
<400> SEQUENCE: 70

Ala Phe Glu Arg Ser Ser Leu Leu Ala Arg Ile Ser Ile Gln Lys Asp
1               5                   10                  15

Gly Cys Gln Cys Val Leu Phe Ser Ser His Phe Met Pro Arg Leu Leu
            20                  25                  30

Met

<210> SEQ ID NO 71
<211> LENGTH: 8
<212> TYPE: PRT
<213> ORGANISM: artificial sequence
<220> FEATURE:
<223> OTHER INFORMATION: Synthetic

<400> SEQUENCE: 71

Cys Gln Cys Val Leu Phe Ser Ser
1               5

<210> SEQ ID NO 72
<211> LENGTH: 4
<212> TYPE: PRT
<213> ORGANISM: artificial sequence
<220> FEATURE:
<223> OTHER INFORMATION: Synthetic

<400> SEQUENCE: 72

Cys Val Leu Phe
1

<210> SEQ ID NO 73
<211> LENGTH: 12
<212> TYPE: PRT
<213> ORGANISM: artificial sequence
<220> FEATURE:
<223> OTHER INFORMATION: Synthetic

<400> SEQUENCE: 73

Arg Ser Gln Gln Glu Ala Ala Ala Lys Lys Ala Ala
1               5                   10

<210> SEQ ID NO 74
<211> LENGTH: 4
<212> TYPE: PRT
<213> ORGANISM: artificial sequence
<220> FEATURE:
<223> OTHER INFORMATION: Synthetic

<400> SEQUENCE: 74

Lys Lys Ala Ala
1

<210> SEQ ID NO 75
<211> LENGTH: 4
<212> TYPE: PRT
<213> ORGANISM: artificial sequence
<220> FEATURE:
<223> OTHER INFORMATION: Synthetic

<400> SEQUENCE: 75

Lys Asp Glu Leu
1

<210> SEQ ID NO 76
<211> LENGTH: 4
<212> TYPE: PRT
<213> ORGANISM: artificial sequence
```

```
<220> FEATURE:
<223> OTHER INFORMATION: Synthetic

<400> SEQUENCE: 76

His Asp Glu Leu
1

<210> SEQ ID NO 77
<211> LENGTH: 4
<212> TYPE: PRT
<213> ORGANISM: artificial sequence
<220> FEATURE:
<223> OTHER INFORMATION: Synthetic

<400> SEQUENCE: 77

Arg Asp Glu Leu
1

<210> SEQ ID NO 78
<211> LENGTH: 4
<212> TYPE: PRT
<213> ORGANISM: artificial sequence
<220> FEATURE:
<223> OTHER INFORMATION: Synthetic

<400> SEQUENCE: 78

Phe Gly Ala Gly
1

<210> SEQ ID NO 79
<211> LENGTH: 7
<212> TYPE: PRT
<213> ORGANISM: artificial sequence
<220> FEATURE:
<223> OTHER INFORMATION: Synthetic

<400> SEQUENCE: 79

Glu Phe Gly Gly Gly Gly Gly
1               5

<210> SEQ ID NO 80
<211> LENGTH: 5
<212> TYPE: PRT
<213> ORGANISM: artificial sequence
<220> FEATURE:
<223> OTHER INFORMATION: Synthetic

<400> SEQUENCE: 80

Ala Ala Pro Ala Ala
1               5
```